(12) United States Patent
Bakaletz et al.

(10) Patent No.: US 11,564,982 B2
(45) Date of Patent: Jan. 31, 2023

(54) DNABII VACCINES AND ANTIBODIES WITH ENHANCED ACTIVITY

(71) Applicant: Research Institute at Nationwide Children's Hospital, Columbus, OH (US)

(72) Inventors: Lauren O. Bakaletz, Hilliard, OH (US); Steven D. Goodman, Hilliard, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 243 days.

(21) Appl. No.: 16/475,656

(22) PCT Filed: Jan. 3, 2018

(86) PCT No.: PCT/US2018/012235
§ 371 (c)(1),
(2) Date: Jul. 2, 2019

(87) PCT Pub. No.: WO2018/129078
PCT Pub. Date: Jul. 12, 2018

(65) Prior Publication Data
US 2019/0337996 A1    Nov. 7, 2019

Related U.S. Application Data

(60) Provisional application No. 62/455,437, filed on Feb. 6, 2017, provisional application No. 62/453,921, filed on Feb. 2, 2017, provisional application No. 62/442,307, filed on Jan. 4, 2017.

(51) Int. Cl.
| | | |
|---|---|---|
| *A61P 31/04* | (2006.01) | |
| *A61K 39/102* | (2006.01) | |
| *A61K 45/06* | (2006.01) | |
| *C07K 14/285* | (2006.01) | |
| *C07K 16/12* | (2006.01) | |
| *G01N 33/569* | (2006.01) | |
| *A01N 63/50* | (2020.01) | |
| *A61K 38/00* | (2006.01) | |
| *A61K 39/00* | (2006.01) | |

(52) U.S. Cl.
CPC ............ *A61K 39/102* (2013.01); *A01N 63/50* (2020.01); *A61K 45/06* (2013.01); *A61P 31/04* (2018.01); *C07K 14/285* (2013.01); *C07K 16/1242* (2013.01); *G01N 33/56911* (2013.01); *A61K 38/00* (2013.01); *A61K 2039/505* (2013.01); *C07K 2317/20* (2013.01); *C07K 2317/24* (2013.01); *C07K 2317/55* (2013.01); *C07K 2319/00* (2013.01); *G01N 2333/285* (2013.01)

(58) Field of Classification Search
CPC ........ A61K 38/00; A61K 38/02; A61K 39/00; A61K 39/385; A61K 39/395; A61K 39/102; A61K 45/06; A61P 31/04; A01N 63/50; C07K 14/285; C07K 16/1242; G01N 33/56911; G01N 2333/285
USPC ................. 424/9.1, 9.2, 184.1, 185.1, 234.1; 536/23.1
See application file for complete search history.

(56) References Cited

U.S. PATENT DOCUMENTS

| | | |
|---|---|---|
| 6,551,795 B1 | 4/2003 | Rubenfield et al. |
| 6,663,863 B2 | 12/2003 | Horvath et al. |
| 6,696,550 B2 | 2/2004 | Larosa et al. |
| 6,846,651 B2 | 1/2005 | Fleischmann et al. |
| 7,241,867 B2 | 7/2007 | Bakaletz et al. |
| 7,413,868 B2 | 8/2008 | Kauvar et al. |
| 7,638,282 B2 | 12/2009 | Bakaletz et al. |
| 7,811,591 B2 | 10/2010 | Bakaletz et al. |
| 7,816,086 B2 | 10/2010 | Bakaletz et al. |
| 7,939,344 B2 | 5/2011 | Kauvar et al. |
| 7,998,490 B2 | 8/2011 | Bakaletz et al. |
| 8,236,494 B2 | 8/2012 | Bakaletz et al. |
| 8,283,114 B2 | 10/2012 | Bakaletz et al. |
| 8,628,917 B2 | 1/2014 | Bakaletz et al. |
| 8,652,773 B2 | 2/2014 | Bakaletz et al. |
| 8,758,764 B2 | 6/2014 | Masignani et al. |
| 8,933,029 B2 | 1/2015 | McNicol et al. |
| 8,999,291 B2* | 4/2015 | Goodman .......... C07K 16/1217 424/9.2 |
| 9,017,656 B2 | 4/2015 | Hancock et al. |
| 9,034,642 B2 | 5/2015 | Bakaletz et al. |
| 9,155,792 B2 | 10/2015 | Cottarel et al. |
| 9,745,366 B2 | 8/2017 | Goodman et al. |
| 10,233,234 B2 | 3/2019 | Kauvar et al. |

(Continued)

FOREIGN PATENT DOCUMENTS

| | | |
|---|---|---|
| WO | WO-02/085295 A2 | 10/2002 |
| WO | WO-2004/014418 A2 | 2/2004 |

(Continued)

OTHER PUBLICATIONS

Goldenberg et al. (Biochimie, 76:941-950, 1994).*
Goshima et al. (Gene, 118:97-102, 1992).*
Brockson et al., "Evaluation of the kinetics and mechanism of action of anti-integration host factor-mediated disruption of bacterial biofilms," Molecular Microbiology, DOI: 10.1111/mmi.12735 (Sep. 19, 2014).
Goldenberg et al., "Genetic and biochemical analysis of IHF/HU hybrid proteins," BioChimie (Paris, FR), vol. 76, No. 10-11, pp. 941-950 (Jan. 1, 1994).
International Preliminary Report on Patentability for PCT/US2018/012235 dated Mar. 18, 2019, 31 pages.

(Continued)

Primary Examiner — Mary Maille Lyons
(74) Attorney, Agent, or Firm — Foley & Lardner LLP

(57) ABSTRACT

The disclosure provides methods and compositions that are useful to lessen and/or cure bacterial biofilms and treat diseases or disorders associated with biofilms using one or more novel polypeptide vaccines, antibodies, antibody fragments and compositions. Bacteria that cannot form functional biofilms are more readily cleared by the remainder of the host's immune system and/or traditional antibiotics.

25 Claims, 10 Drawing Sheets

Specification includes a Sequence Listing.

(56) References Cited

U.S. PATENT DOCUMENTS

| | | |
|---|---|---|
| 10,570,193 B2 | 2/2020 | Kauvar et al. |
| 10,940,204 B2 | 3/2021 | Bakaletz et al. |
| 2003/0099602 A1 | 5/2003 | Levin et al. |
| 2003/0229065 A1 | 12/2003 | Levy et al. |
| 2004/0202670 A1 | 10/2004 | Apicella |
| 2005/0049402 A1 | 3/2005 | Babcook et al. |
| 2005/0131222 A1 | 6/2005 | Fleischmann et al. |
| 2005/0221439 A1 | 10/2005 | Bakaletz et al. |
| 2006/0030539 A1 | 2/2006 | Nick et al. |
| 2006/0228384 A1 | 10/2006 | Eldridge |
| 2006/0240045 A1 | 10/2006 | Berthet et al. |
| 2007/0207210 A1 | 9/2007 | Brown et al. |
| 2007/0264256 A1 | 11/2007 | Bakaletz et al. |
| 2009/0029929 A1 | 1/2009 | Nakajima et al. |
| 2009/0297555 A1 | 12/2009 | Kemble et al. |
| 2009/0324651 A1 | 12/2009 | Old et al. |
| 2010/0166771 A1 | 7/2010 | Bakaletz et al. |
| 2010/0291177 A1 | 11/2010 | Hermans et al. |
| 2010/0310569 A1 | 12/2010 | Bakaletz et al. |
| 2011/0135646 A1 | 6/2011 | Bakaletz et al. |
| 2011/0236306 A1 | 9/2011 | Goodman et al. |
| 2011/0293624 A1 | 12/2011 | Bakaletz et al. |
| 2012/0128701 A1 | 5/2012 | Goodman et al. |
| 2012/0148615 A1 | 6/2012 | Masignani et al. |
| 2013/0017204 A1 | 1/2013 | Bakaletz et al. |
| 2013/0078254 A1 | 3/2013 | Bakaletz et al. |
| 2013/0183323 A1 | 7/2013 | Wang |
| 2014/0120107 A1 | 5/2014 | Bakaletz et al. |
| 2014/0127221 A1 | 5/2014 | Bakaletz et al. |
| 2014/0287426 A1 | 9/2014 | Arnold et al. |
| 2014/0356389 A1 | 12/2014 | Masignani et al. |
| 2015/0086542 A1 | 3/2015 | Goodman et al. |
| 2015/0086561 A1 | 3/2015 | Kauvar et al. |
| 2015/0166641 A1 | 6/2015 | Goodman et al. |
| 2015/0197558 A1 | 7/2015 | Kauvar et al. |
| 2015/0216971 A1 | 8/2015 | Rotolo et al. |
| 2015/0218231 A1 | 8/2015 | Bakaletz et al. |
| 2015/0299298 A1 | 10/2015 | Kauvar et al. |
| 2016/0175440 A1 | 6/2016 | Goodman et al. |
| 2016/0194384 A1 | 7/2016 | Goodman et al. |
| 2016/0237145 A1 | 8/2016 | Kauvar et al. |
| 2016/0244489 A1 | 8/2016 | Masignani et al. |
| 2016/0289278 A1 | 10/2016 | Bakaletz et al. |
| 2016/0340650 A1 | 11/2016 | Wagner et al. |
| 2017/0182205 A1 | 6/2017 | Zupancic et al. |
| 2018/0303900 A1 | 10/2018 | Bakaletz et al. |
| 2019/0000971 A1 | 1/2019 | Bakaletz et al. |
| 2019/0040127 A1 | 2/2019 | Wadehra et al. |
| 2019/0338018 A1 | 11/2019 | Bakaletz et al. |
| 2020/0002409 A1 | 1/2020 | Goodman et al. |
| 2020/0190170 A1 | 6/2020 | Kauvar et al. |
| 2021/0206841 A1 | 7/2021 | Goodman et al. |

FOREIGN PATENT DOCUMENTS

| | | |
|---|---|---|
| WO | WO-2005/111066 A2 | 11/2005 |
| WO | WO-2006/017816 A2 | 2/2006 |
| WO | WO-2006/138527 A2 | 12/2006 |
| WO | WO-2009/006699 A1 | 1/2009 |
| WO | WO-2011/123396 A1 | 10/2011 |
| WO | WO-2014/201305 A1 | 12/2014 |
| WO | WO-2015/038339 A1 | 3/2015 |
| WO | WO-2015/048484 A2 | 4/2015 |
| WO | WO-2016/154491 A1 | 9/2016 |
| WO | WO-2017/023863 A1 | 2/2017 |
| WO | WO-2017/066719 A2 | 4/2017 |
| WO | WO-2017/192594 A1 | 11/2017 |
| WO | WO-2018/042385 A2 | 3/2018 |
| WO | WO-2018/129092 A1 | 7/2018 |
| WO | WO-2018/170178 A1 | 9/2018 |
| WO | WO-2021/007260 A2 | 1/2021 |

OTHER PUBLICATIONS

International Search Report and Written Opinion, PCT/US2018/012235 (dated Apr. 26, 2018).

Naoki et al., "Chimeric HU-IHF proteins that alter DNA-binding ability," GENE, vol. 118, No. 1, pp. 97-102 (Sep. 1, 1992).

Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, pp. 279-289 (Dec. 10, 2009).

Novotny et al., "Monoclonal antibodies against DNA-binding tips of DNABII proteins disrupt biofilms in vitro and induce bacterial clearance in vivo," EBIOMEDICINE, vol. 10, pp. 33-44 (Aug. 1, 2016).

Rice et al., "Crystal Structure of an IHF-DNA Complex: A Protein-Induced DNA U-Turn," CELL, vol. 87, No. 7, pp. 1295-1306 (Dec. 27, 1996).

Zulianello et al., "The HimA and HimD subunits of integration host factor can specifically bind to DNA as homodimers," The EMBO Journal, pp. 1534-1540 (Apr. 1, 1994).

U.S. Appl. No. 15/999,215, filed Aug. 16, 2018, Goodman et al.
U.S. Appl. No. 16/297,094, filed Mar. 8, 2019, Goodman et al.
U.S. Appl. No. 16/475,654, filed Jul. 2, 2019, Bakaletz et al.
U.S. Appl. No. 16/475,656, filed Jul. 2, 2019, Bakaletz et al.

Adams et al., "D-158. Epitope-mapping the immune response of children with otitis media and adults with chronic obstructive pulmonary disease to the PilA protein of nontypeable Haemophilus influenzae type IV pilus," 107th General Meeting, American Society for Microbiology; Toronto, ON, 2007, 1 page.

Adams et al., "Epitope-mapping the immune response of children with otitis media and adults with chronic obstructive pulmonary disease to the PilA protein of nontypeable Haemophilus influenzae type IV pilus," Immunology, 9th International Symposium on Recent Advances in Otitis Media; St. Pete Beach, FL, 2007, p. 356, 1 page.

Bakaletz et al., "New strategies to target bacterial biofilms", 28th Annual North American Cystic Fibrosis Conference (NACFC), Atlanta, GA, Oct. 9-11, 2014 (presentation), 2 pages.

Bakaletz et al., "Relative immunogenicity and efficacy of two synthetic chimeric peptides of fimbrin as vaccinogens against nasopharyngeal colonization by nontypeable Haemophilus influenzae in the chincilla," Vaccine, vol. 15, No. 9, 1997, pp. 955-961.

Bakaletz et al., "Protection against Development of Otitis Media Induced by Nontypeable Haemophilus influenzae by Both Active and Passive Immunization in a Chinchilla Model of Virus-Bacterium Superinfection," Infecion and Immunity, vol. 67, No. 6, Jun. 1999, pp. 2746-2762.

Bakaletz, "Biofilms can be dispersed by focusing the immune system on a common family of bacterial nucleoid associated proteins", 6th ASM Conference on Biofilms, Miami, FL, Sep. 29-Oct. 4, 2012 (presentation), 5 pages.

Bakaletz, L.O., Targeting the biofilm for development of novel preventative and therapeutic vaccine candidates to prevent otitis media, 6th ASM Conference on Biofilms, Miami, FL, Sep. 29-Oct. 4, 2012 (presentation), 5 pages.

Bass, J.I.F. et al. (2010) "Extracellular DNA: A Major Proinflammatory Component of Pseudomonas aeruginosa Biofilms," The Journal of Immunology 184:6386-6395.

Beech, I.B. et al. (2005) "Microbe-surface interactions in biofouling and biocorrosion processes," International Microbiology 8:157-168.

Bjarnsholt, T. (2013) "The role of bacterial biofilms in chronic infections," APMIS 121(Suppl. 136):1-51.

Boles, B.R. et al. (2011) "Staphylococcal biofilm disassembly," Trends in Microbiology 19(9):449-455.

Brady, R.A. et al. (2006) "Identification of *Staphylococcus aureus* Proteins Recognized by the Antibody-Mediated Immune Response to a Biofilm Infection," Infection and Immunity 74(6):3415-3426.

Brandstetter et al., "Antibodies Directed Against Integration Host Factor Mediate Biofilm Clearance From Nasopore," The Laryngoscope, vol. 12, No. 11, Nov. 2013, pp. 2626-2632.

(56) References Cited

OTHER PUBLICATIONS

Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258, Supplementary Material, 6 pages.

Brockson et al., Evaluation of the kinetics and mechanism of action of anti-integration host factor-mediated disruption of bacterial biofilms. Molecular microbiology. 2014;93(6): 1246-58. Epub Jul. 30, 2014, doi: 10.1 1 1 1/mmi.12735, PubMed PMID: 25069521 ; PMCID: 4160410.

Brown et al., "Tolerance to Single, but Not Multiple, Amino Acid Replacements in Antibody VHCDR2", J Immunol. May 1996, 155(9), pp. 3285-3291.

Catlin, "Extracellular Deoxyribonucleic Acid of Bacteria and a Deoxyribonuclease Inhibitor," Science, vol. 124, Sep. 7, 1956, pp. 441-442.

Chen et al., "Novel Strategies for the Prevention and Treatment of Biofilm Related Infections," Int. J. Mol. Sci., vol. 14, Sep. 6, 2013, pp. 18488-18501.

Chen, C. et al. (2004) "Substrate specificity of Helicobacter pylori histone-like HU protein is determined by insufficient stabilization of DNA flexure points," Biochem J. 383:343-351.

Coenye, T. et al. (2010) "In vitro and in vivo model systems to study microbial biofilm formation," Journal of Microbiological Methods 83:89-105.

Cohavy, O. et al. (1999) "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517.

Collarini, E.J. et al. (2009) "Potent High-Affinity Antibodies for Treatment and Prophylaxis of Respiratory Syncytial Virus Derived from B Cells of Infected Patients," J Immunol 183:6338-6345.

Dalai, B. et al. (2009) "Histone-like protein H-NS regulates biofilm formation and virulence of Actinobacillus pheuropneumonia," Microbial Pathogenesis 46:128-134.

Darouiche, R.O. et al. (2004) "Treatment of Infections Associated with Surgical Implants," N Engl J Med 350:1422-1429.

De La Fuente-Nunez et al., "Broad-Spectrum Anti-biofilm Peptide That Targets a Cellular Stress Response," PLoS Pathog., vol. 10, No. 5, May 2014, pp. 1-12.

Devaraj et al., "DNABII proteins play a central role in UPEC biofilm structure", Molecular Microbiology, 2017, vol. 96, vol. 6, Jun. 2015, pp. 1119-1135.

Dominguez-Herrera, J. et al. (2011) "Efficacy of Daptomycin versus Vancomycin in an Experimental Model of Foreign-Body and Systemic Infection Caused by Biofilm Producers and Methicillin-Resistant *Staphylococcus epidermidis*," Antimicrobial Agents and Chemotherapy 56(2):613-617.

Donlan, R.M. et al. (2002) "Biofilms: Survival Mechanisms of Clinically Relevant Microorganisms," Clinical Microbiology Reviews 15(2):167-193.

Durocher et al., "High-level and high-throughput recombinant protein production by transient transfection of suspension-growing human 293-EBNA1 cells," Nucleic Acids Research, vol. 30, No. 2, e9, Nov. 11, 2001, 9 pages.

Eboigbodin, K.E. et al. (2008) "Characterization of the Extracellular Plymeric Substances Produced by *Escherichia coli* Using Infrared Spectroscopic, Proteomic, and Aggregation Studies," Biomacromolecules 9:686-695.

Estelles et al., "A High-Affinity Native Human Antibody Disrupts Biofilm from *Staphylococcus aureus* Bacteria and Potentiates Antibiotic Efficacy in a Mouse Implant Infection Model," Antimicrobial Agents and Chemotherapy, vol. 60, No. 4, Apr. 2016, pp. 2292-2301.

Estrela et al., "Combining Biofilm-Controlling Compounds and Antibiotics as a Promising New Way to Control Biofilm Infections", Pharamceuticals, vol. 3, No. 5, May 11, 2010, pp. 1374-1393.

Estrela et al., "Combining Biofilm-Controlling Compounds and Antibiotics as a Promising New Way to Control Biofilm Infections," Pharmaceuticals, vol. 3, May 11, 2010, pp. 1374-1393.

Garcia-Contreras et al., "Protein Translation and Cell Death: The Role of Rare tRNAs in Biofilm Formation and in Activating Dormant Phage Killer Genes," PLoS ONE, vol. 3, No. 6, Jun. 11, 2008, e2394, 17 pages.

George et al., "Cystic fibrosis infections: treatment strategies and prospects," FEMS Microbiol Lett., vol. 300, Jun. 15, 2009, pp. 153-164.

Gerstel et al., "Complex Regulation of csgD Promoter Activity by Global Regulatory Proteins," Molecular Microbiology, vol. 49, No. 3, Aug. 2003, pp. 639-654.

Goodman et al., "Biofilms can be dispersed by focusing the immune system on a common family of bacterial nucleoid-associated proteins," Mucosal Immunology, vol. 4, No. 6, Nov. 2011, pp. 625-637.

Goodman et al., "In Vitro Selection of Integration Host Factor Binding Sites," Journal of Bacteriology, vol. 181, No. 10, May 1999, pp. 3246-3255.

Goodman et al., "Replacement of Integration Host Factor Protein-induced DNA Bending by Flexible Regions of DNA," The Journal of Biological Chemistry, vol. 274, No. 52, Aug. 6, 1999, pp. 37004-37011.

Goodman S D et al., "Biofilms can be dispersed by focusing the immune system on a common family of bacterial nucleoid-associated proteins", Mucosal Immuno, Nature Publishing Group, vol. 4, No. 6, Nov. 1, 2011, pp. 625-637.

Goodman, "A new immunotherapeutic approach that disperses biofilms, Banff Conference on Infectious Diseases", Banff, Alberta, Canada, May 18, 2012 (presentation), 9 pages.

Goodman, "Making and breaking biofilms", Ohio Branch American Society for Microbiology Annual Meeting, Columbus, OH, Apr. 11-12, 2014 (presentation), 12 pages.

Goodman, "Nucleoprotein complexes in the extracellular matrix are critical for the structural integrity of bacterial biofilms", 112th General Meeting, American Society for Microbiology, San Francisco, CA, Jun. 18, 2012 (presentation), 9 pages.

Goodman, "The DNABII family of proteins: Diagnostic markers and therapeutic targets of bacterial biofilms", International Congress on Bacteriology and Infectious Disease, Baltimore, MD, Nov. 21, 2013, 7 pages.

Govan et al., "Microbial pathogenesis in cystic fibrosis: mucoid Pseudomonas aeruginosa and Burkholderia cepacia," Microbiol. Rev., vol. 60, No. 3, Sep. 1996, pp. 539-574.

Granston et al., "Characterization of a Set of Integration Host Factor Mutants Deficient for DNA Binding," J. Mol. Biol., vol. 234, Jun. 21, 1993, pp. 45-59.

Greenspan et al., "Defining epitopes: It's not as easy as it seems," Nature Biotechnology, vol. 17, Oct. 1999, pp. 936-937.

Gustave et al., "Targeting bacterial integration host factor to disrupt biofilms associated with cystic fibrosis," Journal of Cystic Fibrosis, vol. 12, No. 4, Nov. 17, 2012, pp. 384-389.

Gustave et al., Biofilms recovered from the sputum of CF patients contain the bacterial protein integration host factor (IHF), 25th Annual North American Cystic Fibrosis Conference, Anaheim, CA, Nov. 3-5, 2011 (poster), 1 page.

Gustave et al., Targeting bacterial integration host factor to disrupt biofilms associated with cystic fibrosis. Journal of cystic fibrosis : official journal of the European Cystic Fibrosis Society.2013;12(4):384-9. Epub Nov. 22, 2012. doi: 10.1016/j.jcf.2012.10.011. PubMed PMID: 23168017; PMCID: 3582735.

Hall-Stoodley et al., "Bacterial Biofilms: From the Natural Environment to Infectious Diseases," Nature Reviews, Microbiology, vol. 2, Feb. 2004, pp. 95-108.

Hall-Stoodley et al., "Direct Detection of Bacterial Biofilms on the Middle-Ear Mucosa of Children With Chronic Otitis Media," JAMA, vol. 296, No. 2, Jun. 1, 2007, pp. 202-211.

Hall-Stoodley et al., "Evolving concepts in biofilm infections", Cellular Microbiology, vol. 11, No. 7, 2009, pp. 1034-1043.

Hall-Stoodley et al., "Characterization of biofilm matrix, degradation by DNase treatment and evidence of capsule downregulation in *Streptococcus pneumoniae* clinical isolates," BMC Microbiology, vol. 8, No. 173, Oct. 8, 2008, 16 pages.

Haluzi et al., "Genes Coding for Integration Host Factor Are Conserve in Gram-Negative Bacteria," Journal of Bacteriology, vol. 173, No. 19, Oct. 1991, pp. 6297-6299.

(56) References Cited

OTHER PUBLICATIONS

Harriman, W.D. et al. (2008) "Antibody discovery via multiplexed single cell characterization," Journal of Immunological Methods 341:135-145.

Harrison, J.J. et al. (2010) "Microfilter susceptibility testing of microbes growing on peg lids: a miniaturized biofilm model for high-throughput screening," Nature Protocols 5(7):1236-1254.

Haruta et al., "A possible role of histone-like DNA-binding protein of Streptococcus intermedius in the pathogenesis of bile duct damage in primary biliary cirrhosis," Clinical Immunology, vol. 127, No. 2, Mar. 11, 2008, pp. 245-251.

Haruta et al.,"Long-term bacterial exposure can trigger nonsuppurative destructive cholangitis associated with multifocal epithelial inflammation," Laboratory Investigation, vol. 90, Apr. 2010, pp. 577-588.

Haurum. "Recombinant polyclonal antibodies: the next generation of antibody therapeutics?" Drug Discovery Today. Jul. 2006;11(13-14):655-60.

Hoyle et al., "Bacterial Resistance to Antibiotics: The Role of Biofilms," Prog. Drug Res., vol. 37, 1991, pp. 91-105.

Idicula, W.K. et al. (2016) "Identification of Biofilms in Post-tympanostomy Tube Otorrhea," The Laryngoscope 126(8):1946-1951.

Janeway, "Manipulating the immune response to fight infection," Immunobiology: The Immune System in Health and Disease, 5th ed.; retrieved online from https://www.ncbi.nlm.nih.gov/books/NBK27131/, 2001, 13 pages.

Jiao et al., "Identification of Biofilm Matrix-Associated Proteins from an Acid Mine Drainage Microbial Community," Appl & Environ Microbiol., vol. 77, Aug. 2011, pp. 5230-5237.

Jodar et al., "Development of vaccines against meningococcal disease," Lancet, vol. 359, Apr. 27, 2002, pp. 1499-1508.

John, A-K. et al. (2011) "Reversible Daptomycin Tolerance of Adherent Staphylococci in an Implant Infection Model," Antimicrobial Agents and Chemotherapy 55(7):3510-3516.

Johnson et al., "Chapter 8: Bending and Compaction of DNA by Proteins," Protein-Nucleic Acid Interactions: Structural Biology, 2008, pp. 176-220.

Joo, H-S. et al. (2012) "Molecular Basis of In Vivo Formation by Bacterial Pathogens," Chemistry & Biology 19:1503-1513.

Jurcisek et al., "Role of Sialic Acid and Complex Carbohydrate Biosynthesis in Biofilm Formation by Nontypeable Haemophilus influenzae in the Chinchilla Middle Ear," Infection and Immunity, vol. 73, Jun. 2005, pp. 3210-3218.

Jurcisek et al., "Biofilms Formed by Nontypeable Haemophilus influenzae In Vivo Contain both Double-Stranded DNA and Type IV Pilin Protein," Journal of Bacteriology, vol. 189, No. 10, Feb. 15, 2007, pp. 3868-3875.

Jurcisek et al., Biofilms formed by nontypeable Haemophilus influenzae in vivo contain both double-stranded DNA and type IV pilin protein. Journal of bacteriology.2007;189(10):3868-75. Epub Feb. 27, 2007. doi: 10.1128/JB.01935-06. PubMed PMID: 17322318; PMCID: 1913342.

Justice et al., "Aberrant Community Architecture and Attenuated Persistence of Uropathogenic Escherichia coli in the Absence of Individual IHF Subunits," PLoS ONE, vol. 7, No. 10, Oct. 2012, pp. 1-11.

Kamashev D, Rouviere-Yaniv J. The histone-like protein HU binds specifically to DNA recombination and repair intermediates. The EMBO journal.2000;19(23):6527-35.

Kamashev et al., "The histone-like protein HU binds specifically to DNA recombination and repair intermediates," The EMBO Journal, vol. 19, No. 23, Oct. 13, 2000, pp. 6527-6535.

Kennedy et al., "Passive Transfer of Antiserum Specific for Immunogens Derived from a Nontypeable Haemophilus influenzae Adhesin and Lipoprotein D Prevents Otitis Media after Heterologous Challenge," Infection and Immunity, vol. 68, No. 5, May 2000, pp. 2756-2765.

Khrapunov, S. et al. (2006) "Binding then bending: A mechanism for wrapping DNA," PNAS 103(51):19217-19218.

Kim et al., "Beta-Arm flexibility of HU from Staphylococcus aureus dictates the DNA-binding and recognition mechanism," Acta Cryst., D70, Oct. 30, 2014, pp. 3273-3289.

Kim et al., "Proteins Released by Helicobacter pylori In Vitro," Journal of Bacteriology, vol. 184, No. 22, Nov. 2002, pp. 6155-6162.

Kirketerp-Moller et al., "Distribution, Organization, and Ecology of Bacteria in Chronic Wounds," Journal of Clinical Microbiology, vol. 46, No. 8, Aug. 2008, pp. 2717-2722.

Kristian, S.A. et al. (2003) "Alanylation of Teichoic Acids Protects Staphylococcus aureus against Toll-like Receptor 2-Dependent Host Defense in a Mouse Tissue Cage Infection Model," The Journal of Infectoius Diseases 188:414-423.

Kyd et al., "Efficacy of the 26-Kilodalton Outer Membrane Protein and Two P5 Fimbrin-Derived Immunogens To Induce Clearance of Nontypeable Haemophilus influenzae from the Rat Middle Ear and Lungs as Well as from the Chinchilla Middle Ear and Nasopharynx," Infection and Immunity, vol. 71, No. 8, Aug. 2003, pp. 4691-4699.

Lappann M, et al. A dual role of extracellular DNA during biofilm formation of Neisseria meningitidis. Molecular microbiology. 2010;75(6):1355-71. doi: 10.1111/j.1365-2958.2010.07054.x. PubMed PMID: 20180907.

Laura A. Novotny et al., "Monoclonal antibodies against DNA-binding tips of DNABII proteins disrupt biofilms in vitro and induce bacterial clearance in vivo", EBIOMEDICINE, vol. 10, Aug. 1, 2016, pp. 33-44.

Lebeaux et al., "From in vitro to in vivo Models of Bacterial Biofilm-Related Infections," Pathogens, vol. 2, May 13, 2013, pp. 288-356.

Liu et al., "The essentiality and involvement of Streptococcus intermedius histone-like DNA-binding protein in bacterial viability and normal growth," Molecular Microbiology, vol. 68, No. 5, Apr. 21, 2008, pp. 1268-1282.

Liu, D. et al. (2008) "Histone-like DNA binding protein of Streptococcus intermedius induces the expression of pro-inflammatory cytokines in human monocytes via activation of ERK1/2 and JNK pathways," Cellular Microbiology 10(1):262-276.

Lunsford et al., "DNA-Binding Activities in Streptococcus gordonii: Indentification of a Receptor-Nickase and a Histonelike Protein," Current Microbiology, vol. 32, 1996, pp. 95-100.

M. Elizabeth Brockson et al., "Evaluation of the kinetics and mechanism of action anti-integration host factor-mediated disruption of bacterial biofilms: Anti-IHF-mediated biofilm collapse", Molecular Microbiology., Aug. 19, 2014,pp. 1-22.

Malhotra et al., "Defining the functional epitopes of Integration Host Factor (IHF) to develop a novel biofilm-focused immunotherapeutic against nontypeable Haemophilus influenzae-induced chronic and recurrent otitis media", 18th International Symposium on Recent Advances in Otitis Media, National Harbor, MD, Jun. 7-11, 2015 (poster), 1 page.

Malhotra et al., "Fine mapping the functional epitopes within integration host factor, a novel therapeutic target for nontypeable Haemophilus influenza-induced diseases of the respiratory tract", Abst. 12th Annual AMA Research Symposium, Dallas, TX, Nov. 7, 2014, 1 page.

Malhotra et al., Identification of immunoprotective domains within the bacterial DNA-binding protein, integration host factor, 20th Annual Midwest Microbial Pathogenesis Meeting. The Ohio State University, Columbus, OH, Aug. 23-25, 2013 (poster),1 page.

Malhotra et al., Identification of immunoprotective domains within the bacterial DNA-binding protein, integration host factor, Abst. Seventh Extraordinary International Symposium on Recent Advances in Otitis Media, Stockholm, Sweden, Jun. 12, 2013, 20 pages.

Malhotra et al., Identification of immunoprotective domains within the bacterial DNA-binding protein, integration host factor, Seventh Extraordinary International Symposium on Recent Advances in Otitis Media, Stockholm, Sweden, Jun. 15, 2013 (presentation).

Mann, E.E. et al. (2009) "Modulation of eDNA Release and Degradation Affects Staphylococcus aureus Biofilm Maturation," PLoS ONE 4(6):e5822, 1-12.

Martinez-Antonio A et al. (2008), "Functional organization of Escherichia coli transcriptional regulatory network", J. Mol. Biol. vol. 381, p. 238-247.

(56) References Cited

OTHER PUBLICATIONS

Mouw et al., "Shaping the Borrelia burgdorferi genome: crystal structure and binding properties of the DNA-bending protein Hbb," Molecular Microbiology, vol. 63, No. 5, Jan. 22, 2007, pp. 1319-1330.

Mukherjee et al., "Quantitative protein expression and cell surface characteristics of *Escherichia coli* MG1655 biofilms," Proteomics, vol. 11, Nov. 1, 2010, pp. 339-351.

Murphy et al., "Microbial Interactions in the Respiratory Tract," The Pediatric Infectious Disease Journal, vol. 28, No. 10, Oct. 2009, pp. S121-S126.

Murphy, T.F. et al. (2002) "Biofilm formation by nontypeable Haemophilus influenzae: strain variablitiy, outer membrane antigen expression and role of pili," BMC Microbiology 2:7, 1-8.

Nash et al., "Overproduction of *Escherichia coli* Integration Host Factor, a Protein with Nonidentical Subunits," Journal of Bacteriology, vol. 169, No. 9, Sep. 1987, pp. 4124-4127.

NCBI Genebank: P0A6Y1 (Sep. 13, 2005), 7 pages.

Novotny et al. "Antibodies against the majority subunit of type IV Pili disperse nontypeable Haemophilus influenzae biofilms in a LuxS-dependent manner and confer therapeutic resolution of experimental otitis media" Mol Microbiol. Apr. 2015;96(2):276-92. doi: 10.1111/mmi.12934. First published: Jan. 19, 2015.

Novotny et al., "Antibodies against the majority subunit of Type 1V pili disperse nontypeable Haemophilus influenza biofilms in a LuxS-dependent manner and confer therapeutics resolution of experimental otitis media," Mol. Microbiol., vol. 96, No. 2, Apr. 2015, pp. 1-32.

Novotny et al., "Structural Stability of Burkholderia cenocepacia Biofilms Is Reliant on eDNA Structure and Presence of a Bacterial Nucleic Acid Binding Protein," Plos One, vol. 8, No. 6, e67629, Jun. 2013, 15 pages.

Novotny et al., "Detection and characterization of pediatric serum antibody to the OMP P5-homologous adhesin of nontypeable Haemophilus influenzae during acute otitis media," Vaccine, vol. 20, No. 29-30, Jun. 8, 2002, pp. 3590-3597.

Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, Aug. 22, 2009, pp. 279-289.

Novotny et al., "Epitope mapping of the Outer Membrane Protein P5-Homologous Fimbrin Adhesin of Nontypeable Haemophilus influenzae," Infection and Immunity, vol. 68, No. 4, Apr. 2000, pp. 2119-2128.

Novotny et al., "Passive immunization with human anti-protein D antibodies induced by polysaccharide protein D conjugates protects chinchillas against otitis media after intranasal challenge with Haemophilus influenzae," Vaccine, vol. 24, No. 22, Mar. 27, 2006, pp. 4804-4811.

Novotny et al., "The Fourth Surface-Exposed Region of the Outer Membrane Protein P5-Homologous Adhesin of the Nontypable Haemophilus influenzae Is an Immunodominant But Nonprotective Decoying Epitope," The Journal of Immunology, vol. 171, No. 4, Jun. 10, 2003, pp. 1978-1983.

Novotny LA, Amer AO, Brockson ME, Goodman SD, Bakaletz LO. Structural stability of Burkholderia cenocepacia biofilms is reliant on eDNA structure and presence of a bacterial nucleic acid binding protein. PloS one.2013;8(6):e67629. Epub Jun. 27, 2013. doi: 10.1371/journal.pone.0067629. PubMed PMID: 23799151; PMCID: 3682984.

Novotny, "Development of a novel biofilm-focused immunotherapeutic against NTHI-induced otitis media", 18th International Symposium on Recent Advances in Otitis Media, National Harbor, MD, Jun. 7-11, 2015 (presentation), 3 pages.

Novotny, L.A. et al. (2016) "Monoclonal antibodies against DNA-binding tips of DNABII proteins disrupt biofilms in vitro and induce bacterial clearance in vivo," EBioMedicine 10:33-44.

Oberto et al., "Histones, HMG, HU, IHF: Même combat," Biochimie, vol. 76, 1994, pp. 901-908.

Ordway et al., "Evaluation of Standard Chemotherapy in the Guinea Pig Model of Tuberculosis," Antimicrobial Agents and Chemotherapy, vol. 54, May 2010, pp. 1820-1833.

Otto, "*Staphylococcus epidermidis*—the 'accidental' pathogen," Nature Reviews Microbiology, vol. 7, Aug. 2009, pp. 555-567.

PDB ID: 1IHF: Rice, P.A. et al. (1996), 1 page; retrieved online from http://www.rcsb.org/pdb/explore.do?structureId=IHF, 2 pages.

Pedulla et al., "A novel host factor for integration of mycobacteriophage L5," Proc. Natl. Acad. Sci. USA, vol. 93, Dec. 1996, pp. 15411-15416.

Percival, S.L. et al. (2015) "Biofilms and Wounds: An Overview of the Evidence," Advances in Wound Care 4(7):373-381.

Petersen et al., "Biofilm Mode of Growth of *Streptococcus intermedius* Favoreed by a Competence-Stimulating Signaling Peptide," Journal of Bacteriology, vol. 186, No. 18, Sep. 2004, pp. 6327-6331.

Pethe et al., "*Mycobacterium smegmatis* laminin-binding glycoprotein shares epitopes with *Mycobacterium tuberculosis* heparin-binding haemagglutinin," Molecular Microbiology, vol. 39, No. 1, 2001, pp. 89-99.

Priyadarshini R, et al., The nucleoid-associated protein HUβ affects global gene expression in Porphyromonas gingivalis. Microbiology. 2013; 159(Pt2):219-29.First Published: Feb. 1, 2013.

Prymula et al., "Pneumococcal capsular polysaccharides conjugated to protein D for prevention of acute otitis media caused by both *Streptococcus pneumoniae* and non-typable Haemophilus influenzae: a randomized double-blind efficacy study," Lancet, vol. 367, No. 9512, Mar. 4, 2006, pp. 740-748.

Reffuveille et al., "A Broad-Spectrum Antibiofilm Peptide Enhances Antibiotic Action against Bacterial Biofilms", Antimicrobial Agents and Chemotherapy, vol. 58, No. 9, Sep. 2014, pp. 5363-5371.

Rice et al., "Crystal Structure of an IHF-DNA Complex: A Protein-Induced DNA U-Turn," Cell, vol. 87, No. 7, Dec. 27, 1996, pp. 1295-1306.

Rocco et al. "Natural antigenic differences in the functionally equivalent extracellular DNABII proteins of bacterial biofilms provide a means for targeted biofilm therapeutics" Mol Oral Microbiol. Apr. 2017;32(2):118-130. doi: 10.1111/omi.12157. First published: Mar. 14, 2016.

Rocco et al., "Natural antigenic differences in the fucntionally equivalent extracellular DNABI I proteins of bacterial biofilms provide a means for targeted biofilm therapeutics," Molecular Oral Microbiology, vol. 32, No. 2, Apr. 2017, pp. 1-21.

Rouviere-Yaniv J, Gros F. Characterization of a novel, low-molecular-weight DNA-binding protein from *Escherichia coli*. Proceedings of the National Academy of Sciences of the United States of America. 1975;72(9):3428-32. Epub Sep. 1, 1975. PubMed PMID: 1103148; PMCID: 433007.

Rudikoff et al., "Single amino acid substitution altering antigen-binding specificity," Proc. Natl. Acad. Sci. USA, vol. 79, No. 6, Mar. 1982, pp. 1979-1983.

Sapi et al., "Characterization of Biofilm Formation by Borrelia burgdorferi In Vitro," PLOS One, vol. 7, No. 10, Oct. 2012, pp. 1-11.

Schwartz, K. et al. (2012) "Functional Amyloids Composed of Phenol Soluble Modulins Stabilize *Staphylococcus aureus* Biofilms," PLOS Pathogens 8:e1002744, 1-11.

Segall et al., "Architectural elements in nucleoprotein complexes: interchangeability of specific and non-specific DNA binding proteins," The EMBO Journal, vol. 13, No. 19, 1994, pp. 4536-4548.

Shahrooei et al., "Inhibition of *Staphylococcus epidermidis* Biofilm Formation by Rabbit Polyclonal Antibodies against the SesC Protein," Infection and Immunity, vol. 77, No. 9, Sep. 2009, pp. 3670-3678.

Shields, R.C. et al. (2013) "Efficacy of a Marine Bacterial Nuclease against Biofilm Forming Microorganisms Isolated from Chronic Rhinosinusitis," PLoS ONE 8(2):e55339, 1-13.

Singh et al.,"Quorum-sensing signals indicate that cystic fibrosis lungs are infected with bacterial biofilms," Nature, vol. 407, No. 12, Oct. 12, 2000, pp. 762-764.

Skolnick, J. et al. (2000) "From genes to protein structure and function: novel applications of computational approaches in the genomic era," Trends in Biotechnology 18:34-39.

(56) References Cited

OTHER PUBLICATIONS

Smith et al., "Cystic Fibrosis Airway Epithelia Fail to Kill Bacteria Because of Abnormal Airway Surface Fluid," Cell, vol. 85, Apr. 19, 1996, pp. 229-236.
Stinson, M.W. et al. (1998) "Streptococcal Histone-Like Protein: Primary Structure of hlpA and Protein Binding to LipoteichoicAcid and Epithelial Cells," Infection and Immunity 66(1):259-265.
Stoltz et al., "Cystic Fibrosis Pigs Develop Lung Disease and Exhibit Defective Bacterial Eradication at Birth," www.ScienceTranslationMedicine.org, vol. 2, No. 29, Apr. 28, 2010, pp. 1-8.
Sun et al., "Inhibition of Biofilm Formation by Monoclonal Antibodies against *Staphylococcus epidermindis* RP62A Accumulation-Associated Protein," Clinical & Diagnostic Laboratory Immunology, vol. 12, No. 1, Jan. 2005, pp. 93-100.
Swinger et al., "IHF and HU: flexible architects of bent DNA," Current Opinion in Structural Biology, vol. 14, No. 1, 2004, pp. 28-35.
Takeda, "Polyhistidine Affinity Chromatography for Purification and Biochemical Analysis of Fungal Cell Wall-Degrading Enzymes," Affinity Chromatography, Dr. Sameh Magdeldin (Ed.), ISBN: 978-953-51-0325-7, In Tech, 2012, pp. 177-186.
Teter et al., "DNA Bending and Twisting Properties of Integration Host Factor Determined by DNA Cyclization," Plasmid, vol. 43, 2000, pp. 73-84.
Tetz et al., "Effect of DNase and Antibiotics on Biofilm Characteristics," Antimicrobial Agents and Chemotherapy, vol. 53, No. 3, Mar. 2009, pp. 1204-1209.
Thurnheer et al., "Colonisation of gingival epithelia by subgingival biofilms in vitro: role of 'red complex' bacteria", Arch Oral Biol., vol. 59, No. 9, Sep. 2014, pp. 1-24.
Thurnheer et al., "Colonisation of gingival epithelia by subgingival biofilms in vitro: role of 'red complex' bacteria," Archives in Oral Biology, vol. 59, No. 9, Sep. 2014, pp. 1-24.
Tjokro et al. A biochemical analysis of the interaction of Porphyromonas gingivalis HU PG0121 protein with DNA. PloS one. 2014;9(3):e93266. Epub Apr. 1, 2014 . doi: 10.1371.
UniProtKB/TrEMBL A0A0E4BIL9. Putative DNA-binding protein HU (Sep. 16, 2015) [Retrieved from the Internet Jan. 12, 2017: ],1 page.
UniProtKB/TrEMBL A0A0E4BIL9. Putative DNA-binding protein HU (Sep. 16, 2015) [Retrieved from the Internet Jan. 12, 2017: <http://www.uniprot.org/uniprot/A0A0E4BIL9.txt?version=3>], 1 page.
UniProtKB: TrEMBL A0A0E4BIL9. Putative DNA-binding protein HU, 2015, retrieved from www.uniprot.org/uniprot/A0A0E4BIL9.txt?version=3, 1 page.
Vajdos et al. "Comprehensive Functional Maps of the Antigen-binding Site of an Anti-ErbB2 Antibody Obtained with Shotgun Scanning Mutagenesis", J Mol. Biol., Jul. 5, 2002, 320(2), pp. 415-428.
Van Schaik et al., "DNA Binding: a Novel Function of Pseudomonas aeruginosa Type IV Pili," Journal of Bacteriology, vol. 187, No. 4, Feb. 2005, pp. 1455-1464.
Whitchurch et al., "Extracellular DNA Required for Bacterial Biofilm Formation," Science, vol. 295, No. 5559, Feb. 22, 2002, p. 1487, 1 page.
Whitchurch et al., "Extracellular DNA Required for Bacterial Biofilm Formation," Science, vol. 295, No. 5559, Feb. 22, 2002, Supplementary Material, 2 pages.
Wiedenheft et al., "RNA-guided genetic silencing systems in bacteria and archaea," Nature, vol. 482, No. 7385, Feb. 16, 2012, pp. 331-338.
Winters et al., "Isolation and Characterization of a *Streptococcus pyogenes* Protein that Binds to Basal Laminae of Human Cardiac Muscle," Infection and Immunity, vol. 61, No. 8, Aug. 1993, pp. 3259-3264.
Winther et al., "Location of Bacterial Biofilm in the Mucus Overlying the Adenoid by Light Microscopy," Head & Neck Surgery, vol. 135, No. 12, Dec. 2009, pp. 1239-1245.
Woischnig et al., "High Affinity Native Human Monoclonal Antibody with Broad Cross-Species Biofilm Disrupting Activity" poster presented at ICAAC Meeting on Sep. 20, 2015, available at www.trellisbio.com/assets/docs/ICAAC%20Biofilm%20Poster%2020150920.pdf., 1 page.
Woischnig et al., "High Affinity Native Human Monoclonal Antibody with Broad Cross-Species Biofilm Disrupting Activity", ICAAC, Sep. 20, 2015, 1 page.
Xiong et al., "A Human Biofilm-Disrupting Monoclonal Antibody Potentiates Antibiotic Efficacy in Rodent Models of both *Staphylococcus aureus* and Acinetobacter baumannii Infections," Antimicrob. Agents Chemother., vol. 61, No. 10, Oct. 2017, pp. 1-10.
Zimmerli et al., "Pathogenesis of Foreign Body Infection: Description and Characteristics of an Animal Model," The Journal of Infectious Diseases, vol. 146, No. 4, Oct. 1982, pp. 487-497.
Zimmerli, W. et al. (1984) "Pathogenesis of Foreign Body Infection," J. Clin. Invest. 73:1191-1200.
Janeway, et al., "Immunobiology—The Immune System in Health and Disease," Third Edition, 1997, Garland Publish Inc., 14 pages.
Novotny, L.A., et al., "Transcutaneous immunization as preventative and therapeutic regimens to protect against experimental otitis media due to nontypeable Haemophilus influenzae", Mucosal Immunol vol. 5 No. 1, Jul. 2011, pp. 456-467.

\* cited by examiner

IHF$_{NTHI}$ tip-directed chimeric peptide

'IhfA5-mIhfB4$_{NTHI}$ chimer' (SEQ ID NO: 50)
RPGRNPKTGDVVPVSARRVVGPSLFSLHHRQPRLGRNPKTGDSV IhfA5$_{NTHI}$ — linker — mIhfB4$_{NTHI}$ Regions targeted within IHF:

Reciprocal titers:

| Peptide | Chinchilla serum | | | |
|---|---|---|---|---|
| | Anti-IhfA3$_{NTHI}$ | Anti-IhfA5$_{NTHI}$ | Anti-mIhfB4$_{NTHI}$ | Anti-IhfA5-mB4$_{NTHI}$ chimer |
| IhfA5-mB4 chimer$_{NTHI}$ | 500 | 8K | 4K | 8K |

| Peptide | Rabbit serum | | | |
|---|---|---|---|---|
| | Anti-IhfA3$_{NTHI}$ | Anti-IhfA5$_{NTHI}$ | Anti-mIhfB4$_{NTHI}$ | Anti-IhfA5-mB4$_{NTHI}$ chimer |
| IhfA5-mB4 chimer$_{NTHI}$ | 500 | 80K | 320K | 640K |

SEQUENCE LISTING

<160> NUMBER OF SEQ ID NOS: 136

<210> SEQ ID NO 1
<211> LENGTH: 96
<212> TYPE: PRT
<213> ORGANISM: Haemophilus influenzae

```
<400> SEQUENCE: 1

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
                20                  25                  30

Glu Glu Ile Arg Leu Ser Leu Glu Ser Gly Gln Asp Val Lys Leu Ser
            35                  40                  45

Gly Phe Gly Asn Phe Glu Leu Arg Asp Lys Ser Ser Arg Pro Gly Arg
50                  55                  60

Asn Pro Lys Thr Gly Asp Val Val Pro Val Ser Ala Arg Arg Val Val
65                  70                  75                  80

Ile Thr Lys Pro Gly Gln Lys Leu Arg Ala Arg Val Glu Lys Ile Lys
                85                  90                  95

<210> SEQ ID NO 2
<211> LENGTH: 94
<212> TYPE: PRT
<213> ORGANISM: Haemophilus influenzae

<400> SEQUENCE: 2

Met Thr Lys Ser Glu Leu Met Glu Lys Leu Ser Ala Lys Gln Pro Thr
1               5                   10                  15

Leu Ser Ala Lys Glu Ile Glu Asn Met Val Lys Asp Ile Leu Glu Phe
                20                  25                  30

Ile Ser Gln Ser Leu Glu Asn Gly Asp Arg Val Glu Val Arg Gly Phe
            35                  40                  45

Gly Ser Phe Ser Leu His His Arg Gln Pro Arg Leu Gly Arg Asn Pro
50                  55                  60

Lys Thr Gly Asp Ser Val Asn Leu Ser Ala Lys Ser Val Pro Tyr Phe
65                  70                  75                  80

Lys Ala Gly Lys Glu Leu Lys Ala Arg Val Asp Val Gln Ala
                85                  90

<210> SEQ ID NO 3
<211> LENGTH: 136
<212> TYPE: PRT
<213> ORGANISM: Haemophilus influenzae

<400> SEQUENCE: 3

Met Arg Phe Val Thr Ile Phe Ile Asn His Ala Phe Asn Ser Ser Gln
1               5                   10                  15

Val Arg Leu Ser Phe Ala Gln Phe Leu Arg Gln Ile Arg Lys Asp Thr
                20                  25                  30

Phe Lys Glu Ser Asn Phe Leu Phe Asn Arg Arg Tyr Lys Phe Met Asn
            35                  40                  45

Lys Thr Asp Leu Ile Asp Ala Ile Ala Asn Ala Glu Leu Asn Lys
50                  55                  60

Lys Gln Ala Lys Ala Ala Leu Glu Ala Thr Leu Asp Ala Ile Thr Ala
65                  70                  75                  80

Ser Leu Lys Glu Gly Glu Pro Val Gln Leu Ile Gly Phe Gly Thr Phe
                85                  90                  95

Lys Val Asn Glu Arg Ala Ala Arg Thr Gly Arg Asn Pro Gln Thr Gly
                100                 105                 110

Ala Glu Ile Gln Ile Ala Ala Ser Lys Val Pro Ala Phe Val Ser Gly
            115                 120                 125

Lys Ala Leu Lys Asp Ala Ile Lys
```

130        135

<210> SEQ ID NO 4
<211> LENGTH: 96
<212> TYPE: PRT
<213> ORGANISM: Haemophilus influenzae

<400> SEQUENCE: 4

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

Gly Phe Gly Asn Phe Glu Leu Arg Asp Lys Ser Ser Arg Pro Gly Arg
    50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 5
<211> LENGTH: 96
<212> TYPE: PRT
<213> ORGANISM: Haemophilus influenzae

<400> SEQUENCE: 5

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

Gly Phe Gly Asn Phe Glu Leu Arg Asp Lys Ser Ser Arg Pro Gly Arg
    50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 6
<211> LENGTH: 99
<212> TYPE: PRT
<213> ORGANISM: Escherichia coli

<400> SEQUENCE: 6

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
        35                  40                  45

Phe Gly Asn Phe Asp Leu Arg Asp Lys Asn Gln Arg Pro Gly Arg Asn
    50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Ser Pro
                85                  90                  95

Lys Asp Glu

<210> SEQ ID NO 7
<211> LENGTH: 94
<212> TYPE: PRT
<213> ORGANISM: Escherichia coli

<400> SEQUENCE: 7

Met Thr Lys Ser Glu Leu Ile Glu Arg Leu Ala Thr Gln Gln Ser His
1               5                   10                  15

Ile Pro Ala Lys Thr Val Glu Asp Ala Val Lys Glu Met Leu Glu His
            20                  25                  30

Met Ala Ser Thr Leu Ala Gln Gly Glu Arg Ile Glu Ile Arg Gly Phe
        35                  40                  45

Gly Ser Phe Ser Leu His Tyr Arg Ala Pro Arg Thr Gly Arg Asn Pro
    50                  55                  60

Lys Thr Gly Asp Lys Val Glu Leu Glu Gly Lys Tyr Val Pro His Phe
65                  70                  75                  80

Lys Pro Gly Lys Glu Leu Arg Asp Arg Ala Asn Ile Tyr Gly
                85                  90

<210> SEQ ID NO 8
<211> LENGTH: 90
<212> TYPE: PRT
<213> ORGANISM: Escherichia coli

<400> SEQUENCE: 8

Met Asn Lys Thr Gln Leu Ile Asp Val Ile Ala Glu Lys Ala Glu Leu
1               5                   10                  15

Ser Lys Thr Gln Ala Lys Ala Ala Leu Glu Ser Thr Leu Ala Ala Ile
            20                  25                  30

Thr Glu Ser Leu Lys Glu Gly Asp Ala Val Gln Leu Val Gly Phe Gly
        35                  40                  45

Thr Phe Lys Val Asn His Arg Ala Glu Arg Thr Gly Arg Asn Pro Gln
    50                  55                  60

Thr Gly Lys Glu Ile Lys Ile Ala Ala Ala Asn Val Pro Ala Phe Val
65                  70                  75                  80

Ser Gly Lys Ala Leu Lys Asp Ala Val Lys
                85                  90

<210> SEQ ID NO 9
<211> LENGTH: 88
<212> TYPE: PRT
<213> ORGANISM: Escherichia coli

<400> SEQUENCE: 9

Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
            20                  25                  30

Thr Glu Ser Leu Lys Glu Gly Asp Asp Val Ala Leu Val Gly Phe Gly
        35                  40                  45

Thr Phe Ala Val Lys Glu Arg Ala Ala Arg Thr Gly Arg Asn Pro Gln
    50                  55                  60

Thr Gly Lys Glu Ile Ala Ala Ala Lys Val Pro Ser Phe Arg Ala Gly
65                  70                  75                  80

Lys Ala Leu Lys Asp Ala Val Asn

<210> SEQ ID NO 10
<211> LENGTH: 100
<212> TYPE: PRT
<213> ORGANISM: Pseudomonas aeruginosa

<400> SEQUENCE: 10

Met Gly Ala Leu Thr Lys Ala Glu Ile Ala Glu Arg Leu Tyr Glu Glu
1               5                   10                  15

Leu Gly Leu Asn Lys Arg Glu Ala Lys Glu Leu Val Glu Leu Phe Phe
            20                  25                  30

Glu Glu Ile Arg Gln Ala Leu Glu His Asn Glu Gln Val Lys Leu Ser
        35                  40                  45

Gly Phe Gly Asn Phe Asp Leu Arg Asp Lys Arg Gln Arg Pro Gly Arg
    50                  55                  60

Asn Pro Lys Thr Gly Glu Glu Ile Pro Ile Thr Ala Arg Arg Val Val
65                  70                  75                  80

Thr Phe Arg Pro Gly Gln Lys Leu Lys Ala Arg Val Glu Ala Tyr Ala
                85                  90                  95

Gly Thr Lys Ser
            100

<210> SEQ ID NO 11
<211> LENGTH: 94
<212> TYPE: PRT
<213> ORGANISM: Pseudomonas aeruginosa

<400> SEQUENCE: 11

Met Thr Lys Ser Glu Leu Ile Glu Arg Ile Val Thr His Gln Gly Gln
1               5                   10                  15

Leu Ser Ala Lys Asp Val Glu Leu Ala Ile Lys Thr Met Leu Glu Gln
            20                  25                  30

Met Ser Gln Ala Leu Ala Thr Gly Asp Arg Ile Glu Ile Arg Gly Phe
        35                  40                  45

Gly Ser Phe Ser Leu His Tyr Arg Ala Pro Arg Val Gly Arg Asn Pro
    50                  55                  60

Lys Thr Gly Glu Ser Val Arg Leu Asp Gly Lys Phe Val Pro His Phe
65                  70                  75                  80

Lys Pro Gly Lys Glu Leu Arg Asp Arg Val Asn Glu Pro Glu
                85                  90

<210> SEQ ID NO 12
<211> LENGTH: 20
<212> TYPE: PRT
<213> ORGANISM: Haemophilus influenzae

<400> SEQUENCE: 12

Phe Leu Glu Glu Ile Arg Leu Ser Leu Glu Ser Gly Gln Asp Val Lys
1               5                   10                  15

Leu Ser Gly Phe
            20

<210> SEQ ID NO 13
<211> LENGTH: 20
<212> TYPE: PRT
<213> ORGANISM: Haemophilus influenzae

<400> SEQUENCE: 13

Arg Pro Gly Arg Asn Pro Lys Thr Gly Asp Val Val Pro Val Ser Ala
1               5                   10                  15

Arg Arg Val Val
            20

<210> SEQ ID NO 14
<211> LENGTH: 20
<212> TYPE: PRT
<213> ORGANISM: Haemophilus influenzae

<400> SEQUENCE: 14

Arg Thr Gly Arg Asn Pro Gln Thr Gly Ala Glu Ile Gln Ile Ala Ala
1               5                   10                  15

Ser Lys Val Pro
            20

<210> SEQ ID NO 15
<211> LENGTH: 20
<212> TYPE: PRT
<213> ORGANISM: Haemophilus influenzae

<400> SEQUENCE: 15

Thr Leu Ser Ala Lys Glu Ile Glu Asn Met Val Lys Asp Ile Leu Glu
1               5                   10                  15

Phe Ile Ser Gln
            20

<210> SEQ ID NO 16
<211> LENGTH: 20
<212> TYPE: PRT
<213> ORGANISM: Haemophilus influenzae

<400> SEQUENCE: 16

Arg Gly Phe Gly Ser Phe Ser Leu His His Arg Gln Pro Arg Leu Gly
1               5                   10                  15

Arg Asn Pro Lys
            20

<210> SEQ ID NO 17
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Phe Ser Leu His His Arg Gln Pro Arg Leu Gly Arg Asn Pro Lys Thr
1               5                   10                  15

Gly Asp Ser Val
            20

<210> SEQ ID NO 18
<211> LENGTH: 20
<212> TYPE: PRT
<213> ORGANISM: Haemophilus influenzae

<400> SEQUENCE: 18

Met Ala Thr Ile Thr Lys Leu Asp Ile Ile Glu Tyr Leu Ser Asp Lys
1               5                   10                  15

Tyr His Leu Ser
            20

<210> SEQ ID NO 19
<211> LENGTH: 20
<212> TYPE: PRT
<213> ORGANISM: Haemophilus influenzae

<400> SEQUENCE: 19

Lys Tyr His Leu Ser Lys Gln Asp Thr Lys Asn Val Val Glu Asn Phe
1               5                   10                  15

Leu Glu Glu Ile
            20

<210> SEQ ID NO 20
<211> LENGTH: 20
<212> TYPE: PRT
<213> ORGANISM: Haemophilus influenzae

<400> SEQUENCE: 20

Lys Leu Ser Gly Phe Gly Asn Phe Glu Leu Arg Asp Lys Ser Ser Arg
1               5                   10                  15

Pro Gly Arg Asn
            20

<210> SEQ ID NO 21
<211> LENGTH: 21
<212> TYPE: PRT
<213> ORGANISM: Haemophilus influenzae

<400> SEQUENCE: 21

Ala Arg Arg Val Val Thr Phe Lys Pro Gly Gln Lys Leu Arg Ala Arg
1               5                   10                  15

Val Glu Lys Thr Lys
            20

<210> SEQ ID NO 22
<211> LENGTH: 20
<212> TYPE: PRT
<213> ORGANISM: Haemophilus influenzae

<400> SEQUENCE: 22

Met Thr Lys Ser Glu Leu Met Glu Lys Leu Ser Ala Lys Gln Pro Thr
1               5                   10                  15

Leu Ser Ala Lys
            20

<210> SEQ ID NO 23
<211> LENGTH: 20
<212> TYPE: PRT
<213> ORGANISM: Haemophilus influenzae

<400> SEQUENCE: 23

Glu Phe Ile Ser Gln Ser Leu Glu Asn Gly Asp Arg Val Glu Val Arg
1               5                   10                  15

Gly Phe Gly Ser
            20

<210> SEQ ID NO 24
<211> LENGTH: 20
<212> TYPE: PRT
<213> ORGANISM: Haemophilus influenzae

<400> SEQUENCE: 24

-continued

Gly Arg Asn Pro Lys Thr Gly Asp Ser Val Asn Leu Ser Ala Lys Ser
1               5                   10                  15

Val Pro Tyr Phe
            20

<210> SEQ ID NO 25
<211> LENGTH: 19
<212> TYPE: PRT
<213> ORGANISM: Haemophilus influenzae

<400> SEQUENCE: 25

Ser Val Pro Tyr Phe Lys Ala Gly Lys Glu Leu Lys Ala Arg Val Asp
1               5                   10                  15

Val Gln Ala

<210> SEQ ID NO 26
<211> LENGTH: 21
<212> TYPE: PRT
<213> ORGANISM: Haemophilus influenzae

<400> SEQUENCE: 26

Asn Phe Glu Leu Arg Asp Lys Ser Ser Arg Pro Gly Arg Asn Pro Lys
1               5                   10                  15

Thr Gly Asp Val Val
            20

<210> SEQ ID NO 27
<211> LENGTH: 21
<212> TYPE: PRT
<213> ORGANISM: Haemophilus influenzae

<400> SEQUENCE: 27

Ser Leu His His Arg Gln Pro Arg Leu Gly Arg Asn Pro Lys Thr Gly
1               5                   10                  15

Asp Ser Val Asn Leu
            20

<210> SEQ ID NO 28
<211> LENGTH: 22
<212> TYPE: PRT
<213> ORGANISM: Haemophilus influenzae

<400> SEQUENCE: 28

Met Asn Lys Thr Asp Leu Ile Asp Ala Ile Ala Asn Ala Ala Glu Leu
1               5                   10                  15

Asn Lys Lys Gln Ala Lys
            20

<210> SEQ ID NO 29
<211> LENGTH: 22
<212> TYPE: PRT
<213> ORGANISM: Haemophilus influenzae

<400> SEQUENCE: 29

Lys Lys Gln Ala Lys Ala Ala Leu Glu Ala Thr Leu Asp Ala Ile Thr
1               5                   10                  15

Ala Ser Leu Lys Glu Gly
            20

<210> SEQ ID NO 30
<211> LENGTH: 22
<212> TYPE: PRT

<213> ORGANISM: Haemophilus influenzae

<400> SEQUENCE: 30

Ser Leu Lys Glu Gly Glu Pro Val Gln Leu Ile Gly Phe Gly Thr Phe
1               5                   10                  15

Lys Val Asn Glu Arg Ala
            20

<210> SEQ ID NO 31
<211> LENGTH: 22
<212> TYPE: PRT
<213> ORGANISM: Haemophilus influenzae

<400> SEQUENCE: 31

Val Asn Glu Arg Ala Ala Arg Thr Gly Arg Asn Pro Gln Thr Gly Ala
1               5                   10                  15

Glu Ile Gln Ile Ala Ala
            20

<210> SEQ ID NO 32
<211> LENGTH: 22
<212> TYPE: PRT
<213> ORGANISM: Haemophilus influenzae

<400> SEQUENCE: 32

Ile Gln Ile Ala Ala Ser Lys Val Pro Ala Phe Val Ser Gly Lys Ala
1               5                   10                  15

Leu Lys Asp Ala Ile Lys
            20

<210> SEQ ID NO 33
<211> LENGTH: 384
<212> TYPE: PRT
<213> ORGANISM: Homo sapiens

<400> SEQUENCE: 33

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

```
Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Val Glu Glu Gly Leu Leu Glu Arg His Ser
            210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
            290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
            325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380

<210> SEQ ID NO 34
<211> LENGTH: 330
<212> TYPE: PRT
<213> ORGANISM: Homo sapiens

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

-continued

```
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 35
<211> LENGTH: 326
<212> TYPE: PRT
<213> ORGANISM: Homo sapiens

<400> SEQUENCE: 35

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
        130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
```

```
                210                 215                 220
Pro Gln Val Tyr Thr Leu Pro Ser Arg Glu Glu Met Thr Lys Asn
225                 230                 235                 240

Gln Val Ser Leu Thr Cys Leu Val Lys Gly Phe Tyr Pro Ser Asp Ile
                    245                 250                 255

Ser Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 36
<211> LENGTH: 377
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

-continued

```
Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375
```

<210> SEQ ID NO 37
<211> LENGTH: 452
<212> TYPE: PRT
<213> ORGANISM: Homo sapiens

<400> SEQUENCE: 37

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255
```

-continued

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Arg Phe Thr Cys Thr
    290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
    370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
            435                 440                 445

Gly Thr Cys Tyr
    450

<210> SEQ ID NO 38
<211> LENGTH: 327
<212> TYPE: PRT
<213> ORGANISM: Homo sapiens

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe

```
                165                 170                 175
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 39
<211> LENGTH: 353
<212> TYPE: PRT
<213> ORGANISM: Homo sapiens

<400> SEQUENCE: 39

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205
```

```
Pro Glu Ser Lys Thr Pro Leu Thr Ala Thr Leu Ser Lys Ser Gly Asn
    210             215                 220
Thr Phe Arg Pro Glu Val His Leu Leu Pro Pro Ser Glu Leu
225             230                 235                 240
Ala Leu Asn Glu Leu Val Thr Leu Thr Cys Leu Ala Arg Gly Phe Ser
            245                 250                 255
Pro Lys Asp Val Leu Val Arg Trp Leu Gln Gly Ser Gln Glu Leu Pro
            260                 265                 270
Arg Glu Lys Tyr Leu Thr Trp Ala Ser Arg Gln Glu Pro Ser Gln Gly
            275                 280                 285
Thr Thr Thr Phe Ala Val Thr Ser Ile Leu Arg Val Ala Ala Glu Asp
290                 295                 300
Trp Lys Lys Gly Asp Thr Phe Ser Cys Met Val Gly His Glu Ala Leu
305                 310                 315                 320
Pro Leu Ala Phe Thr Gln Lys Thr Ile Asp Arg Leu Ala Gly Lys Pro
                325                 330                 335
Thr His Val Asn Val Ser Val Val Met Ala Glu Val Asp Gly Thr Cys
            340                 345                 350
Tyr

<210> SEQ ID NO 40
<211> LENGTH: 340
<212> TYPE: PRT
<213> ORGANISM: Homo sapiens

<400> SEQUENCE: 40

Ala Ser Pro Thr Ser Pro Lys Val Phe Pro Leu Ser Leu Asp Ser Thr
1               5                   10                  15
Pro Gln Asp Gly Asn Val Val Val Ala Cys Leu Val Gln Gly Phe Phe
            20                  25                  30
Pro Gln Glu Pro Leu Ser Val Thr Trp Ser Glu Ser Gly Gln Asn Val
        35                  40                  45
Thr Ala Arg Asn Phe Pro Pro Ser Gln Asp Ala Ser Gly Asp Leu Tyr
    50                  55                  60
Thr Thr Ser Ser Gln Leu Thr Leu Pro Ala Thr Gln Cys Pro Asp Gly
65                  70                  75                  80
Lys Ser Val Thr Cys His Val Lys His Tyr Thr Asn Pro Ser Gln Asp
                85                  90                  95
Val Thr Val Pro Cys Pro Val Pro Pro Pro Pro Cys Cys His Pro
            100                 105                 110
Arg Leu Ser Leu His Arg Pro Ala Leu Glu Asp Leu Leu Leu Gly Ser
            115                 120                 125
Glu Ala Asn Leu Thr Cys Thr Leu Thr Gly Leu Arg Asp Ala Ser Gly
        130                 135                 140
Ala Thr Phe Thr Trp Thr Pro Ser Ser Gly Lys Ser Ala Val Gln Gly
145                 150                 155                 160
Pro Pro Glu Arg Asp Leu Cys Gly Cys Tyr Ser Val Ser Ser Val Leu
                165                 170                 175
Pro Gly Cys Ala Gln Pro Trp Asn His Gly Glu Thr Phe Thr Cys Thr
            180                 185                 190
Ala Ala His Pro Glu Leu Lys Thr Pro Leu Thr Ala Asn Ile Thr Lys
        195                 200                 205
Ser Gly Asn Thr Phe Arg Pro Glu Val His Leu Leu Pro Pro Ser
    210                 215                 220
```

```
Glu Glu Leu Ala Leu Asn Glu Leu Val Thr Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 41
<211> LENGTH: 106
<212> TYPE: PRT
<213> ORGANISM: Homo sapiens

<400> SEQUENCE: 41

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Pro Ser Leu Lys Leu
1               5

<210> SEQ ID NO 43
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43
```

Gly Gly Gly
1

<210> SEQ ID NO 44
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Pro Ser Leu
1

<210> SEQ ID NO 45
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Pro Ser
1

<210> SEQ ID NO 46
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Pro Ser Leu Lys
1

<210> SEQ ID NO 47
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Pro Ser Leu Lys
1               5

<210> SEQ ID NO 48
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Ser Leu Lys Leu
1

```
<210> SEQ ID NO 49
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Gly Ser Gly Gly Ser
1               5

<210> SEQ ID NO 50
<211> LENGTH: 44
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Arg Pro Gly Arg Asn Pro Lys Thr Gly Asp Val Val Pro Val Ser Ala
1               5                   10                  15

Arg Arg Val Val Gly Pro Ser Leu Phe Ser Leu His His Arg Gln Pro
            20                  25                  30

Arg Leu Gly Arg Asn Pro Lys Thr Gly Asp Ser Val
        35                  40

<210> SEQ ID NO 51
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent

<400> SEQUENCE: 51

Arg Pro Gly Arg Asn Pro Lys Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Lys Thr Gly Asp Ser Val
    50                  55                  60

<210> SEQ ID NO 52
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
```

```
<222> LOCATION: (61)..(80)
<223> OTHER INFORMATION: Any amino acid or absent

<400> SEQUENCE: 52

Phe Ser Leu His His Arg Gln Pro Arg Leu Gly Arg Asn Pro Lys Thr
1               5                   10                  15

Gly Asp Ser Val Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Phe Ser Leu His His Arg Gln Pro
            35                  40                  45

Arg Leu Gly Arg Asn Pro Lys Thr Gly Asp Ser Val Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Arg Pro Gly Arg Asn Pro Lys Thr Gly Asp Val Val Pro Val Ser Ala
                85                  90                  95

Arg Arg Val Val
            100

<210> SEQ ID NO 53
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent

<400> SEQUENCE: 53

Phe Ser Leu His His Arg Gln Pro Arg Leu Gly Arg Asn Pro Lys Thr
1               5                   10                  15

Gly Asp Ser Val Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Arg Pro Gly Arg Asn Pro Lys Thr
            35                  40                  45

Gly Asp Val Val Pro Val Ser Ala Arg Arg Val Val Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Phe Ser Leu His His Arg Gln Pro Arg Leu Gly Arg Asn Pro Lys Thr
                85                  90                  95

Gly Asp Ser Val
            100

<210> SEQ ID NO 54
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
```

-continued

<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent

<400> SEQUENCE: 54

Arg Pro Gly Arg Asn Pro Lys Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Lys Thr Gly Asp Ser Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Phe Ser Leu His His Arg Gln Pro Arg Leu Gly Arg Asn Pro Lys Thr
                85                  90                  95

Gly Asp Ser Val
            100

<210> SEQ ID NO 55
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent

<400> SEQUENCE: 55

Arg Pro Gly Arg Asn Pro Lys Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Arg Pro Gly Arg Asn Pro Lys Thr
        35                  40                  45

Gly Asp Val Val Pro Val Ser Ala Arg Arg Val Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Phe Ser Leu His His Arg Gln Pro Arg Leu Gly Arg Asn Pro Lys Thr
                85                  90                  95

Gly Asp Ser Val
            100

<210> SEQ ID NO 56
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent

<400> SEQUENCE: 56

Arg Pro Gly Arg Asn Pro Lys Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Lys Thr Gly Asp Ser Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Arg Pro Gly Arg Asn Pro Lys Thr Gly Asp Val Val Pro Val Ser Ala
                85                  90                  95

Arg Arg Val Val
            100

<210> SEQ ID NO 57
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent

<400> SEQUENCE: 57

Phe Ser Leu His His Arg Gln Pro Arg Leu Gly Arg Asn Pro Lys Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Arg Pro Gly Arg Asn Pro Lys Thr
        35                  40                  45

Gly Asp Val Val Pro Val Ser Ala Arg Arg Val Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Arg Pro Gly Arg Asn Pro Lys Thr Gly Asp Val Val Pro Val Ser Ala
                85                  90                  95

Arg Arg Val Val
            100

<210> SEQ ID NO 58
<211> LENGTH: 140
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (101)..(120)
<223> OTHER INFORMATION: Any amino acid or absent

<400> SEQUENCE: 58

Phe Ser Leu His His Arg Gln Pro Arg Leu Gly Arg Asn Pro Lys Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Lys Thr Gly Asp Ser Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Arg Pro Gly Arg Asn Pro Lys Thr Gly Asp Val Val Pro Val Ser Ala
                85                  90                  95

Arg Arg Val Val Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Arg Pro Gly Arg Asn Pro Lys Thr
        115                 120                 125

Gly Asp Val Val Pro Val Ser Ala Arg Arg Val Val
    130                 135                 140

<210> SEQ ID NO 59
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (101)..(120)
<223> OTHER INFORMATION: Any amino acid or absent

<400> SEQUENCE: 59

Phe Ser Leu His His Arg Gln Pro Arg Leu Gly Arg Asn Pro Lys Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Arg Pro Gly Arg Asn Pro Lys Thr
        35                  40                  45

Gly Asp Val Val Pro Val Ser Ala Arg Arg Val Val Xaa Xaa Xaa Xaa
```

```
                    50                  55                  60
Xaa Xaa Xaa Xaa Xaa Xaa Xaa Xaa Xaa Xaa Xaa Xaa Xaa Xaa Xaa Xaa
 65                  70                  75                  80

Phe Ser Leu His His Arg Gln Pro Arg Leu Gly Arg Asn Pro Lys Thr
                 85                  90                  95

Gly Asp Ser Val Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Arg Pro Gly Arg Asn Pro Lys Thr
            115                 120                 125

Gly Asp Val Val Pro Val Ser Ala Arg Arg Val Val
            130                 135                 140

<210> SEQ ID NO 60
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (101)..(120)
<223> OTHER INFORMATION: Any amino acid or absent

<400> SEQUENCE: 60

Arg Pro Gly Arg Asn Pro Lys Thr Gly Asp Val Val Pro Val Ser Ala
  1               5                  10                  15

Arg Arg Val Val Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Phe Ser Leu His His Arg Gln Pro
         35                  40                  45

Arg Leu Gly Arg Asn Pro Lys Thr Gly Asp Ser Val Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Arg Pro Gly Arg Asn Pro Lys Thr Gly Asp Val Val Pro Val Ser Ala
                 85                  90                  95

Arg Arg Val Val Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Phe Ser Leu His His Arg Gln Pro
            115                 120                 125

Arg Leu Gly Arg Asn Pro Lys Thr Gly Asp Ser Val
            130                 135                 140

<210> SEQ ID NO 61
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
```

-continued

```
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (101)..(120)
<223> OTHER INFORMATION: Any amino acid or absent

<400> SEQUENCE: 61

Phe Ser Leu His His Arg Gln Pro Arg Leu Gly Arg Asn Pro Lys Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Arg Pro Gly Arg Asn Pro Lys Thr
        35                  40                  45

Gly Asp Val Val Pro Val Ser Ala Arg Arg Val Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Arg Pro Gly Arg Asn Pro Lys Thr Gly Asp Val Val Pro Val Ser Ala
                85                  90                  95

Arg Arg Val Val Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Phe Ser Leu His His Arg Gln Pro
        115                 120                 125

Arg Leu Gly Arg Asn Pro Lys Thr Gly Asp Ser Val
    130                 135                 140

<210> SEQ ID NO 62
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (101)..(120)
<223> OTHER INFORMATION: Any amino acid or absent

<400> SEQUENCE: 62

Arg Pro Gly Arg Asn Pro Lys Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Lys Thr Gly Asp Ser Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80
```

```
Phe Ser Leu His His Arg Gln Pro Arg Leu Gly Arg Asn Pro Lys Thr
                85                  90                  95

Gly Asp Ser Val Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Arg Pro Gly Arg Asn Pro Lys Thr
        115                 120                 125

Gly Asp Val Val Pro Val Ser Ala Arg Arg Val Val
130                 135                 140

<210> SEQ ID NO 63
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (101)..(120)
<223> OTHER INFORMATION: Any amino acid or absent

<400> SEQUENCE: 63

Arg Pro Gly Arg Asn Pro Lys Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Arg Pro Gly Arg Asn Pro Lys Thr
        35                  40                  45

Gly Asp Val Val Pro Val Ser Ala Arg Arg Val Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Phe Ser Leu His His Arg Gln Pro Arg Leu Gly Arg Asn Pro Lys Thr
                85                  90                  95

Gly Asp Ser Val Xaa Xaa Xaa Xaa Xaa Xaa Xaa Xaa Xaa Xaa Xaa Xaa
            100                 105                 110

Xaa Xaa Xaa Xaa Xaa Xaa Xaa Phe Ser Leu His His Arg Gln Pro
        115                 120                 125

Arg Leu Gly Arg Asn Pro Lys Thr Gly Asp Ser Val
130                 135                 140

<210> SEQ ID NO 64
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (21)..(40)
```

```
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 64

Arg Pro Gly Arg Asn Pro Xaa Thr Gly Asp Val Val Pro Val Ser Ala
1               5                   10                  15

Arg Arg Val Val Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Xaa Thr Gly Asp Ser Val
    50                  55                  60

<210> SEQ ID NO 65
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (87)..(87)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 65

Phe Ser Leu His His Arg Gln Pro Arg Leu Gly Arg Asn Pro Xaa Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Xaa Thr Gly Asp Ser Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Arg Pro Gly Arg Asn Pro Xaa Thr Gly Asp Val Val Pro Val Ser Ala
                85                  90                  95

Arg Arg Val Val
```

<210> SEQ ID NO 66
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (95)..(95)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 66

Phe Ser Leu His His Arg Gln Pro Arg Leu Gly Arg Asn Pro Xaa Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Arg Pro Gly Arg Asn Pro Xaa Thr
        35                  40                  45

Gly Asp Val Val Pro Val Ser Ala Arg Arg Val Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Phe Ser Leu His His Arg Gln Pro Arg Leu Gly Arg Asn Pro Xaa Thr
                85                  90                  95

Gly Asp Ser Val
            100

<210> SEQ ID NO 67
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (55)..(55)

```
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (95)..(95)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 67

Arg Pro Gly Arg Asn Pro Xaa Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Xaa Thr Gly Asp Ser Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Phe Ser Leu His His Arg Gln Pro Arg Leu Gly Arg Asn Pro Xaa Thr
                85                  90                  95

Gly Asp Ser Val
            100

<210> SEQ ID NO 68
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (95)..(95)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 68

Arg Pro Gly Arg Asn Pro Xaa Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30
```

```
Xaa Xaa Xaa Xaa Xaa Xaa Xaa Arg Pro Gly Arg Asn Pro Xaa Thr
            35                  40                  45

Gly Asp Val Val Pro Val Ser Ala Arg Arg Val Val Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Phe Ser Leu His His Arg Gln Pro Arg Leu Gly Arg Asn Pro Xaa Thr
                 85                  90                  95

Gly Asp Ser Val
            100

<210> SEQ ID NO 69
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (87)..(87)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 69

Arg Pro Gly Arg Asn Pro Xaa Thr Gly Asp Val Val Pro Val Ser Ala
 1               5                  10                  15

Arg Arg Val Val Xaa Xaa Xaa Xaa Xaa Xaa Xaa Xaa Xaa Xaa Xaa Xaa
                 20                  25                  30

Xaa Xaa Xaa Xaa Xaa Xaa Xaa Xaa Phe Ser Leu His His Arg Gln Pro
            35                  40                  45

Arg Leu Gly Arg Asn Pro Xaa Thr Gly Asp Ser Val Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Arg Pro Gly Arg Asn Pro Xaa Thr Gly Asp Val Val Pro Val Ser Ala
                 85                  90                  95

Arg Arg Val Val
            100

<210> SEQ ID NO 70
<211> LENGTH: 100
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic polypeptide"
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (87)..(87)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 70

Phe Ser Leu His His Arg Gln Pro Arg Leu Gly Arg Asn Pro Xaa Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Arg Pro Gly Arg Asn Pro Xaa Thr
        35                  40                  45

Gly Asp Val Val Pro Val Ser Ala Arg Arg Val Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Arg Pro Gly Arg Asn Pro Xaa Thr Gly Asp Val Val Pro Val Ser Ala
                85                  90                  95

Arg Arg Val Val
            100

<210> SEQ ID NO 71
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (87)..(87)
<223> OTHER INFORMATION: Any amino acid
```

-continued

```
<220> FEATURE:
<221> NAME/KEY: MOD_RES
<222> LOCATION: (101)..(120)
<223> OTHER INFORMATION: Any amino acid or absent
<220> FEATURE:
<221> NAME/KEY: MOD_RES
<222> LOCATION: (127)..(127)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 71

Phe Ser Leu His His Arg Gln Pro Arg Leu Gly Arg Asn Pro Xaa Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Xaa Thr Gly Asp Ser Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Arg Pro Gly Arg Asn Pro Xaa Thr Gly Asp Val Val Pro Val Ser Ala
                85                  90                  95

Arg Arg Val Val Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Arg Pro Gly Arg Asn Pro Xaa Thr
            115                 120                 125

Gly Asp Val Val Pro Val Ser Ala Arg Arg Val Val
            130                 135                 140

<210> SEQ ID NO 72
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (101)..(120)
<223> OTHER INFORMATION: Any amino acid or absent
<220> FEATURE:
<221> NAME/KEY: MOD_RES
<222> LOCATION: (127)..(127)
<223> OTHER INFORMATION: Any amino acid
```

```
<220> FEATURE:
<221> NAME/KEY: source
<223> OTHER INFORMATION: /note="See specification as filed for detailed
      description of substitutions and preferred embodiments"

<400> SEQUENCE: 72

Phe Ser Leu His His Arg Gln Pro Arg Leu Gly Arg Asn Pro Xaa Thr
1               5                   10                  15

Gly Asp Ser Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Arg Pro Gly Arg Asn Pro Xaa Thr
        35                  40                  45

Gly Asp Val Val Pro Val Ser Ala Arg Arg Val Val Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Phe Ser Leu His His Arg Gln Pro Arg Leu Gly Arg Asn Pro Xaa Thr
                85                  90                  95

Gly Asp Ser Val Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Arg Pro Gly Arg Asn Pro Xaa Thr
        115                 120                 125

Gly Asp Val Val Pro Val Ser Ala Arg Arg Val Val
    130                 135                 140

<210> SEQ ID NO 73
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (87)..(87)
<223> OTHER INFORMATION: Any amino acid
<220> FEATURE:
<221> NAME/KEY: MOD_RES
<222> LOCATION: (101)..(120)
<223> OTHER INFORMATION: Any amino acid or absent
<220> FEATURE:
<221> NAME/KEY: MOD_RES
<222> LOCATION: (135)..(135)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 73

Arg Pro Gly Arg Asn Pro Xaa Thr Gly Asp Val Val Pro Val Ser Ala
```

```
    1               5                   10                  15
Arg Arg Val Val Xaa Xaa Xaa Xaa Xaa Xaa Xaa Xaa Xaa Xaa
            20                  25                  30
Xaa Xaa Xaa Xaa Xaa Xaa Xaa Xaa Phe Ser Leu His His Arg Gln Pro
        35                  40                  45
Arg Leu Gly Arg Asn Pro Xaa Thr Gly Asp Ser Val Xaa Xaa Xaa Xaa
        50                  55                  60
Xaa Xaa Xaa Xaa Xaa Xaa Xaa Xaa Xaa Xaa Xaa Xaa Xaa Xaa Xaa Xaa
65                  70                  75                  80
Arg Pro Gly Arg Asn Pro Xaa Thr Gly Asp Val Val Pro Val Ser Ala
                85                  90                  95
Arg Arg Val Val Xaa Xaa Xaa Xaa Xaa Xaa Xaa Xaa Xaa Xaa
            100                 105                 110
Xaa Xaa Xaa Xaa Xaa Xaa Xaa Xaa Phe Ser Leu His His Arg Gln Pro
        115                 120                 125
Arg Leu Gly Arg Asn Pro Xaa Thr Gly Asp Ser Val
    130                 135                 140
```

<210> SEQ ID NO 74
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (87)..(87)
<223> OTHER INFORMATION: Any amino acid
<220> FEATURE:
<221> NAME/KEY: MOD_RES
<222> LOCATION: (101)..(120)
<223> OTHER INFORMATION: Any amino acid or absent
<220> FEATURE:
<221> NAME/KEY: MOD_RES
<222> LOCATION: (135)..(135)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 74

```
Phe Ser Leu His His Arg Gln Pro Arg Leu Gly Arg Asn Pro Xaa Thr
1               5                   10                  15
Gly Asp Ser Val Xaa Xaa Xaa Xaa Xaa Xaa Xaa Xaa Xaa Xaa Xaa Xaa
            20                  25                  30
Xaa Xaa Xaa Xaa Xaa Xaa Xaa Xaa Arg Pro Gly Arg Asn Pro Xaa Thr
        35                  40                  45
```

Gly Asp Val Val Pro Val Ser Ala Arg Arg Val Val Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Arg Pro Gly Arg Asn Pro Xaa Thr Gly Asp Val Val Pro Val Ser Ala
                 85                  90                  95

Arg Arg Val Val Xaa Xaa Xaa Xaa Xaa Xaa Xaa Xaa Xaa Xaa Xaa Xaa
            100                 105                 110

Xaa Xaa Xaa Xaa Xaa Xaa Xaa Phe Ser Leu His His Arg Gln Pro
        115                 120                 125

Arg Leu Gly Arg Asn Pro Xaa Thr Gly Asp Ser Val
    130                 135                 140

<210> SEQ ID NO 75
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (55)..(55)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (101)..(120)
<223> OTHER INFORMATION: Any amino acid or absent
<220> FEATURE:
<221> NAME/KEY: MOD_RES
<222> LOCATION: (127)..(127)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 75

Arg Pro Gly Arg Asn Pro Xaa Thr Gly Asp Val Val Pro Val Ser Ala
  1               5                  10                  15

Arg Arg Val Val Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Phe Ser Leu His His Arg Gln Pro
         35                  40                  45

Arg Leu Gly Arg Asn Pro Xaa Thr Gly Asp Ser Val Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Phe Ser Leu His His Arg Gln Pro Arg Leu Gly Arg Asn Pro Xaa Thr
             85                  90                  95

```
Gly Asp Ser Val Xaa Xaa Xaa Xaa Xaa Xaa Xaa Xaa Xaa Xaa
                100                 105                 110

Xaa Xaa Xaa Xaa Xaa Xaa Xaa Arg Pro Gly Arg Asn Pro Xaa Thr
        115                 120                 125

Gly Asp Val Val Pro Val Ser Ala Arg Arg Val Val
    130                 135                 140

<210> SEQ ID NO 76
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (21)..(40)
<223> OTHER INFORMATION: Any amino acid or absent
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (61)..(80)
<223> OTHER INFORMATION: Any amino acid or absent
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (101)..(120)
<223> OTHER INFORMATION: Any amino acid or absent
<220> FEATURE:
<221> NAME/KEY: MOD_RES
<222> LOCATION: (135)..(135)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 76

Arg Pro Gly Arg Asn Pro Xaa Thr Gly Asp Val Val Pro Val Ser Ala
1               5                   10                  15

Arg Arg Val Val Xaa Xaa Xaa Xaa Xaa Xaa Xaa Xaa Xaa Xaa Xaa
            20                  25                  30

Xaa Xaa Xaa Xaa Xaa Xaa Xaa Xaa Arg Pro Gly Arg Asn Pro Xaa Thr
        35                  40                  45

Gly Asp Val Val Pro Val Ser Ala Arg Arg Val Val Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Phe Ser Leu His His Arg Gln Pro Arg Leu Gly Arg Asn Pro Xaa Thr
                85                  90                  95

Gly Asp Ser Val Xaa Xaa Xaa Xaa Xaa Xaa Xaa Xaa Xaa Xaa
                100                 105                 110

Xaa Xaa Xaa Xaa Xaa Xaa Xaa Xaa Phe Ser Leu His His Arg Gln Pro
        115                 120                 125

Arg Leu Gly Arg Asn Pro Xaa Thr Gly Asp Ser Val
            130                 135                 140
```

<210> SEQ ID NO 77
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 77

Asp Lys Ser Ser Arg Pro Gly Arg Asn Pro Xaa Thr Gly Asp Val Val
1               5                   10                  15

Ala Ala Ser Ala Arg Arg
            20

<210> SEQ ID NO 78
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Phe Asp Leu Arg Asp Lys Asn Gln Arg Pro Gly Arg Asn Pro Lys Thr
1               5                   10                  15

Gly Glu Asp Ile
            20

<210> SEQ ID NO 79
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Phe Asp Leu Arg Asp Lys Asn Gln Arg Pro Gly Arg Asn Pro Lys Thr
1               5                   10                  15

Gly Glu Asp Ile
            20

<210> SEQ ID NO 80
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Phe Asp Leu Arg Asp Lys Asn Glu Arg Pro Gly Arg Asn Pro Lys Thr
1               5                   10                  15

<210> SEQ ID NO 81
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

Phe Asp Leu Arg Asp Lys Arg Gln Arg Pro Gly Arg Asn Pro Lys Thr
1               5                   10                  15
Gly Glu Glu Ile
            20

<210> SEQ ID NO 82
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

Phe Glu Leu Arg Asp Lys Ser Ser Arg Pro Gly Arg Asn Pro Lys Thr
1               5                   10                  15
Gly Asp Val Val
            20

<210> SEQ ID NO 83
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 83

Phe Glu Leu Arg Asp Lys Ala Ser Arg Pro Gly Arg Asn Pro Lys Thr
1               5                   10                  15
Gly Glu Ser Val
            20

<210> SEQ ID NO 84
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 84

Phe Glu Leu Lys Asp Lys Lys Pro Arg Pro Gly Arg Asn Pro Lys Thr
1               5                   10                  15
Gly Glu Ser Val
            20

<210> SEQ ID NO 85
<211> LENGTH: 20
<212> TYPE: PRT

-continued

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Phe Gln Leu Arg Asp Lys Pro Gln Arg Pro Gly Arg Asn Pro Lys Thr
1               5                   10                  15

Gly Glu Glu Val
            20

<210> SEQ ID NO 86
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Phe Gln Leu Arg Asp Lys Pro Gln Arg Pro Gly Arg Asn Pro Lys Thr
1               5                   10                  15

Gly Glu Glu Val
            20

<210> SEQ ID NO 87
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Phe Gln Leu Arg Asp Lys Pro Gln Arg Pro Gly Arg Asn Pro Lys Thr
1               5                   10                  15

Gly Glu Ala Ile
            20

<210> SEQ ID NO 88
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Phe Gln Leu Arg Asp Lys Pro Gln Arg Pro Gly Arg Asn Pro Asn Thr
1               5                   10                  15

Gly Glu Ala Ile
            20

<210> SEQ ID NO 89
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89
```

```
Phe Gln Val Arg Asp Lys Pro Pro Arg Gly Arg Asn Pro Lys Thr
1               5                   10                  15

Gly Glu Thr Ile
            20

<210> SEQ ID NO 90
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Phe Glu Val Lys Lys Arg Leu Glu Arg Val Met Val Asn Pro Ser Thr
1               5                   10                  15

Gly Leu Arg Met
            20

<210> SEQ ID NO 91
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Phe Glu Val Lys Lys Arg Leu Glu Arg Ile Met Thr Asn Pro Ala Thr
1               5                   10                  15

Gly Leu Arg Met
            20

<210> SEQ ID NO 92
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Phe Glu Ser Arg Val Arg Lys Ala Ser Val Gly Lys Ser Ile Asn Thr
1               5                   10                  15

Gly Glu Val Val
            20

<210> SEQ ID NO 93
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Phe Lys Val Gln Ala Val Lys Pro Arg Glu Ser Val Asn Val Asn Thr
1               5                   10                  15

Gly Glu Arg Val
            20
```

<210> SEQ ID NO 94
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Phe Lys Val Gln Ala Val Lys Pro Arg Glu Ser Val Asn Val Asn Thr
1               5                   10                  15

Gly Glu Arg Val
            20

<210> SEQ ID NO 95
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Phe Glu Val Arg Glu Arg Ala Ala Arg Lys Gly Arg Asn Pro Gln Thr
1               5                   10                  15

Gly Lys Glu Ile
            20

<210> SEQ ID NO 96
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Phe Lys Val Asn His Arg Ala Glu Arg Thr Gly Arg Asn Pro Gln Thr
1               5                   10                  15

Gly Lys Glu Ile
            20

<210> SEQ ID NO 97
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Phe Glu Val Arg Glu Arg Ala Ala Arg Lys Gly Arg Asn Pro Gln Thr
1               5                   10                  15

Gly Lys Glu Ile
            20

<210> SEQ ID NO 98
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 98

Phe Glu Val Arg Glu Arg Ala Ala Arg Lys Gly Arg Asn Pro Gln Thr
1               5                   10                  15

Gly Ala Glu Ile
            20

<210> SEQ ID NO 99
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 99

Phe Glu Val Arg Glu Arg Ala Ala Arg Lys Gly Arg Asn Pro Gln Thr
1               5                   10                  15

Gly Ala Glu Ile
            20

<210> SEQ ID NO 100
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 100

Phe Glu Val Arg Glu Arg Ala Ala Arg Lys Gly Arg Asn Pro Gln Thr
1               5                   10                  15

Gly Glu Glu Ile
            20

<210> SEQ ID NO 101
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 101

Phe Glu Val Arg Glu Arg Ala Ala Arg Lys Gly Arg Asn Pro Gln Thr
1               5                   10                  15

Gly Ala Glu Ile
            20

<210> SEQ ID NO 102
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 102

Phe Glu Val Arg Glu Arg Ala Glu Arg Lys Gly Arg Asn Pro Gln Thr
1               5                   10                  15

-continued

Gly Lys Glu Met
            20

<210> SEQ ID NO 103
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Phe Glu Val Arg Glu Arg Ala Ala Arg Lys Gly Arg Asn Pro Gln Thr
1               5                   10                  15

Gly Lys Glu Ile
            20

<210> SEQ ID NO 104
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Phe Glu Val Arg Glu Arg Ala Ala Arg Lys Gly Arg Asn Pro Gln Thr
1               5                   10                  15

Gly Glu Glu Ile
            20

<210> SEQ ID NO 105
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Phe Glu Val Arg Glu Arg Ala Ala Arg Lys Gly Arg Asn Pro Gln Thr
1               5                   10                  15

Gly Gln Glu Ile
            20

<210> SEQ ID NO 106
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Phe Lys Val Asn Glu Arg Ala Ala Arg Thr Gly Arg Asn Pro Gln Thr
1               5                   10                  15

Gly Ala Glu Ile
            20

<210> SEQ ID NO 107
<211> LENGTH: 20

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Phe Lys Val Asn His Arg Ser Ala Arg Thr Gly Arg Asn Pro Gln Thr
1               5                   10                  15

Gly Glu Glu Ile
            20

<210> SEQ ID NO 108
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Phe Ala Val Lys Glu Arg Ala Ala Arg Thr Gly Arg Asn Pro Gln Thr
1               5                   10                  15

Gly Lys Pro Ile
            20

<210> SEQ ID NO 109
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Phe Lys Val Asn Ala Arg Lys Ala Arg Thr Gly Arg Asn Pro Gln Thr
1               5                   10                  15

Gly Ala Glu Ile
            20

<210> SEQ ID NO 110
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Phe Ser Val Arg Thr Arg Ala Ala Arg Thr Gly Arg Asn Pro Lys Thr
1               5                   10                  15

Gly Glu Glu Ile
            20

<210> SEQ ID NO 111
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 111

Phe Ala Val Lys Glu Arg Ala Ala Arg Thr Gly Arg Asn Pro Gln Thr
1               5                   10                  15

Gly Lys Glu Ile
            20

<210> SEQ ID NO 112
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Phe Ser Val Lys Glu Arg Ala Ala Arg Met Gly Arg Asn Pro Lys Thr
1               5                   10                  15

Gly Glu Ala Ile
            20

<210> SEQ ID NO 113
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113

Phe Ala Val Ser Ala Arg Ala Ala Arg Thr Gly Arg Asn Pro Arg Thr
1               5                   10                  15

Gly Glu Thr Ile
            20

<210> SEQ ID NO 114
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Phe Cys Leu His His Arg Ser Ala Arg Ile Ala Arg Asn Pro Arg Thr
1               5                   10                  15

Gly Glu Ser Val
            20

<210> SEQ ID NO 115
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Phe Ala Thr Thr Glu Arg Pro Ala His Glu Gly Ile Asn Pro Arg Ser
1               5                   10                  15

Lys Glu Lys Ile
            20
```

<210> SEQ ID NO 116
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Tyr Ser Val Thr Glu Arg Pro Ala His Glu Gly Ile Asn Pro Ala Thr
1               5                   10                  15

Lys Gln Lys Ile
            20

<210> SEQ ID NO 117
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Asp Phe Ala Val Leu His Gly Arg Lys Asn Ala Arg Asn Pro Lys Thr
1               5                   10                  15

Gly Glu Ala Val
            20

<210> SEQ ID NO 118
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Phe Ser Val Ser Glu Arg Ala Ala Arg Lys Gly Ile Asn Pro Lys Thr
1               5                   10                  15

Lys Lys Ser Ile
            20

<210> SEQ ID NO 119
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Phe Glu Thr Ala Glu Gln Lys Gly Lys Glu Gly Lys Val Pro Gly Ser
1               5                   10                  15

Asp Lys Thr Tyr
            20

<210> SEQ ID NO 120
<211> LENGTH: 21
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 120

Ser Phe Ile Val Lys His Arg Ala Glu Lys Thr Ala Arg Asn Ile Ser
1               5                   10                  15

Lys Asn Thr Thr Ile
            20

<210> SEQ ID NO 121
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ser Phe Ile Val Lys His Arg Ala Glu Lys Thr Ala Arg Asn Ile Ser
1               5                   10                  15

Lys Asn Thr Thr Ile
            20

<210> SEQ ID NO 122
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Phe Ile Val Lys Glu Arg Ala Glu Lys Thr Ala Arg Asn Ile Ser Lys
1               5                   10                  15

Gln Thr Thr Ile
            20

<210> SEQ ID NO 123
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Phe Glu Gln Arg Arg Arg Ala Ala Arg Val Ala Arg Asn Pro Arg Thr
1               5                   10                  15

Gly Glu Thr Val
            20

<210> SEQ ID NO 124
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Phe Glu Gln Arg Arg Arg Ala Ala Arg Val Ala Arg Asn Pro Arg Thr
```

```
1               5                   10                  15

Gly Glu Thr Val
            20

<210> SEQ ID NO 125
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Phe Ser Leu His Tyr Arg Ala Pro Arg Thr Gly Arg Asn Pro Lys Thr
1               5                   10                  15

Gly Asp Lys Val
            20

<210> SEQ ID NO 126
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Phe Ser Leu His Tyr Arg Ala Pro Arg Thr Gly Arg Asn Pro Lys Thr
1               5                   10                  15

Gly Asp Lys Val
            20

<210> SEQ ID NO 127
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Phe Ser Leu His Tyr Arg Glu Pro Arg Val Gly Arg Asn Pro Lys Thr
1               5                   10                  15

Gly Asp Lys Val
            20

<210> SEQ ID NO 128
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Phe Ser Leu His Tyr Arg Ala Pro Arg Val Gly Arg Asn Pro Lys Thr
1               5                   10                  15

Gly Glu Ser Val
            20

<210> SEQ ID NO 129
```

```
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Phe Ser Leu His Cys Arg Gln Pro Arg Ile Gly Arg Asn Pro Lys Thr
1               5                   10                  15

Gly Glu Gln Val
            20

<210> SEQ ID NO 130
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Phe Asp Leu Asn His Arg Pro Ala Arg Ile Gly Arg Asn Pro Lys Thr
1               5                   10                  15

Gly Glu Arg Val
            20

<210> SEQ ID NO 131
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Phe Asp Leu Asn His Arg Pro Ala Arg Ile Gly Arg Asn Pro Lys Thr
1               5                   10                  15

Gly Glu Arg Val
            20

<210> SEQ ID NO 132
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Phe Gly Leu Asn Arg Arg Pro Ala Arg Val Gly Arg Asn Pro Lys Ser
1               5                   10                  15

Gly Glu Lys Val
            20

<210> SEQ ID NO 133
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 133

Phe Gly Leu Asn Arg Arg Pro Ala Arg Val Gly Arg Asn Pro Lys Ser
1               5                   10                  15

Gly Glu Lys Val
            20

<210> SEQ ID NO 134
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Phe Ser Leu Ser Gln Arg Ser Pro Arg Ile Gly Arg Asn Pro Lys Ser
1               5                   10                  15

Gly Glu Gln Val
            20

<210> SEQ ID NO 135
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Phe Glu Val Arg Lys Arg Lys Gly Arg Leu Asn Ala Arg Asn Pro Gln
1               5                   10                  15

Thr Gly Glu Tyr Val
            20

<210> SEQ ID NO 136
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Phe Ser Leu His His Arg Gln Pro Arg Leu Gly Arg Asn Pro Lys Thr
1               5                   10                  15

Gly Asp Ser Val
            20
```

DNABII VACCINES AND ANTIBODIES WITH ENHANCED ACTIVITY

CROSS-REFERENCE TO RELATED APPLICATIONS

This application is a National Stage Application of PCT/US2018/012235, filed Jan. 3, 2018, which claims the benefit under 35 U.S.C. § 119(e) to U.S. Provisional Application Nos. 62/455,437, filed Feb. 6, 2017; 62/453,921, filed Feb. 2, 2017; and 62/442,307, filed Jan. 4, 2017, the contents of each of which are incorporated herein by reference in their entireties.

STATEMENT OF GOVERNMENT RIGHTS

This invention was made with government support under DC011818 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created by Mar. 14, 2018, is named 106887-0910_SL.txt is 104,616 bytes in size.

TECHNICAL FIELD

The present disclosure generally relates to methods and compositions to lessen and/or cure bacterial biofilms and treat diseases or disorders associated with biofilms using one or more novel polypeptide vaccines, antibodies, antibody fragments and compositions.

BACKGROUND

At least one protein from the DNABII family of proteins is found in all known eubacteria and is naturally found outside of the bacterial cell. While the family elicits a strong innate immune response, host subjects fail to naturally produce specific protective antibody to family members as a result of infection. The DNABII protein and extracellular DNA (eDNA) contribute to the lattice structure of a "biofilm." The major problem with bacterial biofilms is the inability of the host immune system and/or antibiotics and other antimicrobials to gain access to the bacteria protected within the biofilm.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes that impede filters and orifices. Biofilm and biofilm organisms also cause corrosion of pipeline and petroleum process equipment. These problems can be manifested throughout an oil or gas production facility to the point where fouling and corrosive biofilm organisms have even been found on the surfaces of final product storage tanks.

In the home, biofilms are found in or on any surface that supports microbial growth, e.g., in drains, on food preparation surfaces, in toilets, and in swimming pools and spas. Biofilms are implicated in a wide range of water processes, both domestic and industrial. They can grow on the surface of process equipment and impede the performance of the equipment, such as degradation of heat transfer or plugging of filters and membranes. Biofilms growing on a cooling tower fill can add enough weight to cause collapse of the fill. Biofilms cause corrosion of even highly specialized stainless steels. Biofilms in a water process can degrade the value of a final product such as biofilm contamination in a paper process or the attachment of even a single cell on a silicon chip. Biofilms growing in drinking water distribution systems can harbor potential pathogenic organisms, corrosive organisms or bacteria that degrade the aesthetic quality of the water.

Biofilms also are associated with a number of difficult to treat diseases that plague animals and humans, for example, chronic non-healing wounds, including venous ulcers and diabetic foot ulcers, ear infections, sinus infections, urinary tract infections, pulmonary infections, cystic fibrosis, chronic obstructive pulmonary disease, catheter-associated infections, infections associated with implanted prostheses, and periodontal disease. Due to the pervasive nature of biofilms and the inability of the host immune system and/or antibiotics and other antimicrobials to gain access to the bacteria protected within the biofilm, a need exists in the art for compositions and methods that are effective to dissolve or disrupt biofilms in vitro and in vivo. This disclosure is directed to novel compositions and methods that serve this need.

SUMMARY

This disclosure provides novel compositions of matter that are shown to be effective in disrupting or breaking down a biofilm in vitro and in vivo. In one aspect, the composition is a recombinant polypeptide comprising, or consisting essentially of, or yet further consisting of, two or more isolated conformational tip domains of a DNABII polypeptide or a biological equivalent of one or more of the conformational tip domains. In one aspect, the amino acid sequences of the two or more tip domains are the same, or alternatively the amino acids sequences are different. Non-limiting examples of the conformational tip domains comprise, or alternatively consist essentially of, or yet further consist of the fragments identified herein as A5 and mB4, and equivalents of each thereof as well as $NPX_1T$ containing fragments of each thereof as well as those identified in the Sequence Listing, provided below. The structural orientation of the tip domains can be "head" to "tail"; "tail" to "head" and when the polypeptide comprises 3 or more tip domains, any combination of heads to tails, e.g., head-head-head; tail-head-heard; tail-head-tail, wherein the amine terminus of the wild-type sequence is the "head" and the carboxy terminus of the wild-type sequence is the "tail" of the polypeptide, and wherein the orientation of each domain sequence is retained (e.g., $NPX_1T$ sequence is unaltered in the amine to carboxy orientation).

In a further aspect, the recombinant polypeptide further comprises, or alternatively further consists essentially of, or yet further consists of a linker polypeptide that further comprises, or alternatively further consists essentially of, or yet further consists of 1 or more amino acids.

Also provided are recombinant polypeptides that comprise, or alternatively consist essentially of, or yet further consist of, between 3 and 5 conformational tip domains that can be produced by the same or different bacterial species, the amino acids sequences of which can be the same (e.g., all A5 amino acid sequences) or at least 2 or at least 3 or at least 4 or all 5 having different amino acid sequences of conformational tip domains (e.g., various combinations of A5 and mB4 and equivalents of thereof and/or $NPX_1T$ containing fragments of each thereof) wherein "$X_1$" is any amino acid or alternatively "$X_1$" is selected from the amino acids Q, R, K, S, or T. The conformational tip domains in the recombinant polypeptides can be in a linear or a branched conformation. They can further comprise a detectable and/or a purification label linked thereto. The structural orientation of the tip domains can be "head" to tail; tail to head wherein the polypeptide comprises 3 or more tip domains, any combination of head to tails, e.g., head-head-head; tail-head-heard; tail-head-tail, wherein the amine terminus of the wild-type sequence is the "head" and the carboxy terminus of the wild-type sequence is the "tail" of the polypeptide. The polyeptide units can be from 6 to about 25, or alternatively from about 10 to about 25, or alternatively from about 15 to about 23, or alternatively from about 18 to about 23, or alternatively about 20 amino acids in length. Thus the polypeptides in sum can be between about 21 to about 120 amino acids in length.

Recombinant polynucleotides encoding the recombinant polypeptides as described herein are also provided, and the recombinant polynucleotides can optionally further comprise, or alternatively consist essentially of, or yet further consist of, one or more regulatory elements operatively linked to the polynucleotide encoding the polyeptide. The polynucleotides can be contained within an expression or replication vector. In a yet further aspect, the recombinant polynucleotides can further comprise, or alternatively consist essentially of, or yet further consist of, a detectable and/or a purification label. The polynucleotides and/or vectors can be contained within a host cell, e.g., a prokaryotic or eukaryotic cell, e.g., a mammalian cell. These polynucleotides can be used in methods to prepare a recombinant polypeptide by culturing a host cell containing a polynucleotide encoding such under conditions that favor expression of the polynucleotide. In one aspect, the recombinant polypeptide is isolated from the cell or the cell culture medium.

Applicant also provides antibodies that bind the recombinant polypeptides as described herein, or an antigen binding fragments of the antibodies. The antibodies or the antigen binding fragments can be characterized in that they bind a DNABII polypeptide and/or prevent formation of, or disrupt a biofilm. Non-limiting examples of the antibodies are selected from the group of a monoclonal antibody, an isolated polyclonal antibody, a bispecific antibody, a human antibody, a humanized antibody, a chimeric antibody or a primatized antibody. The isolated polyclonal antibodies can be from any appropriate species, e.g., mammalian polyclonal antibodies, e.g., a rabbit polyclonal antibody, a murine polyclonal antibody, a sheep polyclonal antibody, a canine polyclonal antibody, or a human polyclonal antibody.

Non-limiting examples of antigen binding fragments are Fv antibody fragment or a Fab antibody fragment.

In one aspect, the antibodies and/or antibody fragments of this disclosure bind an epitope on a DNABII protein that is conserved across bacterial species, e.g., they disrupt a biofilm derived from at least two bacterial species including both Gram positive and Gram negative species. Non-limiting examples of a bacterial DNABII protein is *Staphylococcus aureus* DNABII or a fragment thereof, and optionally, wherein the fragment of *Staphylococcus aureus* DNABII comprises a beta hairpin conformation. Non-limiting examples of at least two bacterial species include for example, *S. aureus, P. aeruginosa* and *K. pneumonia*.

The antibodies or antigen binding fragments as described herein can optionally further comprise, or consist essentially of, or yet further consist of a detectable and/or a purification label.

Also provided herein are methods to obtain antibodies as described herein that immunoreactive with a DNABII polypeptide or to generate B cells that secrete antibodies immunoreactive with a DNABII polypeptide. This method comprises, or alternatively consists essentially of, or yet further consists of administering an effective amount of a recombinant polypeptide or composition containing such to a subject and subsequently recovering antibodies or recovering B cells from the subject. The subject can be an animal, e.g., a mammal such as a human. The method can further comprise screening the B cells recovered from the subject for secretion of an antibody with high affinity for a DNABII polypeptide, thus identifying B cells that secrete antibodies immunoreactive with a DNABII polypeptides, and optionally isolating DNA or mRNA encoding said antibodies from the B cells.

Also provided are polynucleotides encoding the antibodies or antigen binding fragments as described herein, that optionally can further comprise, or alternatively consisting essentially of, or yet further consist of, a detectable and/or a purification label. The polynucleotides as described herein can be contained with an expression or replication vector and can further comprise one or more regulatory elements operatively linked to the polynucleotides to drive expression and/or replication of the polynucleotide. The polynucleotides and/or vectors can be contained within a host cell, e.g., a prokaryotic or eukaryotic cell, e.g., a mammalian cell. In one aspect, these embodiments can be used in a method to prepare a polypeptide having the amino acid sequence of an antibody or antigen binding fragment of an antibody, the method comprising, or alternatively consisting essentially of, or yet further consisting of, culturing a host cell containing a polynucleotide encoding such under conditions that favor expression of the polynucleotide. In a further aspect, the polypeptide produced by the vector and/or host cell is isolated from the cell and/or the media in which the cells are cultured.

Compositions comprising, or alternatively consisting essentially of, or yet further consisting of a carrier and one or more of: a recombinant polypeptide, a polynucleotide, a vector, an antibody, a host cell, and/or the antigen binding fragments as described herein are also provided. The compositions can comprise polypeptides having a plurality of compositions having different constructs, e.g., the polypeptides can have different or the same primary amino acid sequence and/or confirmation from each other. The compositions can optionally further comprise a preservative and/or stabilizer, and further optionally at least one antibiotic or an additional active ingredient.

Applicant's disclosure also provides vaccine compositions that comprise, or alternatively consist essentially of, or yet further consist of, an effective amount of a recombinant polypeptide and a pharmaceutically acceptable carrier. The compositions can further comprise an adjuvant and optionally a preservative and/or a stabilizer and further optionally at least one antibiotic or an additional active ingredient. As noted above, in one aspect, the vaccine composition can comprise an effective amount of a plurality of recombinant polypeptides wherein two or more different recombinant polypeptides are within the same vaccine composition in varying ratios to each other. The vaccine compositions can be formulated for human or animal use. In a further aspect, the composition is formulated for pediatric administration.

Also provided are compositions comprising a plurality of antibodies or antigen binding fragments that may be the same or different from each other, e.g., two or more Fab antibody fragments of the antibodies as described herein. In one aspect, the two or more Fab fragments within the plurality are different from each other. The compositions can further comprise a carrier, optionally a pharmaceutically acceptable carrier and optionally at least one antibiotic or an additional active ingredient. The compositions can also comprise a preservative and/or stabilizer. These compositions can comprise a therapeutically effective amount and be formulated for human or animal use. In a further aspect, the composition comprises an effective amount for pediatric administration and is optionally formulated for pediatric administration.

The compositions as described herein are useful diagnostically, therapeutically and ex vivo. In one aspect the recombinant polypeptides, antibodies, antigen binding fragments thereof, compositions and/or vaccines are used in a method to prevent formation of or to disrupt a biofilm associated with an industrial process, the method comprising, or alternatively consisting essentially of, or yet further consisting of treating or contacting a surface susceptible to, or containing a biofilm, with an effective amount of one or more of a recombinant polypeptide, an antibody, a vaccine, a composition, and/or the antigen binding fragment as described herein.

Further provided are methods to disrupt or prevent the formation of a biofilm in a subject in need thereof, comprising, or alternatively consisting essentially of, or yet further consists of, administering to the subject an effective amount of one or more of a recombinant polypeptide, an antibody, an antibody fragment, a vaccine, and/or a composition, as described herein. In one aspect, the subject is diagnosed as harboring a biofilm or a bacterial infection associated with a biofilm prior to use of the method.

Also provided are methods to treat a condition associated with a biofilm in a subject in need thereof, the method comprising or alternatively consisting essentially of, or yet further consisting of, administering to the subject an effective amount of one or more of a recombinant polypeptide, a composition, a vaccine, an antibody, and/or the antigen binding fragment as described herein. Non-limiting examples of condition include without limitation, chronic non-healing wounds, including venous ulcers and diabetic foot ulcers, ear infections, sinus infections, urinary tract infections, pulmonary infections, cystic fibrosis, chronic obstructive pulmonary disease, catheter-associated infections, infections associated with implanted prostheses, and periodontal disease. In one aspect, the subject is diagnosed as harboring a biofilm prior to administration of the method.

Also provided are methods to induce an anti-inflammatory cytokine response in a subject in need thereof, the method comprising, or alternatively consisting essentially of, or yet further consisting of, administering to the subject an effective amount of one or more of a recombinant polypeptide, an antibody, and/or the antigen binding fragment as disclosed herein. In one aspect, the anti-inflammatory cytokine response comprises one or more of inducing or enhancing the production of IL-4, IL-10, or IL-13. In a yet further aspect, the method further comprising assaying for the level of anti-inflammatory cytokines, prior to or subsequent to administration. In one aspect, the subject is suffering from a condition of the group of: chronic non-healing wounds, including venous ulcers and diabetic foot ulcers, ear infections, sinus infections, urinary tract infections, pulmonary infections, cystic fibrosis, chronic obstructive pulmonary disease, catheter-associated infections, infections associated with implanted prostheses, or periodontal disease.

As noted above, in some aspects, it may be desirable to detect the presence of a biofilm and/or an organism known to produce a biofilm in the subject prior to administration. In one aspect, the detecting is by a method comprising contacting a sample isolated from the patient suspected of containing the biofilm or infection with an antibody that recognizes and bind a component of the biofilm and detecting any complex formed between the biofilm in the sample and the antibody.

Further provided are non-physiological surfaces coated with one or more of the composition, the recombinant polypeptide, the isolated antibody, and/or the antigen binding fragment as described herein, and optionally, wherein the surface is in an industrial setting. Similar to the therapeutic methods described above, it may be desirable to detect the presence of a biofilm and/or an organism known to produce a biofilm prior to administration or contacting the surface. In one aspect, the detecting is by a method comprising contacting a sample isolated from the surface suspected of containing the biofilm with an antibody that recognizes and bind a component of the biofilm and detecting any complex formed between the biofilm in the sample and the antibody.

Also provided are methods to obtain antisera effective to disrupt biofilm, comprising immunizing a subject with a recombinant polypeptide and/or vaccine compositions as described herein, and recovering antiserum from the subject, and optionally isolating polyclonal antiserum or monoclonal antibodies from the subject. The antisera can be used to treat or disrupt a biofilm or treat a biofilm-related condition in a subject, by administering an effective amount of the antisera to a subject in need thereof.

Kits are further provided for diagnostic or therapeutic use. The components of the kit will vary with the intended use. Non-limiting examples of the components include one or more composition, polypeptide, polynucleotide, antibody, antibody fragment, and/or vaccine as described herein. In one aspect the kit also contains instructions for the diagnostic, therapeutic or industrial use of the kit components.

---

PARTIAL SEQUENCE LISTING

SEQ ID NO. 1: Full Length Wild type (wt) 86-028NP *Haemophilus influenzae* IhfA;
Genbank Accession No.: AAX88425.1, last accessed Mar. 21, 2011:
MATITKLDIIEYLSDKYHLSKQDTKNVVENFLEEIRLSLESGQDVKLSGFGNFELRDK
SSRPGRNPKTGDVVPVSARRVVITKPGQKLRARVEKIK.

SEQ ID NO. 2: Full Length Wild type (wt) 86-028NP *Haemophilus influenzae* IhfB;
Genbank Accession No.: AAX88699.1, last accessed May 13, 2015:
MTKSELMEKLSAKQPTLSAKEIENMVKDILEFISQSLENGDRVEVRGFGSFSLHERQP
RLGRNPKTGDSVNLSAKSVPYFKAGKELKARV DVQA.

PARTIAL SEQUENCE LISTING

SEQ ID NO. 3: Full Length wt 86-028NP *Haemophilus influenzae* HU, Genbank Accession
No.: YP_248142.1, last accessed Mar. 21, 2011:
MRFVTIFINHAFNSSQVRLSFAQFLRQIRKDTFKESNFLFNRRYKFMNKTDLIDAIAN
AAELNKKQAKAALEATLDAITASLKEGEPVQLIGFGTFKVNERAARTGRNPQTGAEI
QIAASKVPAFVSGKALKDAIK.

SEQ ID NO. 4: Full Length wt R2846 *Haemophilus influenzae* IhfA, Genbank Accession
No.: ADO6375, last accessed Mar. 21, 2011:
MATITKLDIIEYLSDKYHLSKQDTKNVVENFLEEIRLSLESGQDVKLSGFGNFELRDK
SSRPGRNPKTGDVVPVSARRVVTFKPGQKLRARVEKTK.

SEQ ID NO. 5: Full Length wt Rd *Haemophilus influenzae* IhfA; Genbank Accession No.:
AAC22959.1, last accessed Mar. 21, 2011:
MATITKLDIIEYLSDKYHLSKQDTKNVVENFLEEIRLSLESGQDVKLSGFGNFELRDK
SSRPGRNPKTGDVVPVSARRVVTFKPGQKLRARVEKTK.

SEQ ID NO. 6: Full Length wt *E. coli* K12 IhfA; Genbank Accession No.: AAC74782.1,
last accessed Mar. 21, 2011:
MALTKAEMSEYLFDKLGLSKRDAKELVELFFEEIRRALENGEQVKLSGFGNFDLRDK
NQRPGRNPKTGEDIPITARRVVTFRPGQKLKSRVENASPKDE; DNAGenbank No.
NC_000913.

SEQ ID NO. 7: Full Length wt *E. coli* K12 IhfB; Genbank Accession No.: BAA35656,
last accessed May 19, 2015:
MTKSELIERLATQQSHIPAKTVEDAVKEMLEHMASTLAQGERIEIRGFGSFSLHYRAP
RTGRNPKTGDKVELEGKYVPHFKPGKELRDRANIYG.

SEQ ID NO. 8: *E. coli* hupA, Genbank Accession No.: AP_003818, Last accessed Mar. 21,
2011:
MNKTQLIDVIAEKAELSKTQAKAALESTLAAITESLKEGDAVQLVGFGTFKVNHRAE
RTGRNPQTGKEIKIAAANVPAFVSGKALKDAVK.

SEQ ID NO. 9: *E. coli* hupB, Genbank Accession No.: AP_001090.1, Last accessed Mar.
21, 2011:
MNKSQLIDKIAAGADISKAAAGRALDAIIASVTESLKEGDDVALVGFGTFAVKERAA
RTGRNPQTGKEIAAAKVPSFRAGKALKDAVN.

SEQ ID NO. 10: Full Length wt *P. aeruginosa* PA01 IhfA; Genbank Accession No.:
AAG06126.1, last accessed Mar. 21, 2011:
MGALTKAEIAERLYEELGLNKREAKELVELFFEEIRQALEHNEQVKLSGFGNFDLRD
KRQRPGRNPKTGEEIPITARRVVTFRPGQKLKARVEAYAGTKS.

SEQ ID NO. 11: Full Length wt *P. aeruginosa* PA01 IhfB; Genbank Accession No.:
AAF72950.1, last accessed May 19, 2015:
MTKSELIERIVTHQGQLSAKDVELAIKTMLEQMSQALATGDRIEIRGFGSFSLHYRAP
RVGRNPKTGESVRLDGKFVPHFKPGKELRDRVNEPE.

SEQ ID NO. 12: *Haemophilus influenzae* IhfA, A-3 fragment:
FLEEIRLSLESGQDVKLSGF.

SEQ ID NO. 13: *Haemophilus influenzae* IhfA, A5 fragment:
RPGRNPKTGDVVPVSARRVV.

SEQ ID NO. 14: *Haemophilus influenzae* HU, A5 fragment: RTGRNPQTGAEIQIAASKVP.

SEQ ID NO. 15: *Haemophilus influenzae* IhfB, B2 fragment: TLSAKEIENMVKDILEFISQ.

SEQ ID NO. 16: *Haemophilus influenzae* IhfB, B4 fragment:
RGFGSFSLHHRQPRLGRNPK.

SEQ ID NO. 17: *Haemophilus influenzae* IhfB, modified B4 (mB4) fragment:
FSLHHRQPRLGRNPKTGDSV.

SEQ ID NO. 18: *Haemophilus influenzae* IhfA, A-1 fragment:
MATITKLDIIEYLSDKYHLS.

SEQ ID NO. 19: *Haemophilus influenzae* IhfA, A2 fragment:
KYHLSKQDTKNVVENFLEEI.

SEQ ID NO. 20: *Haemophilus influenzae* IhfA, A4 fragment:
KLSGFGNFELRDKSSRPGRN.

SEQ ID NO. 21: *Haemophilus influenzae* IhfA, A6 fragment:
ARRVVTFKPGQKLRARVEKTK.

SEQ ID NO. 22: *Haemophilus influenzae* IhfB, B1 fragment:
MTKSELMEKLSAKQPTLSAK.

PARTIAL SEQUENCE LISTING

SEQ ID NO. 23: *Haemophilus influenzae* IhfB, B3 fragment:
EFISQSLENGDRVEVRGFGS.

SEQ ID NO. 24: *Haemophilus influenzae* IhfB, B5 fragment:
GRNPKTGDSVNLSAKSVPYF.

SEQ ID NO. 25: *Haemophilus influenzae* IhfB, B6 fragment:
SVPYFKAGKELKARVDVQA.

SEQ ID NO. 26: *Haemophilus influenzae* IhfA, A conformational tip domain:
NFELRDKSSRPGRNPKTGDVV.

SEQ ID NO. 27: *Haemophilus influenzae* IhfB, B conformational tip domain:
SLHHRQPRLGRNPKTGDSVNL.

SEQ ID NO. 28 *Haemophilus influenzae* HU, fragment:
MNKTDLIDAIANAAELNKKQAK.

SEQ ID NO. 29 *Haemophilus influenzae* HU, fragment: KKQAKAALEATLDAITASLKEG.

SEQ ID NO. 30 *Haemophilus influenzae* HU, fragment: SLKEGEPVQLIGFGTFKVNERA.

SEQ ID NO. 31 *Haemophilus influenzae* HU, fragment: VNERAARTGRNPQTGAEIQIAA.

SEQ ID NO. 32 *Haemophilus influenzae* HU, fragment: IQIAASKVPAFVSGKALKDAIK.

SEQ ID NO. 33: Human IgD constant region, Uniprot: P01880:
APTKAPDVFPIISGCRHPKDNSPVVLACLITGYHPTSVTVTWYMGTQSQPQRTFPEIQ
RRDSYYMTSSQLSTPLQQWRQGEYKCVVQHTASKSKKEIFRWPESPKAQASSVPTA
QPQAEGSLAKATTAPATTRNTGRGGEEKKKEKEKEEQEERETKTPECPSHTQPLGVY
LLTPAVQDLWLRDKATFTCFVVGSDLKDAHLTWEVAGKVPTGGVEEGLLERHSNG
SQSQHSRLTLPRSLWNAGTSVTCTLNHPSLPPQRLMALREPAAQAPVKLSLNLLASS
DPPEAASWLLCEVSGFSPPNILLMWLEDQREVNTSGFAPARPPPQPGSTTFWAWSVL
RVPAPPSPQPATYTCVVSHEDSRTLLNASRSLEVSYVTDHGPMK.

SEQ ID NO. 34: Human IgG1 constant region, Uniprot: P01857:
ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK.

SEQ ID NO. 35: Human IgG2 constant region, Uniprot: P01859:
ASTKGPSVFPLAPCSRSTSESTAALGCLVKDYFPEPVTVSWNSGALTSGVHTFPAVLQ
SSGLYSLSSVVTVPSSNFGTQTYTCNVDHKPSNTKVDKTVERKCCVECPPCPAPPVA
GPSVFLFPPKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTKGQPREPQVY
TLPPSREEMTKNQVSLTCLVKGFYPSDISVEWESNGQPENNYKTTPPMLDSDGSFFL
YSKLTVDKSRWQQGNVFSCSVMHEALHNHYTQKSLSLSPGK.

SEQ ID NO. 36: Human IgG3 constant region, Uniprot: P01860:
ASTKGPSVFPLAPCSRSTSGGTAALGCLVKDYFPEPVTVSWNSGALTSGVHTFPAVL
QSSGLYSLSSVVTVPSSSLGTQTYTCNVNHKPSNTKVDKRVELKTPLGDTTHTCPRC
PEPKSCDTPPPCPRCPEPKSCDTPPPCPRCPEPKSCDTPPPCPRCPAPELLGGPSVFLFPP
KPKDTLMISRTPEVTCVVVDVSHEDPEVQFKWYVDGVEVHNAKTKPREEQYNSTFR
VVSVLTVLHQDWLNGKEYKCKVSNKALPAPIEKTISKTKGQPREPQVYTLPPSREEM
TKNQVSLTCLVKGFYPSDIAVEWESSGQPENNYNTTPPMLDSDGSFFLYSKLTVDKS
RWQQGNIFSCSVMHEALHNRFTQKSLSLSPGK.

SEQ ID NO. 37: Human IgM constant region, Uniprot: P01871:
GSASAPTLFPLVSCENSPSDTSSVAVGCLAQDFLPDSITLSWKYKNNSDISSTRGFPSV
LRGGKYAATSQVLLPSKDVMQGTDEHVVCKVQHPNGNKEKNVPLPVIAELPPKVSV
FVPPRDGFFGNPRKSKLICQATGFSPRQIQVSWLREGKQVGSGVTTDQVQAEAKESG
PTTYKVTSTLTIKESDWLGQSMFTCRVDHRGLTFQQNASSMCVPDQDTAIRVFAIPPS
FASIFLTKSTKLTCLVTDLTTYDSVTISWTRQNGEAVKTHTNISESHPNATFSAVGEAS
ICEDDWNSGERFTCTVTHTDLPSPLKQTISRPKGVALHRPDVYLLPPAREQLNLRESA
TITCLVTGFSPADVFVQWMQRGQPLSPEKYVTSAPMPEPQAPGRYFAHSILTVSEEE
WNTGETYTCVAHEALPNRVTERTVDKSTGKPTLYNVSLVMSDTAGTCY.

SEQ ID NO. 38: Human IgG4 constant region, Uniprot: P01861:
ASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPSCPAPEFLG
GPSVFLFPPKPKDTLMISRTPEVTCVVVDVSQEDPEVQFNWYVDGVEVHNAKTKPR

PARTIAL SEQUENCE LISTING

EEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLGK.

SEQ ID NO. 39: Human IgA1 constant region, Uniprot: P01876:
ASPTSPKVFPLSLCSTQPDGNVVIACLVQGFFPQEPLSVTWSESGQGVTARNFPPSQD
ASGDLYTTSSQLTLPATQCLAGKSVTCHVKHYTNPSQDVTVPCPVPSTPPTPSPSTPP
TPSPSCCHPRLSLHRPALEDLLLGSEANLTCTLTGLRDASGVTFTWTPSSGKSAVQGP
PERDLCGCYSVSSVLPGCAEPWNHGKTFTCTAAYPESKTPLTATLSKSGNTFRPEVH
LLPPPSEELALNELVTLTCLARGFSPKDVLVRWLQGSQELPREKYLTWASRQEPSQG
TTTFAVTSILRVAAEDWKKGDTFSCMVGHEALPLAFTQKTIDRLAGKPTHVNVSVV
MAEVDGTCY.

SEQ ID NO. 40: Human IgA2 constant region, Uniprot: P01877:
ASPTSPKVFPLSLDSTPQDGNVVVACLVQGFFPQEPLSVTWSESGQNVTARNFPPSQD
ASGDLYTTSSQLTLPATQCPDGKSVTCHVKHYTNPSQDVTVPCPVPPPPCCHPRLSL
HRPALEDLLLGSEANLTCTLTGLRDASGATFTWTPSSGKSAVQGPPERDLCGCYSVS
SVLPGCAQPWNHGETFTCTAAHPELKTPLTANITKSGNTFRPEVHLLPPPSEELALNE
LVTLTCLARGFSPKDVLVRWLQGSQELPREKYLTWASRQEPSQGTTTFAVTSILRVA
AEDWKKGDTFSCMVGHEALPLAFTQKTIDRMAGKPTHVNVSVVMAEVDGTCY.

SEQ ID NO. 41: Human Ig kappa constant region, Uniprot: P01834:
TVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC.

SEQ ID NO. 42: Non-limiting exemplary linker: GPSLKL.

SEQ ID NO. 43: Non-limiting exemplary linker: GGG.

SEQ ID NO. 44: Non-limiting exemplary linker: GPSL.

SEQ ID NO. 45: Non-limiting exemplary linker: GPS.

SEQ ID NO. 46: Non-limiting exemplary linker: PSLK.

SEQ ID NO. 47: Non-limiting exemplary linker: GPSLK.

SEQ ID NO. 48: Non-limiting exemplary linker: SLKL.

SEQ ID NO. 49: Non-limiting exemplary linker: GGSGGS.

SEQ ID NO: 50: Non-limiting exemplary IhfA5-mIhfB4$_{NTHI}$ chimer recombinant
polypeptide sequence:
RPGRNPKTGDVVPVSARRVVGPSLFSLHHRQPRLGRNPKTGDSV SEQ ID NO: 51: Non-limiting exemplary IhfA5-mIhfB4$_{NTHI}$ chimer recombinant
polypeptide sequence having a variable linker:
RPGRNPKTGDVVPVSARRVV-X-FSLHHRQPRLGRNPKTGDSV
wherein "X" is an amino acid linker sequence comprising between 1 to 20 amino acids.

SEQ ID NO: 52: Non-limiting exemplary mIhfB4$_{NTHI}$-mIhfB4$_{NTHI}$-IhfA5 chimer
recombinant polypeptide polypeptide sequence:
FSLHHRQPRLGRNPKTGDSV-X-FSLHHRQPRLGRNPKTGDSV-X-
RPGRNPKTGDVVPVSARRVV
wherein "X" is an amino acid linker sequence comprising between 1 to 20 amino acids.

SEQ ID NO: 53: Non-limiting exemplary mIhfB4$_{NTHI}$-IhfA5-mIhfB4$_{NTHI}$ chimer
recombinant polypeptide sequence:
FSLHHRQPRLGRNPKTGDSV-X-RPGRNPKTGDVVPVSARRVV-X-
FSLHHRQPRLGRNPKTGDSV
wherein "X" is an amino acid linker sequence comprising between 1 to 20 amino acids.

SEQ ID NO: 54: Non-limiting exemplary IhfA5-mIhfB4$_{NTHI}$-mIhfB4$_{NTHI}$ chimer
recombinant polypeptide sequence:
RPGRNPKTGDVVPVSARRVV-X-FSLHHRQPRLGRNPKTGDSV-X-
FSLHHRQPRLGRNPKTGDSV
wherein "X" is an amino acid linker sequence comprising between 1 to 20 amino acids.

SEQ ID NO: 55: Non-limiting exemplary IhfA5-IhfA5-mIhfB4$_{NTHI}$ chimer recombinant
polypeptide sequence:
RPGRNPKTGDVVPVSARRVV-X-RPGRNPKTGDVVPVSARRVV-X-
FSLHHRQPRLGRNPKTGDSV
wherein "X" is an amino acid linker sequence comprising between 1 to 20 amino acids.

SEQ ID NO: 56: Non-limiting exemplary IhfA5-mIhfB4$_{NTHI}$-IhfA5 chimer recombinant
polypeptide sequence:
RPGRNPKTGDVVPVSARRVV-X-FSLHHRQPRLGRNPKTGDSV-X-

PARTIAL SEQUENCE LISTING

RPGRNPKTGDVVPVSARRVV
wherein "X" is an amino acid linker sequence comprising between 1 to 20 amino acids.

SEQ ID NO: 57: Non-limiting exemplary mIhfB4$_{NTHI}$-IhfA5-IhfA5-chimer recombinant polypeptide sequence:
FSLHHRQPRLGRNPKTGDSV-X-RPGRNPKTGDVVPVSARRVV-X-
RPGRNPKTGDVVPVSARRVV
wherein "X" is an amino acid linker sequence comprising between 1 to 20 amino acids.

SEQ ID NO: 58: Non-limiting exemplary mffif134$_{NTHI}$-mIhfB4$_{NTHI}$-IhfA5-IhfA5-chimer recombinant polypeptide sequence:
FSLHHRQPRLGRNPKTGDSV-X-FSLHHRQPRLGRNPKTGDSV-X-
RPGRNPKTGDVVPVSARRVV-X-RPGRNPKTGDVVPVSARRVV
wherein "X" is an amino acid linker sequence comprising between 1 to 20 amino acids.

SEQ ID NO: 59: Non-limiting exemplary mIhfB4$_{NTHI}$-IhfA5-mIhfB4$_{NTHI}$-IhfA5-chimer recombinant polypeptide sequence:
FSLHHRQPRLGRNPKTGDSV-X-RPGRNPKTGDVVPVSARRVV-X-
FSLHHRQPRLGRNPKTGDSV-X-RPGRNPKTGDVVPVSARRVV
wherein "X" is an amino acid linker sequence comprising between 1 to 20 amino acids.

SEQ ID NO: 60: Non-limiting exemplary IhfA5-mIhfB4$_{NTHI}$-IhfA5-mIhfB4$_{NTHI}$-chimer recombinant polypeptide sequence:
RPGRNPKTGDVVPVSARRVV-X-FSLHHRQPRLGRNPKTGDSV-X-
RPGRNPKTGDVVPVSARRVV-X-FSLHHRQPRLGRNPKTGDSV
wherein "X" is an amino acid linker sequence comprising between 1 to 20 amino acids.

SEQ ID NO: 61: Non-limiting exemplary mIhfB4$_{NTHI}$-IhfA5-IhfA5-mIhfB4$_{NTHI}$-chimer recombinant polypeptide sequence:
FSLHHRQPRLGRNPKTGDSV-X-RPGRNPKTGDVVPVSARRVV-X-
RPGRNPKTGDVVPVSARRVV-X-FSLHHRQPRLGRNPKTGDSV
wherein "X" is an amino acid linker sequence comprising between 1 to 20 amino acids.

SEQ ID NO: 62: Non-limiting exemplary IhfA5-mIhfB4$_{NTHI}$-mIhfB4$_{NTHI}$-IhfA5-chimer recombinant polypeptide sequence:
RPGRNPKTGDVVPVSARRVV-X-FSLHHRQPRLGRNPKTGDSV-X-
FSLHHRQPRLGRNPKTGDSV-X-RPGRNPKTGDVVPVSARRVV
wherein "X" is an amino acid linker sequence comprising between1 to 20 amino acids.

SEQ ID NO: 63: Non-limiting exemplary IhfA5-IhfA5-mIhfB4$_{NTHI}$-mIhfB4$_{NTHI}$-chimer recombinant polypeptide sequence:
RPGRNPKTGDVVPVSARRVV-X-RPGRNPKTGDVVPVSARRVV-X-
FSLHHRQPRLGRNPKTGDSV-X-FSLHHRQPRLGRNPKTGDSV
wherein "X" is an amino acid linker sequence comprising between 1 to 20 amino acids.

SEQ ID NO: 64: Non-limiting exemplary IhfA5-mIhfB4$_{NTHI}$ chimer recombinant polypeptide sequence having a variable linker:
RPGRNPX$_1$TGDVVPVSARRVV-X-FSLHHRQPRLGRNPX$_1$TGDSV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 65: Non-limiting exemplary mIhfB4$_{NTHI}$-mIhfB4$_{NTHI}$-IhfA5 chimer recombinant polypeptide polypeptide sequence:
FSLHHRQPRLGRNPX$_1$TGDSV-X-FSLHHRQPRLGRNPX$_1$TGDSV-X-
RPGRNPX$_1$TGDVVPVSARRVV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 66: Non-limiting exemplary mIhfB4$_{NTHI}$-IhfA5-mIhfB4$_{NTHI}$chimer recombinant polypeptide sequence:
FSLHHRQPRLGRNPX$_1$TGDSV-X-RPGRNPX$_1$TGDVVPV SARRVV-X-
FSLHHRQPRLGRNPX$_1$TGDSV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 67: Non-limiting exemplary IhfA5-mIhfB4$_{NTHI}$-mIhfB4$_{NTHI}$ chimer recombinant polypeptide sequence:
RPGRNPX$_1$TGDVVPVSARRVV-X-FSLHHRQPRLGRNPX$_1$TGDSV-X-
FSLHHRQPRLGRNPX$_1$TGDSV
wherein "X" is an amino acid linker sequence comprising between 1 to 20 amino acids; and
wherein "X$_1$" is any amino acid or alternatively "X$_1$" is selected from the amino acids Q, R, K, S, or T.

PARTIAL SEQUENCE LISTING

SEQ ID NO: 68: Non-limiting exemplary IhfA5-IhfA5-mIhfB4$_{NTHI}$ chimer recombinant polypeptide sequence:
RPGRNPX$_1$TGDVVPVSARRVV-X-RPGRNPX$_1$TGDVVPVSARRVV-X-
FSLHHRQPRLGRNPX$_1$TGDSV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 69: Non-limiting exemplary IhfA5-mIhfB4$_{NTHI}$-IhfA5 chimer recombinant polypeptide sequence:
RPGRNPX$_1$TGDVVPVSARRVV-X-FSLHHRQPRLGRNPX$_1$TGDSV-X-
RPGRNPX$_1$TGDVVPVSARRVV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 70: Non-limiting exemplary mIhfB4$_{NTHI}$-IhfA5-IhfA5-chimer recombinant polypeptide sequence:
FSLHHRQPRLGRNPX$_1$TGDSV-X-RPGRNPX$_1$TGDVVPVSARRVV-X-
RPGRNPX$_1$TGDVVPVSARRVV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 71: Non-limiting exemplary mIhfB4$_{NTHI}$-mIhfB4$_{NTHI}$-IhfA5-IhfA5-chimer recombinant polypeptide sequence:
FSLHHRQPRLGRNPX$_1$TGDSV-X-FSLHHRQPRLGRNPX$_1$TGDSV-X-
RPGRNPX$_1$TGDVVPVSARRVV-X-RPGRNPX$_1$TGDVVPVSARRVV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 72: Non-limiting exemplary mIhfB4$_{NTHI}$-IhfA5-mIhfB4$_{NTHI}$-IhfA5-chimer recombinant polypeptide sequence:
FSLHHRQPRLGRNPX$_1$TGDSV-X-RPGRNPX$_1$TGDVVPVSARRVV-X-
FSLHHRQPRLGRNPX$_1$TGDSV-X-RPGRNPX$_1$TGDVVPVSARRVV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 73: Non-limiting exemplary IhfA5-mIhfB4$_{NTHI}$-IhfA5-mIhfB4$_{NTHI}$-chimer recombinant polypeptide sequence:
RPGRNPX$_1$TGDVVPVSARRVV-X-FSLHHRQPRLGRNPX$_1$TGDSV-X-
RPGRNPX$_1$TGDVVPVSARRVV-X-FSLHHRQPRLGRNPX$_1$TGDSV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 74: Non-limiting exemplary mIhfB4$_{NTHI}$-IhfA5-IhfA5-mIhfB4$_{NTHI}$-chimer recombinant polypeptide sequence:
FSLHHRQPRLGRNPX$_1$TGDSV-X-RPGRNPX$_1$TGDVVPVSARRVV-X-RPGR**NP
X$_1$TGDVVPVSARRVV-X-FSLHHRQPRLGRNPX$_1$T**GDSV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 75: Non-limiting exemplary IhfA5-mIhfB4$_{NTHI}$-mIhfB4$_{NTHI}$-IhfA5-chimer recombinant polypeptide sequence:
RPGRNPX$_1$TGDVVPVSARRVV-X-FSLHHRQPRLGRNPX$_1$TGDSV-X-
FSLHHRQPRLGRNPX$_1$TGDSV-X-RPGRNPX$_1$TGDVVPVSARRVV
wherein "X" is an amino acid linker sequence comprising between1 to 20 amino acids; and
wherein "X$_1$" is any amino acid or alternatively "X$_1$" is selected from the amino acids Q, R, K, S, or T.

SEQ ID NO: 76: Non-limiting exemplary IhfA5-IhfA5-mIhfB4$_{NTHI}$-mIhfB4$_{NTHI}$-chimer recombinant polypeptide sequence:
RPGRNPX$_1$TGDVVPVSARRVV-X-RPGRNPX$_1$TGDVVPVSARRVV-X-
FSLHHRQPRLGRNPX$_1$TGDSV-X-FSLHHRQPRLGRNPX$_1$TGDSV
wherein "X" is an amino acid linker sequence comprising between 1 to 20 amino acids; and
wherein "X$_1$" is any amino acid or alternatively "X$_1$" is selected from the amino acids Q, R, K, S, or T.

SEQ ID NO: 77: Non-limiting exemplary equivalent recombinant polypeptide sequence:
DKSSRPGRNPX$_1$TGDVVAASARR,wherein "X$_1$" is any amino acid or alternatively "X$_1$" is
selected from the amino acids Q, R, K, S, or T.

PARTIAL SEQUENCE LISTING

SEQ ID NO: 78: Non-limiting exemplary equivalent recombinant polypeptide sequence, E. coli K12-MG1655 HimA fragment: FDLRDKNQRPGRNPKTGEDI SEQ ID NO: 79: Non-limiting exemplary equivalent recombinant polypeptide sequence, Salmonella enteric serovar typhi CT18 HimA fragment: FDLRDKNQRPGRNPKTGEDI SEQ ID NO: 80: Non-limiting exemplary equivalent recombinant polypeptide sequence, V. cholera El Toz N16961 HimA fragment: FDLRDKNERPGRNPKTGEDI SEQ ID NO: 81: Non-limiting exemplary equivalent recombinant polypeptide sequence, P. aeruginosa HimA fragment: FDLRDKRQRPGRNPKTGEEI SEQ ID NO: 82: Non-limiting exemplary equivalent recombinant polypeptide sequence, H. influenzae KW20 Rd HimA fragment: FELRDKSSRPGRNPKTGDVV SEQ ID NO: 83: Non-limiting exemplary equivalent recombinant polypeptide sequence, Aggregatibacter actinomycetemcomitans D11S-1 IHFalpha fragment: FELRDKASRPGRNPKTGESV SEQ ID NO: 84: Non-limiting exemplary equivalent recombinant polypeptide sequence, Moraxella catarrhalis RH4 HimA fragment: FELKDKKPRPGRNPKTGESV SEQ ID NO: 85: Non-limiting exemplary equivalent recombinant polypeptide sequence, N. gonorrhoeae FA1090 (Oklahoma) IHFalpha fragment: FQLRDKPQRPGRNPKTGEEV SEQ ID NO: 86: Non-limiting exemplary equivalent recombinant polypeptide sequence, N. meningitides MC5B HimA fragment: FQLRDKPQRPGRNPKTGEEV SEQ ID NO: 87: Non-limiting exemplary equivalent recombinant polypeptide sequence, Burkholderia cenocepacia HI2424 IHFA fragment: FQLRDKPQRPGRNPKTGEAI SEQ ID NO: 88: Non-limiting exemplary equivalent recombinant polypeptide sequence, Burkholderia pseudomallei 668 IHFA fragment: FQLRDKPQRPGRNPNTGEAI SEQ ID NO: 89: Non-limiting exemplary equivalent recombinant polypeptide sequence, Bordetella pertusis Tohama 1 IhfA fragment: FQVRDKPPRPGRNPKTGETI SEQ ID NO: 90: Non-limiting exemplary equivalent recombinant polypeptide sequence, Prevotella melaninogenica ATCC25845 HimA fragment: FEVKKRLERVMVNPSTGLRM SEQ ID NO: 91: Non-limiting exemplary equivalent recombinant polypeptide sequence, Prevotella intermedia 17 HimA fragment: FEVKKRLERIMTNPATGLRM SEQ ID NO: 92: Non-limiting exemplary equivalent recombinant polypeptide sequence, Treponema palladium Nichols Dbp IIf ragment: FESRVRKASVGKSINTGEVV SEQ ID NO: 93: Non-limiting exemplary equivalent recombinant polypeptide sequence, Prevotella melaninogenica ATCC25845 Hup fragment: FKVQAVKPRESVNVNTGERV SEQ ID NO: 94: Non-limiting exemplary equivalent recombinant polypeptide sequence, Prevotella intermedia 17 exemplary fragment: FKVQAVKPRESVNVNTGERV SEQ ID NO: 95: Non-limiting exemplary equivalent recombinant polypeptide sequence, S. aureus MW2 HU fragment: FEVRERAARKGRNPQTGKEI SEQ ID NO: 96: Non-limiting exemplary equivalent recombinant polypeptide sequence, E. coli K12-MG.1655 hupA fragment: FKVNHRAERTGRNPQTGKEI SEQ ID NO: 97: Non-limiting exemplary equivalent recombinant polypeptide sequence, S. epidermidis RP62A Hup fragment: FEVRERAARKGRNPQTGKEI SEQ ID NO: 98: Non-limiting exemplary equivalent recombinant polypeptide sequence, S. sobrinus 6715 Hu fragment: FEVRERAARKGRNPQTGAEI SEQ ID NO: 99: Non-limiting exemplary equivalent recombinant polypeptide sequence, S. pyogenes MGAS10270 HU fragment: FEVRERAARKGRNPQTGAEI SEQ ID NO: 100: Non-limiting exemplary equivalent recombinant polypeptide sequence, S. gallolyticus UCN34 (S. bovis) H1pA fragment: FEVRERAARKGRNPQTGEEI SEQ ID NO: 101: Non-limiting exemplary equivalent recombinant polypeptide sequence, S. agalactiae (Group B Strep)2603V/R Hup fragment: FEVRERAARKGRNPQTGAEI SEQ ID NO: 102: Non-limiting exemplary equivalent recombinant polypeptide sequence, S. pneumoniae R6 HU fragment: FEVRERAERKGRNPQTGKEM

PARTIAL SEQUENCE LISTING

SEQ ID NO: 103: Non-limiting exemplary equivalent recombinant polypeptide sequence, *S. gordonii* Challis NCTC7868 H1pA fragment: FEVRERAARKGRNPQTGKEI SEQ ID NO: 104: Non-limiting exemplary equivalent recombinant polypeptide sequence, *S. mutans* UA159 HU fragment: FEVRERAARKGRNPQTGEEI SEQ ID NO: 105: Non-limiting exemplary equivalent recombinant polypeptide sequence, *Enterococcus faecalis* VS83 Hup fragment: FEVRERAARKGRNPQTGQEI SEQ ID NO: 106: Non-limiting exemplary equivalent recombinant polypeptide sequence, *H. influenzae* KW20 Rd HupA fragment: FKVNERAARTGRNPQTGAEI SEQ ID NO: 107: Non-limiting exemplary equivalent recombinant polypeptide sequence, *V. cholera* El Toz N16961 HupA fragment: FKVNHRSARTGRNPQTGEEI SEQ ID NO: 108: Non-limiting exemplary equivalent recombinant polypeptide sequence, *P. aeruginosa* HupB fragment: FAVKERAARTGRNPQTGKPI SEQ ID NO: 109: Non-limiting exemplary equivalent recombinant polypeptide sequence, *Aggregatibacter actinomycetemcomitans* D11S-1 HU fragment: FKVNARKARTGRNPQTGAEI SEQ ID NO: 110: Non-limiting exemplary equivalent recombinant polypeptide sequence, *V. cholera* El Toz N16961 HupB fragment: FSVRTRAARTGRNPKTGEEI SEQ ID NO: 111: Non-limiting exemplary equivalent recombinant polypeptide sequence, *E. coli* K12-MG.1655 hupB fragment: FAVKERAARTGRNPQTGKEI SEQ ID NO: 112: Non-limiting exemplary equivalent recombinant polypeptide sequence, *Moraxella catarrhalis* RH4 HupB fragment: FSVKERAARMGRNPKTGEAI SEQ ID NO: 113: Non-limiting exemplary equivalent recombinant polypeptide sequence, *Bordetella pertusis* Tohama 1 HupB fragment: FAVSARAARTGRNPRTGETI SEQ ID NO: 114: Non-limiting exemplary equivalent recombinant polypeptide sequence, *Moraxella catarrhalis* RH4 HimD fragment: FCLHHRSARIARNPRTGESV SEQ ID NO: 115: Non-limiting exemplary equivalent recombinant polypeptide sequence, *Prevotella melaninogenica* ATCC25845 HupB fragment: FATTERPAHEGINPRSKEKI SEQ ID NO: 116: Non-limiting exemplary equivalent recombinant polypeptide sequence, *Prevotella intermedia* 17 Hup fragment: YSVTERPAHEGINPATKQKI SEQ ID NO: 117: Non-limiting exemplary equivalent recombinant polypeptide sequence, *Treponema denticola* ATCC35405 HU fragment: DFAVLHGRKNARNPKTGEAV SEQ ID NO: 118: Non-limiting exemplary equivalent recombinant polypeptide sequence, *P. gingivalis* W83 Hup-1 fragment: FSVSERAARKGINPKTKKSI SEQ ID NO: 119: Non-limiting exemplary equivalent recombinant polypeptide sequence, *H. pylori* 26695 Hup fragment: FETAEQKGKEGKVPGSDKTY SEQ ID NO: 120: Non-limiting exemplary equivalent recombinant polypeptide sequence, *Prevotella melaninogenica* ATCC25845 HupA fragment: SFIVKHRAEKTARNISKNTTI SEQ ID NO: 121: Non-limiting exemplary equivalent recombinant polypeptide sequence, *Prevotella intermedia* 17 Hup-2 fragment: SFIVKHRAEKTARNISKNTTI SEQ ID NO: 122: Non-limiting exemplary equivalent recombinant polypeptide sequence, *P. gingivalis* W83 Hup-2 fragment: FIVKERAEKTARNISKQTTI SEQ ID NO: 123: Non-limiting exemplary equivalent recombinant polypeptide sequence, *Mycobacterium tuberculosis* CDC1551 HU fragment: FEQRRRAARVARNPRTGETV SEQ ID NO: 124: Non-limiting exemplary equivalent recombinant polypeptide sequence, *Mycobacterium smegmatis* MC2 Hup fragment: FEQRRRAARVARNPRTGETV SEQ ID NO: 125: Non-limiting exemplary equivalent recombinant polypeptide sequence, *E. coli* K12-MG 1655 HimD fragment: FSLHYRAPRTGRNPKTGDKV SEQ ID NO: 126: Non-limiting exemplary equivalent recombinant polypeptide sequence, *Salmonella enteric serovar typhi* CT18 HimD fragment: FSLHYRAPRTGRNPKTGDKV SEQ ID NO: 127: Non-limiting exemplary equivalent recombinant polypeptide sequence, *V. cholera* El Toz N16961 HipB fragment: FSLHYREPRVGRNPKTGDKV

US 11,564,982 B2

-continued

PARTIAL SEQUENCE LISTING

SEQ ID NO: 128: Non-limiting exemplary equivalent recombinant polypeptide sequence, P. aeruginosa HimD fragment: FSLHYRAPRVGRNPKTGESV SEQ ID NO: 129: Non-limiting exemplary equivalent recombinant polypeptide sequence, Aggregatibacter actinomycetemcomitans D115-1 IHFB fragment: FSLHCRQPRIGRNPKTGEQV SEQ ID NO: 130: Non-limiting exemplary equivalent recombinant polypeptide sequence, N. gonorrhoeae FA1090 (Oklahoma) IHFf3 fragment: FDLNHRPARIGRNPKTGERV SEQ ID NO: 131: Non-limiting exemplary equivalent recombinant polypeptide sequence, N. meningitides MC5B HimD fragment: FDLNHRPARIGRNPKTGERV SEQ ID NO: 132: Non-limiting exemplary equivalent recombinant polypeptide sequence, Burkholderia cenocepacia HI2424 IHFB fragment: FGLNRRPARVGRNPKSGEKV SEQ ID NO: 133: Non-limiting exemplary equivalent recombinant polypeptide sequence, Burkholderia pseudomallei 668 IHFB fragment: FGLNRRPARVGRNPKSGEKV SEQ ID NO: 134: Non-limiting exemplary equivalent recombinant polypeptide sequence, Bordetella pertusis Tohama 1 IhfB fragment: FSLSQRSPRIGRNPKSGEQV SEQ ID NO: 135: Non-limiting exemplary equivalent recombinant polypeptide sequence, B. burgdorferi B31 Hbb fragment: FEVRKRKGRLNARNPQTGEYV SEQ ID NO: 136: Haemophilus influenzae KW20 Rd Ihfl3, modified B4 (mB4) fragment: FSLHHRQPRLGRNPKTGDSV

BRIEF DESCRIPTION OF THE DRAWINGS

FIG. 2A shows the reciprocal titers for chinchilla serum and rabbit serum generated using the IhfA5-mIhfB4$_{NTHI}$ chimer recombinant polypeptides. Chinchilla and rabbit serum anti-IhfA3$_{NTHI}$, anti-IhfA5$_{NTHI}$, anti-mIhfB4$_{NTHI}$ (IhfA3$_{NTHI}$: SEQ ID NO.: 12, IhfA5$_{NTHI}$: SEQ ID NO: 13, and mIhfB4$_{NTHI}$: SEQ ID NO: 17), and anti-IhfA5-mIhfB4$_{NTHI}$ chimer (IhfA5-mIhfB4$_{NTHI}$ chimer: SEQ ID NO.: 50) samples were analyzed to assess reactivity with IhfA5-mIhfB4$_{NTHI}$ chimer peptide. FIG. 2B depicts the disruption of biofilms formed by Haemophilus influenzae (NTHI) 86-028NP upon incubation with medium control or various chinchilla serum as follows: naïve serum control, anti-IhfA3$_{NTHI}$, anti-IhfA5$_{NTHI}$, anti-mIhfB4$_{NTHI}$, and anti-IhfA5-mB4$_{NTHI}$ chimer. A 1:50 dilution of chinchilla serum was used. The reduction in biomass shown is relative to naïve serum.

DESCRIPTION OF TABLES

Figure 1:
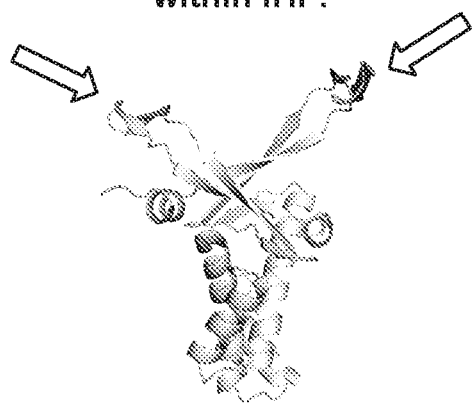
FIG. 1 depicts an exemplary IHF$_{NTHI}$ tip-directed chimeric recombinant peptide used to generate polyclonal serum in chinchillas and rabbits. The "IhfA5-mIhfB4$_{NTHI}$ chimer" has an A5 sequence, i.e., Haemophilus influenzae IhfA5 sequence, followed by a linker sequence (GPSL) followed by an mB4 polypeptide, i.e., Haemophilus influenzae mIhfB4$_{NTHI}$ sequence: (SEQ ID NO: 50: RPGRNPKTGDVVPVSARRVVGPSLFSLHHRQPRL-GRNPKTGDSV). The corresponding structural regions targeted within IHF are shown below the peptide sequence, as indicated by the arrows.

Table 1 is a summary of examples of conformational tip domain polypeptides.

Table 2 is a summary of the scoring methodology used in the otitis media model of Example 3 to generate a mucosal biomass score.

Table 3 is a summary of the efficacies of rabbit IgG Fab polyclonal fragments versus intact rabbit polyclonal IgG.

DETAILED DESCRIPTION

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Green and Sambrook eds. (2012) Molecular Cloning: A Laboratory Manual, 4th edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press); MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, 6th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) In Vitro Transcription and Translation Protocols, 2nd edition; Guisan ed. (2006) Immobilization of Enzymes and Cells; Perbal (1988) A Practical Guide to Molecular Cloning, 2nd edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, 4th edition; and Herzenberg et al. eds (1996) Weir's Handbook of Experimental Immunology, 5th edition.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives (e.g., sodium benzoate, potassium sorbate, and methyl hydroxybenzoate), and the like. "Consisting of" shall mean excluding more than trace elements of other ingredients and substantial method steps for administering the compositions disclosed herein. Embodiments defined by each of these transition terms are within the scope of this disclosure.

A "biofilm" intends an organized community of microorganisms that at times adhere to the surface of a structure that may be organic or inorganic, together with the polymers such as DNA that they secrete and/or release. Biofilms are very resistant to microbiotics and antimicrobial agents. They live on various organic and inorganic surfaces, e.g., gingival tissues, teeth and restorations, causing caries and periodontal disease, also known as periodontal plaque disease. They also cause middle ear infections. They can also form on the surface of dental implants, stents, catheter lines and contact lenses. They grow on pacemakers, heart valve replacements, artificial joints and other surgical implants. The Centers for Disease Control) estimate that over 65% of nosocomial (hospital-acquired) infections are caused by biofilms. They cause vaginal infections and lead to life-threatening systemic infections in people with hobbled immune systems. Biofilms also are involved in numerous diseases, including but not limited to those caused by *Aggregatibacter actinomycetemcomitans, Borrelia burgdorferi* (e.g., B31), *Bordetella pertussis* (e.g., Tohama I), *Burkholderia pseudomallei* (e.g., 668), *Burkholderia cenocepacia* (e.g., HI2424), *Escherichia coli* (e.g., K12 MG1655), *Enterococcus faecalis* (e.g., V583), *Haemophilus influenzae* (e.g., Rd KW20), *Helicobacter pylori* (e.g., 26695), *Klebsiella pneumoniae, Moraxella catarrhalis* (e.g., RH4), *Mycobacterium smegmatis* (e.g., MC2), *Mycobacterium tuberculosis* (e.g., CDC1551), *Neisseria gonorrhoeae* (e.g., FA1090), *Neisseria meningitidis* (e.g., MC58), *Pseudomonas aeruginosa, Porphyromonas gingivalis* (e.g., W83), *Prevotella intermedia* (e.g., 17), *Prevotella melaninogenica* (e.g., ATCC® 25845), *Staphylococcus aureus* (e.g., MW2), *Staphylococcus epidermidis* (e.g., RP62A), *Streptococcus agalactiae* (e.g., 2603V/R), *Streptococcus bovis, Streptococcus gallolyticus* (e.g., UCN34), *Streptococcus gordonii* (e.g., NCTC 7868 (Challis)), *Streptococcus mutans* (e.g., UA159), *Streptococcus pneumoniae* (e.g., R6), *Streptococcus pyogenes* (e.g., MGAS10270), *Streptococcus sobrinus* (e.g., 6715), *Salmonella enterica* (e.g., *typhi*, CT18), *Treponema denticola* (e.g., ATCC® 35405), *Treponema palladum* (e.g., Nichols), and *Vibrio cholera* (e.g., El Tor, N16961). Additional organisms known to associate with and/or form biofilms include but are not limited to *Campylobacter* spp., *Candida* spp., *Legionella pneumophila,* and *Listeria monocytogenes*. For instance, cystic fibrosis patients have *Pseudomonas* infections that often result in antibiotic resistant biofilms. Other diseases associated with biofilms include, but are not limited to, lung infections of cystic fibrosis patients, otitis media, post-tympanostomy tube ottorhea, chronic suppurative otitis media, native valve infectious endocarditis, osteomyelitis, rhinosinositis, prostatitis, urinary tract infection, wounds, dental caries and periodontitis. Foodborne pathogens, such as but not limited to some of the above listed organisms (e.g., *Listeria monocytogenes, Escherichia coli*, and *Salmonella enterica*) may also form biofilms on the food that they contaminate. Disease causing biofilms in animals (e.g., *Escherichia coli, Salmonella,* and *Shigella* species) may also cause downstream food contamination and/or disease in human hosts. Further, biofilms need not be of one homogeneous microbial population and may incorporate other pathogens and even host cells. In addition to being associated with disease—both nosocomial and otherwise—and food contamination, biofilms are often causes of industrial contamination, most notably in relation to process waters and surfaces in contact therewith. Complications involving organisms that form biofilm as industrial contaminants include but are not limited to biocorrosion, biofouling, and equipment damage as a result of biofilm formation. Non-limiting exemplary organisms associated with biofilms in industrial settings include those disclosed in Ferrera et al. (2015) Biofouling 31(2):173-180 and *Desulfovibrio* species. Additional details regarding biofilms may be found in, for example, Donlan (2002) Emerging Infectious Diseases 8(9):881-890.

The term "to prevent formation of a biofilm" intends a prevention in the formation of, or structure of, the DNA/protein matrix that is a component of a microbial biofilm.

The terms "to dissolve" or "to disrupt" a biofilm intends a reduction or disruption in the formation of, or structure of, the DNA/protein matrix that is a component of a microbial biofilm.

The term "nucleoid associated protein" or "NAP" as used herein refers to a class of proteins that affect the dynamic spatial organization of nucleic acids in the nucleoid of prokaryotic cells. These proteins organize the genome through effecting DNA bending, binding and aggregation. Certain NAPs are DNA binding proteins and may be associated with the biofilm including, DNABII proteins, DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813). Of the NAPs, DNABII proteins are distinct and generally have strong sequence identity with alpha helical dimerization domains and may comprise anti-parallel beta ribbons, which often have $NPX_1T$ amino acid motifs, comprising tips that bind and intercalate into the minor groove of DNA and kink it.

A "DNABII polypeptide or protein" intends a DNA binding protein or polypeptide that is composed of DNA-binding domains and thus have a specific or general affinity for microbial DNA. In one aspect, they bind DNA in the minor grove. Non-limiting examples of DNABII proteins are an integration host factor (IHF) protein and a histone-like protein (HU).

The term "*Haemophilus influenzae*" refers to pathogenic bacteria that can cause many different infections such as, for example, ear infections, eye infections, and sinusitis. Many different strains of *Haemophilus influenzae* have been isolated and have an IhfA gene or protein. Some non-limiting examples of different strains of *Haemophilus influenzae* include Rd KW20, 86-028NP, R2866, PittGG, PittEE, R2846, and 2019.

An "integration host factor" or "IHF" protein is a bacterial protein that is used by bacteriophages to incorporate their DNA into the host bacteria. They also bind extracellular microbial DNA. The genes that encode the IHF protein subunits in *E. coli* are himA (Genbank Accession No.: POA6X7.1) and himD (POA6Y1.1) genes. Homologs for these genes are found in other organisms and as described in in Table 10 of U.S. Pat. No. 8,999,291, incorporated herein by reference.

"HU" or "histone-like protein" refers to a class of heterodimeric proteins typically associate with *E. coli*. HU proteins are known to bind DNA Holliday junctions or other bent structures. Related proteins have been isolated from other microorganisms. The complete amino acid sequence of *E. coli* HU was reported by Laine et al. (1980) Eur. J. Biochem 103(3):447-481. The genes that encode the HU protein subunits in *E. coli* are hupA and hupB corresponding to SEQ ID NOs. 8 and 9, respectively. A *Haemophilus influenzae* homolog derived from non-typeable *Haemophilus influenzae* (NTHI) corresponds to SEQ ID NO. 3. Homologs for these genes are found in other organisms as described in Table 10 of U.S. Pat. No. 8,999,291, incorporated herein by reference.

"Microbial DNA" intends single or double stranded DNA from a microorganism that is used to produce the extracellular matrix of a biofilm.

"A conformational tip domain" of a polypeptide refers to a polypeptide that comprises a primary amino acid sequence wherein the structure has an anti-parallel beta ribbon with a sharp turn that is typically mediated by a proline residue. The "tip" of an IHF polypeptide is shown in FIG. 1.

"Treating an infection" intends a reduction in the number of microbes, e.g., bacteria, and in one aspect as used herein, the term is intended to be associated with the formation of a biofilm. Methods to determine if the number of microbes has been reduced are known in the art and include in vivo and ex vivo assays, as well as a reduction in the clinical symptoms of an infection. Because bacteria are protected by the biofilms, the bacteria become resistance to the use of antibacterials. By breaking down the biofilm one can reduce or inhibit bacterial resistance to antibacterial and other agents as well as treat the bacterial infection.

A "bent polynucleotide" intends a double strand polynucleotide that contains a small loop on one strand which does not pair with the other strand. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9, or 10 bases.

"Polypeptides that compete with DNABII proteins in DNA binding" intend proteins or peptides that compete with IHF or HU in binding bent or distorted DNA structures but do not form a biofilm with the DNA. Examples, without limitation, include conformational tip fragments of IHF that include one or more DNA binding domains of the IHF, or the biological equivalents thereof.

As used herein, the term "specifically recognize or bind" intends that the binding agent, e.g., a antibody, antigen binding fragment or a Fab (fragment antigen binding) is more likely than not to bind to its intended target or binding partner.

A "subject" of diagnosis or treatment is a cell or an animal such as a mammal, or a human. A subject is not limited to a specific species and includes non-human animals subject to diagnosis or treatment and are those subject to infections or animal models, for example, simians, murines, such as, rats, mice, chinchilla, canine, such as dogs, leporids, such as rabbits, livestock, sport animals, and pets. Human patients are included within the term as well.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or a gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide or Fab (fragment antigen binding) intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

Table 1 below shows examples of conformational tip domain polypeptides.

TABLE 1

| Abbreviation (Protein name) | Bacterial strain | Sequence | SEQ ID NO: |
|---|---|---|---|
| Ec_HimA (b1712) | *E. coli* K12-MG1655 | FDLRDKNQRPGRNPKTGEDI | SEQ ID NO: 78 |
| Salm_HimA (Sty1771) | *Salmonella enteric serovar typhi* CT18 | FDLRDKNQRPGRNPKTGEDI | SEQ ID NO: 79 |
| Vc_HimA (VC_0273) | *V. cholera* El Toz N16961 | FDLRDKNERPGRNPKTGEDI | SEQ ID NO: 80 |
| Pa_HimA (NMB_1302) | *P. aeruginosa* | FDLRDKRQRPGRNPKTGEEI | SEQ ID NO: 81 |
| Hi_HimA (HI1221) | *H. influenzae* KW20 Rd | FELRDKSSRPGRNPKTGDVV | SEQ ID NO: 82 |
| Aa_IHFalpha (YP_003255965) | *Aggregatibacter actinomycetemcomitans* D11S-1 | FELRDKASRPGRNPKTGESV | SEQ ID NO: 83 |
| Mc HimA (YP_003626307) | *Moraxella catarrhalis* RH4 | FELKDKKPRPGRNPKTGESV | SEQ ID NO: 84 |
| Ng_IHFalpha (NGO603) | *N. gonorrhoeae* FA1090 (Oklahoma) | FQLRDKPQRPGRNPKTGEEV | SEQ ID NO: 85 |
| Nm_HimA (NMB_0729) | *N. meningitides* MC5B | FQLRDKPQRPGRNPKTGEEV | SEQ ID NO: 86 |
| Bc IHFA (Bcen2424_1481) | *Burkholderia cenocepacia* HI2424 | FQLRDKPQRPGRNPKTGEAI | SEQ ID NO: 87 |
| Bp IHFA (BURPS668_1718) | *Burkholderia pseudomallei* 668 | FQLRDKPQRPGRNPNTGEAI | SEQ ID NO: 88 |
| Bpert IhfA (BP2572) | *Bordetella pertusis* Tohama 1 | FQVRDKPPRPGRNPKTGETI | SEQ ID NO: 89 |
| Pm HimA | *Prevotella melaninogenica* ATCC 25845 | FEVKKRLERVMVNPSTGLRM | SEQ ID NO: 90 |
| Pi HimA (PIN_0345) | *Prevotella intermedia* 17 | FEVKKRLERIMTNPATGLRM | SEQ ID NO: 91 |
| Tp Dbp II (TP_0251) | *Treponema palladium* Nichols | FESRVRKASVGKSINTGEVV | SEQ ID NO: 92 |
| Pm Hup | *Prevotella melaninogenica* ATCC 25845 | FKVQAVKPRESVNVNTGERV | SEQ ID NO: 93 |

TABLE 1-continued

| Abbreviation (Protein name) | Bacterial strain | Sequence | SEQ ID NO: |
|---|---|---|---|
| Pi hypo (PIN_0343) | Prevotella intermedia 17 | FKVQAVKPRESVNVNTGERV | SEQ ID NO: 94 |
| Sa_HU (MW1362) | S. aureus MW2 | FEVRERAARKGRNPQTGKEI | SEQ ID NO: 95 |
| Ec hupA | E. coli K12-MG.1655 | FKVNHRAERTGRNPQTGKEI | SEQ ID NO: 96 |
| Se Hup (SERP1041) | S. epidermidis RP62A | FEVRERAARKGRNPQTGKEI | SEQ ID NO: 97 |
| Ss Hu (1310) | S. sobrinus 6715 | FEVRERAARKGRNPQTGAEI | SEQ ID NO: 98 |
| Spyog_HU (Spy1239) | S. pyogenes MGAS10270 | FEVRERAARKGRNPQTGAEI | SEQ ID NO: 99 |
| Sgall_HlpA (YP_003430069) | S. gallolyticus UCN34 (S. bovis) | FEVRERAARKGRNPQTGEEI | SEQ ID NO: 100 |
| GBS_Hup (SAG_0505) | S. agalactiae (Group B Strep)2603V/R | FEVRERAARKGRNPQTGAEI | SEQ ID NO: 101 |
| Spneu_HU (spr1020) | S. pneumoniae R6 | FEVRERAERKGRNPQTGKEM | SEQ ID NO: 102 |
| Sg_HlpA (SGO_0701) | S. gordonii Challis NCTC7868 | FEVRERAARKGRNPQTGKEI | SEQ ID NO: 103 |
| Sm_HU (Smu_589) | S. mutans UA159 | FEVRERAARKGRNPQTGEEI | SEQ ID NO: 104 |
| Ef Hup (Efl 550) | Enterococcus faecalis V583 | FEVRERAARKGRNPQTGQEI | SEQ ID NO: 105 |
| Hi_HupA (HI0430) | H. influenzae KW20 Rd | FKVNERAARTGRNPQTGAEI | SEQ ID NO: 106 |
| Vc_HupA (VC_0273) | V. cholera El Toz N16961 | FKVNHRSARTGRNPQTGEEI | SEQ ID NO: 107 |
| Pa_HupB | P. aeruginosa | FAVKERAARTGRNPQTGKPI | SEQ ID NO: 108 |
| Aa HU | Aggregatibacter actinomycetemcomitans D11S-1 | FKVNARKARTGRNPQTGAEI | SEQ ID NO: 109 |
| Vc_HupB (VC_1919) | V. cholera El Toz N16961 | FSVRTRAARTGRNPKTGEEI | SEQ ID NO: 110 |
| Ec hupB | E. coli K12-MG.1655 | FAVKERAARTGRNPQTGKEI | SEQ ID NO: 111 |
| Mc HupB (YP_003626775) | Moraxella catarrhalis RH4 | FSVKERAARMGRNPKTGEAI | SEQ ID NO: 112 |
| Bpert HupB (BP3530) | Bordetella pertusis Tohama 1 | FAVSARAARTGRNPRTGETI | SEQ ID NO: 113 |
| Mc HimD (YP_003627027) | Moraxella catarrhalis RH4 | FCLHHRSARIARNPRTGESV | SEQ ID NO: 114 |
| Pm HupB (PREME0022_2103) | Prevotella melaninogenica ATCC 25845 | FATTERPAHEGINPRSKEKI | SEQ ID NO: 115 |
| Pi Hup (PIN_A0704) | Prevotella intermedia 17 | YSVTERPAHEGINPATKQKI | SEQ ID NO: 116 |
| Td HU (TDE_1709) | Treponema denticola ATCC 35405 | DFAVLHGRKNARNPKTGEAV | SEQ ID NO: 117 |

TABLE 1-continued

| Abbreviation (Protein name) | Bacterial strain | Sequence | SEQ ID NO: |
|---|---|---|---|
| Pg_Hup-1 (PG_0121) | P. gingivalis W83 | FSVSERAARKGINPKTKKSI | SEQ ID NO: 118 |
| Hp_Hup (Hp0835) | H. pylori 26695 | FETAEQKGKEGKVPGSDKTY | SEQ ID NO: 119 |
| Pm HupA (PREME0022_0268) | Prevotella melaninogenica ATCC 25845 | SFIVKHRAEKTARNISKNTTI | SEQ ID NO: 120 |
| Pi Hup-2 (PIN_A1504) | Prevotella intermedia 17 | SFIVKHRAEKTARNISKNTTI | SEQ ID NO: 121 |
| Pg_Hup-2 (PG_1258) | P. gingivalis W83 | FIVKERAEKTARNISKQTTI | SEQ ID NO: 122 |
| Mt HU (MT_3064) | Mycobacterium tuberculosis CDC1551 | FEQRRRAARVARNPRTGETV | SEQ ID NO: 123 |
| Ms Hup (MSMEG_2389) | Mycobacterium smegmatis MC2 | FEQRRRAARVARNPRTGETV | SEQ ID NO: 124 |
| Ec_HimD (b0912) | E. coli K12-MG 1655 | FSLHYRAPRTGRNPKTGDKV | SEQ ID NO: 125 |
| Salm_HimD (Sty0982) | Salmonella enteric serovar typhi CT18 | FSLHYRAPRTGRNPKTGDKV | SEQ ID NO: 126 |
| Vc_HipB (VC_1914) | V. cholera El Toz N16961 | FSLHYREPRVGRNPKTGDKV | SEQ ID NO: 127 |
| Pa_HimD (PA3161) | P. aeruginosa | FSLHYRAPRVGRNPKTGESV | SEQ ID NO: 128 |
| Hi_HimD (HI1313) | H. influenzae KW20 Rd | FSLHHRQPRLGRNPKTGDSV | SEQ ID NO: 136 |
| Aa_IHFB (YP_003256209) | Aggregatibacter actinomycetemcomitans D11S-1 | FSLHCRQPRIGRNPKTGEQV | SEQ ID NO: 129 |
| Ng_IHFβ (NGO603) | N. gonorrhoeae FA1090 (Oklahoma) | FDLNHRPARIGRNPKTGERV | SEQ ID NO: 130 |
| Nm HimD | N. meningitides MC5B | FDLNHRPARIGRNPKTGERV | SEQ ID NO: 131 |
| Bc IHFB (Bcen2424_1048) | Burkholderia cenocepacia HI2424 | FGLNRRPARVGRNPKSGEKV | SEQ ID NO: 132 |
| Bp IHFB (BURPS668_2881) | Burkholderia pseudomallei 668 | FGLNRRPARVGRNPKSGEKV | SEQ ID NO: 133 |
| Bpert IhfB (BP0951) | Bordetella pertusis Tohama 1 | FSLSQRSPRIGRNPKSGEQV | SEQ ID NO: 134 |
| Bb_Hbb (BB_0232) | B. burgdorferi B31 | FEVRKRKGRLNARNPQTGEYV | SEQ ID NO: 135 |

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity can determined by incorporating them into clustalW (available at the web address: genome.jp/tools/clustalw/, last accessed on Jan. 13, 2017).

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder. Methods to determine if treatment has occurred are known in the art and briefly described herein.

To prevent intends to prevent a disorder or effect in vitro or in vivo in a system or subject that is predisposed to the disorder or effect. An example of such is preventing the formation of a biofilm in a system that is infected with a microorganism known to produce one.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, microspheres, microparticles, or nanoparticles (comprising e.g., biodegradable polymers such as Poly(Lactic Acid-co-Glycolic Acid)), and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

A "biologically active agent" or an active agent disclosed herein intends one or more of an isolated or recombinant polypeptide, an isolated or recombinant polynucleotide, a vector, an isolated host cell, or an antibody, as well as compositions comprising one or more of same.

"Administration" or "delivery" of a therapeutic or other agent can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application. Administration can be for use in industrial as well as therapeutic applications.

An agent (an antibody or fragment thereof, a polypeptide, a polynucleotide, a cell, a composition or a vaccine) of the present disclosure can be administered for its intended use whether in vitro or in vivo (e.g., therapeutically) by any suitable route of administration. It will also be appreciated that the optimal route will vary with the condition and age of the recipient, and the disease being treated. The agent may be used in industrial settings and for the treatment of animals. When used in industrial settings, the biofilm is contacted with the agent, e.g., Fab (fragment antigen binding), antibody, polypeptide or vaccine.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, species, and tolerance to pharmaceutical compositions. In the context of this disclosure, in some embodiments the effective amount is the amount sufficient to result a reduction in biofilm mass or in breaking down a biofilm. In other aspects, the amount is effective to treat a bacterial infection associated with a biofilm in a subject. In other embodiments, in the context of a Fab (fragment antigen binding) or antibody, the effective amount is the amount sufficient to result in breaking down, diminishing or disrupting a biofilm. In other embodiments, the effective amount of an agent or an immunogenic composition is the amount sufficient to result in antibody generation against the antigen. In some embodiments, the effective amount is the amount required to confer passive immunity on a subject in need thereof. With respect to compositions, in some embodiments the effective amount will depend on the intended use, the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The term "potency" as it relates to the potency of a drug, such as an antibiotic refers to to a measure of drug activity expressed in terms of the amount required to produce an effect of given intensity. A highly potent drug evokes a given response at low concentrations, while a drug of lower potency evokes the same response only at higher concentrations. The potency depends on both the affinity and efficacy.

The term "conjugated moiety" refers to a moiety that can be added to an isolated chimeric polypeptide by forming a covalent bond with a residue of chimeric polypeptide. The moiety may bond directly to a residue of the chimeric polypeptide or may form a covalent bond with a linker which in turn forms a covalent bond with a residue of the chimeric polypeptide.

A "peptide conjugate" or "recombinant polypeptide" refers to the association by covalent or non-covalent bonding of one or more polypeptides with each other and/or with another chemical or biological compound. In a non-limiting example, the "conjugation" of a polypeptide with a chemical compound results in improved stability or efficacy of the polypeptide for its intended purpose. In one embodiment, the active agents of this disclosure are conjugated to a carrier, wherein the carrier is a liposome, a micelle, or a pharmaceutically acceptable polymer.

"Liposomes" are microscopic vesicles consisting of concentric lipid bilayers. A liposome is an example of a carrier, e.g., a pharmaceutically acceptable carrier. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double $C=C$ bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, di stearoylphosphatidylethan-olamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioteoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody, antigen binding fragment, vaccine, or composition described herein to facilitate efficient delivery to the target cell or tissue.

The phrase "pharmaceutically acceptable polymer" refers to the group of compounds which can be conjugated to one or more polypeptides or antibodies described here. It is contemplated that the conjugation of a polymer to the polypeptide or antibody is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

As used herein the term "eDNA" refers to extracellular DNA found as a component to pathogenic biofilms.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. Ads do not require integration into the host cell genome. Recombinant Ad derived vectors, particularly those that reduce the potential for recombination and generation of wild-type virus, have also been constructed. Such vectors are commercially available from sources such as Takara Bio USA (Mountain View, Calif.), Vector Biolabs (Philadelphia, Pa.), and Creative Biogene (Shirley, N.Y.). Wild-type AAV has high infectivity and specificity integrating into the host cell's genome. See, Wold and Toth (2013) Curr. Gene. Ther. 13(6):421-433, Hermonat & Muzyczka (1984) Proc. Natl. Acad. Sci. USA 81:6466-6470, and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', $F(ab)_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, species-ized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-IHF, anti-HU, anti-OMP P5, for example, refers to a monoclonal or polyclonal antibody that binds and/or has an affinity to a particular protein. For example, "anti-IHF" refers to an antibody that binds to the IHF protein. The specific antibody may have affinity or bind to proteins other than the protein it was raised against. For example, anti-IHF, while specifically raised against the IHF protein, may also bind other proteins that are related either through sequence homology or through structure homology.

The antibodies can be polyclonal, monoclonal, multispecific (e.g., bispecific antibodies), a diabody, and antibody fragments, so long as they exhibit the desired biological activity. Antibodies can be isolated from any suitable biological source, e.g., a human, a murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like and can be used, therapeutically, diagnostically or to isolate a polypeptide.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin. Additional non-limiting examples of linker polypeptides are provided herein.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine. The term "species-ized" refers to antibodies that have been modified in the same or a similar manner for a non-human species.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope. In some embodiments, the antibody or antigen binding fragment is not a polyclonal antibody.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof. This disclosure also provided antibody derivatives of the antibody fragments, e.g., the polypeptides conjugated to another molecule, e.g., PEG or further modified by acylation.

As used herein, the term "immunoconjugate" comprises an antibody, an antibody fragment or a antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody. This disclosure provides immunoconjugates comprising as one component, an antibody or Fab fragment and the second agent.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to a polynucleotide that will provide a signal upon expression of the inserted sequences, such as green fluorescent protein (GFP) and the like. The term also includes purification tags or labels that aid in the isolation of biological materials from mixed populations. While the term "label" generally intends compositions covalently attached to the composition to be detected, in one aspect it specifically excludes naturally occurring nucleosides and amino acids that are known to fluoresce under certain conditions (e.g., temperature, pH, etc.) when positioned within the polynucleotide or protein in its native environment and generally any natural fluorescence that may be present in the composition to be detected. The label may be detectable by itself (e.g., radioisotope labels or fluorescent labels) or, in the case of an enzymatic label, may catalyze chemical alteration of a substrate compound or composition that is detectable. The labels can be suitable for small-scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, CASCADE BLUE™, and Texas Red.

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances that are immunogenic, i.e., immunogens, as well as substances which induce immunological unresponsiveness, or anergy, i.e., anergens.

An "altered antigen" is one having a primary sequence that is different from that of the corresponding wild-type antigen. Polypeptide mB4 (SEQ ID NO.: 17) is an example of an altered B4 antigen (SEQ ID NO.: 16). Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand (Ferguson et al. (1988) Ann. Rev. Biochem. 57:285-320).

A "self-antigen" also referred to herein as a native or wild-type antigen is an antigenic peptide that induces little or no immune response in the subject due to self-tolerance to the antigen. An example of a self-antigen is the melanoma specific antigen gp100.

"Immune response" broadly refers to the antigen-specific responses of lymphocytes to foreign substances. The terms "immunogen" and "immunogenic" refer to molecules with the capacity to elicit an immune response. All immunogens are antigens; however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

The term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

As used herein, the term "inducing an immune response in a subject" is a term well understood in the art and intends that an increase of at least about 2-fold, at least about 5-fold, at least about 10-fold, at least about 100-fold, at least about 500-fold, or at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

As used herein, the term "anti-inflammatory cytokines" includes immunoregulatory molecules that control the proinflammatory cytokine response. Cytokines act together with specific cytokine inhibitors and soluble cytokine receptors to regulate the human immune response. Major anti-inflammatory cytokines include interleukin (IL)-1 receptor antagonist, IL-4, IL-6, IL-10, IL-11, and IL-13. Specific cytokine receptors for IL-1, tumor necrosis factor-alpha, and IL-18 also function as proinflammatory cytokine inhibitors. Methods of measuring cytokine, including anti-inflammatory cytokine, levels are well known in the art. For example, serum cytokine levels can be measured using commercially available enzyme-linked immuno-sorbent assay (ELISA) kits.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., ChemPep, Inc., etc.), PolyHIPE resins, which is a copolymer based on polystyrene with grafted polydimethylacrylamide; HIPE=high internal phase emulsionpolyamide resin (obtained from Sigma-Aldrich, St. Louis, Mo.), polystyrene resin grafted with polyethylene glycol (TentaGel®, Rapp Polymere, Tubingen, Germany) or polydimethylacrylamide resin (obtained from Sigma-Aldrich, St. Louis, Mo.).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

MODES FOR CARRYING OUT THE DISCLOSURE

Chimer Recombinant Polypeptides

This disclosure provides a recombinant polypeptide comprising, or consisting essentially of, or yet further consisting of, two or more isolated conformational tip domains of a DNABII polypeptide, e.g., a fragment of a DNABII polypeptide that in one aspect, contains the $NPX_1T$ peptide motif, or a biological equivalent of one or more of the conformational tip domains or fragments thereof, wherein for fragments having the motif, "$X_1$" is any amino acid or alternatively "$X_1$" is selected from the amino acids Q, R, K, S, or T. In one aspect, the amino acid sequences of the two or more tip domains are the same, or alternatively the amino acids sequences are different. Non-limiting examples of the conformational tip domains comprise, or alternatively consist essentially of, or yet further consist of the fragments identified herein as A5 and mB4, and equivalents of each thereof and $NPX_1T$ containing fragments of each thereof wherein "$X_1$" is any amino acid or alternatively "$X_1$" is selected from the amino acids Q, R, K, S, or T. The structural orientation of the tip domains can be "head" to tail; tail to head wherein the polypeptide comprises 3 or more tip domains, any combination of head to tails, e.g., head-head-head; tail-head-heard; tail-head-tail, wherein the amine terminus of the wild-type sequence is the "head" and the carboxy terminus of the wild-type sequence is the "tail" of the polypeptide. Non-limiting examples of the polypeptides include, without limitation the polypeptides disclosed herein, e.g., the polypeptides identified in the Sequence Listing.

Further provided as polypeptides are those disclosed as A1 to A4 and A6 and B1 to B6, disclosed above as Sequence ID NOs.: 18, 19, 12, 20, 21, 22, 15, 23, 16, 24, and 25, which do not contain the conformation tip domain, and equivalents of these polypeptides from different organisms identified herein that produce a DNABII polypeptide. The sequences comprise:

```
MATITKLDIIEYLSDKYHLS (also referred to herein as

A1; (SEQ ID NO. 18));

KYHLSKQDTKNVVENFLEEI (also referred to herein as

A2; (SEQ ID NO. 19));

FLEEIRLSLESGQDVKLSGF (also referred to herein as

A3; (SEQ ID NO. 12));

KLSGFGNFELRDKSSRPGRN (also referred to herein as

A4; (SEQ ID NO. 20));

ARRVVTFKPGQKLRARVEKTK (also referred to herein as

A6; (SEQ ID NO. 21));

MTKSELMEKLSAKQPTLSAK (also referred to herein as

B1 (SEQ ID NO. 22));

TLSAKEIENMVKDILEFISQ (also referred to herein as

B2 (SEQ ID NO. 15));

EFISQSLENGDRVEVRGFGS (also referred to herein as

B3 (SEQ ID NO. 23));

RGFGSFSLHHRQPRLGRNPK (also referred to herein as

B4 (SEQ ID NO. 16));

GRNPKTGDSVNLSAKSVPYF (also referred to herein as

B5; (SEQ ID NO. 24));
and

SVPYFKAGKELKARVDVQA (also referred to herein as

B6; (SEQ ID NO. 25));
```

Non-limiting examples of DNABII polypeptides include an IHF or HU alpha or beta polypeptide; an IHF alpha polypeptide; *Moraxella catarrhalis* HU; *E. coli* HupA, HupB, himA, himD; *E. faecalis* HU (such as V583).

In a further aspect, the recombinant polypeptide further comprises, or alternatively consists essentially of, or yet further consists of a linker polypeptide that further comprises, or alternatively consists essentially of, or yet further consists of 1 or more amino acids. Non-limiting examples of linker polypeptides include, without limitation those identified herein.

Also provided are recombinant polypeptides that comprise, or alternatively consist essentially of, or yet further consist of, between 3 and 5 conformational tip domains that can be produced by the same or different bacterial species, the amino acids sequences of which can be the same (e.g., all A5 amino acid sequences) or at least 2 or at least 3 or at least 4 or all 5 having different amino acid sequences (e.g., various combinations of A5 and mB4 and equivalents and NPX$_1$T containing fragments of each thereof), wherein X$_1$ is any amino acid, or in one aspect, an amino selected from the amino acids Q, R, K, S, or T. The conformational tip domains in the recombinant polypeptides can be in a linear or branched conformation. They can further comprise a detectable and/or a purification label linked thereto. The structural orientation of the tip domains can be "head" to tail; tail to head wherein the polypeptide comprises 3 or more tip domains, any combination of head to tails, e.g., head-head-head; tail-head-heard; tail-head-tail, wherein the amine terminus of the wild-type sequence is the "head" and the carboxy terminus of the wild-type sequence is the "tail" of the polypeptide. In one aspect, the polypeptides in sum can be between 41 and 120 amino acids in length.

Non-limiting examples of equivalent polypeptides, include a polypeptide having at least 60%, or alternatively at least 65%, or alternatively at least 70%, or alternatively at least 75%, or alternatively 80%, or alternatively at least 85%, or alternatively at least 90%, or alternatively at least 95% identity thereto or for polypeptide sequences, or a polypeptide which is encoded by a polynucleotide or its complement that hybridizes under conditions of high stringency to a polynucleotide encoding such polypeptide sequences. Conditions of high stringency are described herein and incorporated herein by reference. Applicants have determined that the bolded and underlined amino acids are heavily conserved and therefore in one aspect, are not modified or altered in designing an equivalent polypeptide. Additional examples of equivalent polypeptides include, for example DKSSRPGRNPX$_1$TGDVVAASARR (SEQ ID NO.: 77), wherein "X$_1$" is any amino acid or alternatively "X$_1$" is selected from the amino acids Q, R, K, S, or T.

Equivalent polypeptides also include a polypeptide consisting of, or comprising the above noted polypeptides with the addition of up to 25, or alternatively 20, or alternatively 15, or alternatively up to 10, or alternatively up to 5 random amino acids on either the amine or carboxy termini (or on both). In another aspect, they equivalent polypeptide includes a polypeptide consisting of, or comprising the above noted polypeptides with the addition of up to 25, or alternatively 20, or alternatively 15, or alternatively up to 10, or alternatively up to 5 amino acids on either the amine or carboxy termini (or on both) selected from the adjacent amino acids of the corresponding wild-type sequence and equivalents of the wild-type adjacent amino acids.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins disclosed herein by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using a host cell and vector systems described herein.

Also provided by this application are the polypeptides described herein conjugated to a detectable agent for use in the diagnostic methods. For example, detectably labeled polypeptides can be bound to a column and used for the detection and purification of antibodies. They also are useful as immunogens for the production of antibodies as described below. The polypeptides disclosed herein are useful in an in vitro assay system to screen for agents or drugs, which modulate cellular processes.

It is well known to those skilled in the art that modifications can be made to the peptides disclosed herein to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides disclosed herein can be modified to include unnatural amino acids. Thus, the peptides may comprise D-amino acids, a combination of and L-amino acids, and various "designer" amino acids (e.g., .beta.-methyl amino acids, C-alpha-methyl amino acids, and N-alpha-methyl amino acids, etc.) to convey special properties to peptides. Additionally, by assigning specific amino acids at specific coupling steps, peptides with alpha-helices, beta. turns, beta. sheets, gamma-turns, and cyclic peptides can be generated. Generally, it is believed that.alpha.-helical secondary structure or random secondary structure may be of particular use.

The polypeptides disclosed herein also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of E. coli, mutant derivatives of cholera toxin, CPG oligonucleotides, and adjuvants derived from squalene.

This disclosure also provides a pharmaceutical composition comprising or alternatively consisting essentially of, or yet further consisting of, any of a polypeptide, analog, mutein, or fragment disclosed herein, alone or in combination with each other or other agents, such an antibiotic and an acceptable carrier or solid support. These compositions are useful for various diagnostic and therapeutic methods as described herein.

Polynucleotides

This disclosure also provides isolated or recombinant polynucleotides encoding one or more of the above-identified isolated or recombinant polypeptides and their respective complementary strands. Vectors comprising the isolated or recombinant polynucleotides are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides disclosed herein encode polypeptides or proteins having diagnostic and therapeutic utilities as described herein as well as probes to identify transcripts of the protein that may or may not be present. These nucleic acid fragments can by prepared, for example, by restriction enzyme digestion of larger polynucleotides and then labeled with a detectable marker. Alternatively, random fragments can be generated using nick translation of the molecule. For methodology for the preparation and labeling of such fragments, see, Sambrook et al. (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using known methods. See, Sambrook et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g., a mammalian cell, an animal cell (rat or mouse), a human cell, or a prokaryotic cell such as a bacterial cell, containing a polynucleotide encoding a protein or polypeptide or antibody.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

When the vectors are used for gene therapy in vivo or ex vivo, a pharmaceutically acceptable vector, such as a replication-incompetent retroviral or adenoviral vector, are exemplary (but non-limiting) and may be of particular use. Pharmaceutically acceptable vectors containing the nucleic acids disclosed herein can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) Bio-Techniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides disclosed herein. The genetically modified cells can be produced by insertion of upstream regulatory sequences such as promoters or gene activators (see, U.S. Pat. No. 5,733,761).

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide disclosed herein under conditions permitting hybridization (optionally moderately stringent hybridization conditions) of complementary single-stranded polynucleotides, or optionally, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al. (1989) supra. The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides disclosed herein also can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (199.4)) or MacPherson et al. (1991) and (1995) supra, and references cited therein. Alternatively, one of skill in the art can use the sequences provided herein and a commercial DNA synthesizer to replicate the DNA. Accordingly, this disclosure also provides a process for obtaining the polynucleotides disclosed herein by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the poly-nucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide disclosed herein are useful as hybridization probes or as an equivalent of the specific polynucleotides identified herein. Since the full coding sequence of the transcript is known, any portion of this sequence or homologous sequences can be used in the methods disclosed herein.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. In some embodiments, a probe useful for detecting the aforementioned mRNA is at least about 80% identical to the homologous region. In some embodiments, the probe is 85% identical to the corresponding gene sequence after alignment of the homologous region; in some embodiments, it exhibits 90% identity.

These probes can be used in radioassays (e.g., Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide disclosed herein. Accordingly, this disclosure also provides a probe comprising or corresponding to a polynucleotide disclosed herein, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally well suited, so as to increase stability and selectivity of the hybrid, and thereby improving the specificity of particular hybrid molecules obtained. In certain embodiments, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of *E. coli* DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively expression of the encoded polypeptide can be detected by various methods. In particular it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

Antibodies and Derivatives Thereof

This disclosure also provides an antibody that binds and/or specifically recognizes and binds an isolated polypeptide for use in the methods disclosed herein. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof. In one aspect, the fragment comprises, or alternatively consists essentially of, or yet further consists of the CDR of the antibody. In one aspect, the antibody is detectably labeled or further comprises a detectable label conjugated to it. Also provided is a hybridoma cell line that produces a monoclonal antibody disclosed herein. Compositions comprising or alternatively consisting essentially of or yet further, consisting of one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and described herein.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum.

Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses, e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest and then screened for the activity of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; and 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052; Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids or variable or contstant regions from other isotypes.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180,370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Pat. Application Publication No. 2006/0211088; PCT International Application Publication No. WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments ($V_H$-$C_H1$-VH-$C_H1$) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677,425) and amino acid mutations in the Fc hinge region to decrease the biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields, R. L. et al. (2002) J. Biol. Chem. 277:26733-26740; Umana et al. (1999) Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be PEGylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al. (1984) Anal. Biochem. 142:68-78); sulfhydral groups (Koyama (1994) Chem. Abstr. 120:217-262) of amino acid residues and carbohydrate groups (Rodwell et al. (1986) PNAS USA 83:2632-2636; Quadri et al. (1993) Nucl. Med. Biol. 20:559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chloramhucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins and mixed toxins.

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. 1994 Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995)).

Techniques for conjugating therapeutic agents to antibodies are well known (Amon et al. "Monoclonal Antibodies For Immunotargeting Of Drugs In Cancer Therapy," in Monoclonal Antibodies And Cancer Therapy; Reisfeld et al. (eds.), pp. 243-56 (Alan R. Liss, Inc. 1985); Hellstrom et al. "Antibodies For Drug Delivery," in Controlled Drug Delivery (2nd Ed.); Robinson et al. (eds.), pp. 623-53 (Marcel Dekker, Inc. 1987); Thorpe "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy," in Monoclonal Antibodies For Cancer Detection And Therapy, Baldwin et al. (eds.), pp. 303-16 (Academic Press 1985), and Thorpe et al. "The Preparation And Cytotoxic Properties Of Antibody-Toxin Conjugates," (1982) Immunol. Rev. 62:119-58).

The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or noncovalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al. (1984) J. Exp. Med. 160:1686; Liu et al. (1985) Proc. Natl. Acad. Sci. USA 82:8648). When the binding molecules are antibodies, they can be conjugated by sulfhydryl bonding of the C-terminus hinge regions of the two heavy chains.

The antibodies or fragments thereof of the present disclosure may be linked to a moiety that is toxic to a cell to which the antibody is bound to form "depleting" antibodies. These antibodies are particularly useful in applications where it is desired to deplete an NK cell.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

In some of the aspects of the antibodies provided herein, the antibody binds a DNABII protein with a dissociation constant ($K_D$) of less than $10^{-4}$M, $10^{-5}$M, $10^{-6}$ M, $10^{-7}$M, $10^{-8}$M, $10^{-9}$ M, $10^{-10}$ M, $10^{-11}$ M, or $10^{-12}$ M. In some of the aspects of the antibodies provided herein, the antigen binding site specifically binds to a DNABII protein.

In some of the aspects of the antibodies provided herein, the antibody is soluble Fab.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody is selected from the group consisting of Fab, F(ab)'2, Fab', scFv, and Fv.

In some of the aspects of the antibodies provided herein, the antibody comprises an Fc domain. In some of the aspects of the antibodies provided herein, the antibody is a non-human animal such as a rat, sheep, bovine, canine, feline or rabbit antibody. In some of the aspects of the antibodies provided herein, the antibody is a human or humanized antibody or is non-immunogenic in a human.

In some of the aspects of the antibodies provided herein, the antibody comprises a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families. 1) Amino acids with basic side chains: lysine, arginine, histidine. 2) Amino acids with acidic side chains: aspartic acid, glutamic acid. 3) Amino acids with uncharged polar side chains: asparagine, glutamine, serine, threonine, tyrosine. 4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind a DNABII protein with similar specificity and sensitivity profiles as the disclosed antibodies. This may be tested by way of the binding assays.

In a further aspect, the antibodies are characterized by being both immunodominant and immunoprotective, as determined using appropriate assays and screens.

Functional Analysis with Antibodies

Antibodies disclosed herein can be used to purify the polypeptides disclosed herein and to identify biological equivalent polypeptide and/or polynucleotides. They also can be used to identify agents that modify the function of the polypeptides disclosed herein. These antibodies include polyclonal antisera, monoclonal antibodies, and various reagents derived from these preparations that are familiar to those practiced in the art and described above.

Antibodies that neutralize the activities of proteins encoded by identified genes can also be used in vivo and in vitro to demonstrate function by adding such neutralizing antibodies into in vivo and in vitro test systems. They also are useful as pharmaceutical agents to modulate the activity of polypeptides disclosed herein.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

The antibodies disclosed herein may be used for vaccination or to boost vaccination, alone or in combination with peptides or protein-based vaccines or dendritic-cell based vaccines.

Compositions

Compositions are further provided. The compositions comprise a carrier and one or more of an isolated polypeptide disclosed herein, an isolated polynucleotide disclosed herein, a vector disclosed herein, an isolated host cell disclosed herein, a small molecule or an antibody or fragment thereof as disclosed herein. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide disclosed herein, an isolated polynucleotide disclosed herein, a vector disclosed herein, a small molecule, an isolated host cell disclosed herein, or an antibody of the disclosure, formulated with one or more pharmaceutically acceptable substances.

For oral preparations, any one or more of an isolated or recombinant polypeptide as described herein, an isolated or recombinant polynucleotide as described herein, a vector as described herein, an isolated host cell as described herein, a small molecule or an antibody as described herein can be used alone or in pharmaceutical formulations disclosed herein comprising, or consisting essentially of, the compound in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated polypeptide disclosed herein, an isolated polynucleotide disclosed herein, a vector disclosed herein, an isolated host cell disclosed herein, or an antibody or a fragment thereof as disclosed herein can be formulated into preparations for injection in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is a antimicrobial agent such as other vaccine components such as surface antigens, e.g., an OMP P5, OMP 26, OMP P2, or Type IV Pilin protein (see Jurcisek and Bakaletz (2007) J. of Bacteriology 189(10): 3868-3875 and Murphy, T F, Bakaletz, L O and Smeesters, P R (2009) The Pediatric Infectious Disease Journal, 28:S121-S126) and antibacterial agents. For intravenous administration, suitable carriers include physiological bacteriostatic water, Cremophor EL™ (BASF, Parsippany, N.J.), or phosphate buffered saline (PBS). In all cases, a composition for parenteral administration must be sterile and should be fluid to the extent that easy syringability exists.

Aerosol formulations provided by the disclosure can be administered via inhalation and can be propellant or non-propellant based. For example, embodiments of the pharmaceutical formulations disclosed herein comprise a compound disclosed herein formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself, e.g., by an elastic bladder).

Suppositories disclosed herein can be prepared by mixing a compound disclosed herein with any of a variety of bases such as emulsifying bases or water-soluble bases. Embodiments of this pharmaceutical formulation of a compound disclosed herein can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds disclosed herein. Similarly, unit dosage forms for injection or intravenous administration may comprise a compound disclosed herein in a composition as a solution in sterile water, normal saline or another pharmaceutically acceptable carrier.

Embodiments of the pharmaceutical formulations disclosed herein include those in which one or more of an isolated polypeptide disclosed herein, an isolated polynucleotide disclosed herein, a vector disclosed herein, a small molecule for use in the disclosure, an isolated host cell disclosed herein, or an antibody disclosed herein is formulated in an injectable composition. Injectable pharmaceutical formulations disclosed herein are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations disclosed herein.

In an embodiment, one or more of an isolated polypeptide disclosed herein, an isolated polynucleotide disclosed herein, a vector disclosed herein, an isolated host cell disclosed herein, or an antibody or fragment thereof as disclosed herein is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound disclosed herein can be accomplished using any of a variety of refillable, pump systems. Pumps provide consistent, controlled release over time. In some embodiments, a compound disclosed herein is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852; and the like. In general, a subject treatment method can be accomplished using any of a variety of refillable, non-exchangeable pump systems. Pumps and other convective systems may be utilized due to their generally more consistent, controlled release over time. Osmotic pumps are used in some embodiments due to their combined advantages of more consistent controlled release and relatively small size (see, e.g., PCT International Application Publication No. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a compound disclosed herein are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylatanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the agent (as well as combination compositions) is delivered in a controlled release system. For example, a compound disclosed herein may be administered using intravenous infusion, an implantable osmotic pump, a transdermal patch, liposomes, or other modes of administration. In one embodiment, a pump may be used (Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990) Science 249:1527-1533.

In another embodiment, the compositions of the present disclosure (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The present disclosure provides methods and compositions for the administration of a one or more of a polyeptide, a polynucleotide, a vector, a host cell, an antibody or a fragment thereof to a host (e.g., a human) for the treatment of a microbial infection. In various embodiments, these methods disclosed herein span almost any available method and route suitable for drug delivery, including in vivo and ex vivo methods, as well as systemic and localized routes of administration.

Vaccine Compositions

This disclosure also provides compositions and methods of eliciting in an individual an immune response that disrupts a biofilm and/or prevent or treat an infection associated with a biofilm. In certain aspects, the methods elicit an immune response to the chimeric proteins of the invention. These methods elicit one or more immune responses, including but not limited to, immune responses which provide the therapeutidc responses disclosed herein. In one embodiment, the methods comprise a step of administering an immunogenic dose of a polypeptide composition as described herein. In another embodiment, the methods comprise administering an immunogenic dose of a polynucleotide encoding the polypeptide, the vector or host cells as described herein. The methods may be used in combination in a single individual. The methods may be used prior or subsequent to infection of an individual harboring an infection that will lead to a biofilm. The methods and compositions of the disclosure can be used to treat or prevent any pathological condition associated with a biofilm non-limiting examples of such include for example, OM, sinusitis, septicemia, and cystic fibrosis.

In one aspect, one or more compositions of the disclosure is administered as a priming dose followed by one or more booster doses. Co-administration of proteins or polypeptides that beneficially enhance the immune response such as cytokines (e.g., IL-2, IL-12, GM-CSF), cytokine-inducing molecules (e.g. Leaf) or co-stimulatory molecules is also contemplated.

An "immunogenic dose" of a composition of the invention is one that generates, after administration, a detectable humoral (antibody) and/or cellular (T cell) immune response in comparison to the immune response detectable before administration or in comparison to a standard immune response before administration. The invention contemplates that the immune response resulting from the methods may be protective and/or therapeutic. In a preferred embodiment, the antibody and/or T cell immune response protects the individual from an infection that leads to biofilm formation and/or disrupts a biofilm. The precise dose depends on the patient's state of health and weight, the mode of administration, the nature of the formulation, etc., but generally ranges from about 1.0 microgram to about 5000 microgram per 70 kilogram patient, more commonly from about 10 to about 500 microgram per 70 kg of body weight.

Humoral immune response may be measured by many well known methods, such as Single Radial Immunodiffusion Assay (SRID), Enzyme Immunoassay (ETA) and Hemagglutination Inhibition Assay (HAI). In particular, SRID utilizes a layer of a gel, such as agarose, containing the immunogen being tested. A well is cut in the gel and the serum being tested is placed in the well. Diffusion of the antibody out into the gel leads to the formation of a precipitation ring whose area is proportional to the concentration of the antibody in the serum being tested. EIA, also known as ELISA (Enzyme Linked Immunoassay), is used to determine total antibodies in the sample. The immunogen is adsorbed to the surface of a microtiter plate. The test serum is exposed to the plate followed by an enzyme linked immunoglobulin, such as IgG. The enzyme activity adherent to the plate is quantified by any convenient means such as spectrophotometry and is proportional to the concentration of antibody directed against the immunogen present in the test sample. HAI utilizes the capability of an immunogen such as viral proteins to agglutinate chicken red blood cells (or the like). The assay detects neutralizing antibodies, i.e., those antibodies able to inhibit hemagglutination. Dilutions of the test serum are incubated with a standard concentration of immunogen, followed by the addition of the red blood cells. The presence of neutralizing antibodies will inhibit the agglutination of the red blood cells by the immunogen. Tests to measure cellular immune response include determination of delayed-type hypersensitivity or measuring the proliferative response of lymphocytes to target immunogen.

Thus, in one aspect, the disclosure provides compositions suitable for eliciting an immune response to the polypeptides. As noted above, the compositions comprise one or more chimeric proteins, cells expressing one or more chimeric proteins, or one or more polynucleotides encoding one or more chimeric proteins. The compositions may also comprise other ingredients such as carriers and adjuvants.

In compositions of the disclosure, a chimeric polypeptide can be fused to another protein when produced by recombinant methods. In one embodiment, the other protein may not, by itself, elicit antibodies, but it stabilizes the first protein and fauns a fusion protein retaining immunogenic activity. In another embodiment, the fusion protein comprises another protein that is immunogenic, such as Glutathione-S-transferase (GST) or beta-galactosidase, relatively large co-proteins which solubilize the fusion protein and facilitate production and purification thereof. The other protein may act as an adjuvant in the sense of providing a generalized stimulation of the immune system. The other protein may be fused to either the amino or carboxy terminus of the chimeric proteins as disclosed herein.

In sum aspects, the polypeptides can be linked to carrier substances. Any method of creating such linkages known in the art may be used. Linkages can be formed with heterobifunctional agents that generate a disulfide link at one functional group end and a peptide link at the other, such as a disulfide amide forming agent, e.g., N-succidimidyl-3-(2-pyridyldithio) proprionate (SPDP) (See, e.g., Jansen et al., Immun. Rev. 62:185, 1982) and bifunctional coupling agents that form a thioether rather than a disulfide linkage such as reactive esters of 6-maleimidocaproic acid, 2-bromoacetic acid, 2-iodoacetic acid, 4-(N-maleimido-methyl) cyclohexane-1-carboxylic acid and the like, and coupling agent which activate carboxyl groups by combining them with succinimide or 1-hydroxy-2-nitro-4-sulfonic acid, for sodium salt such as succinimmidyl 4-(N-maleimido-methyl) cyclohexane-1-carobxylate (SMCC).

The polypeptides can be formulated as neutral or salt forms. Pharmaceutically acceptable salts, include the acid addition salts (formed with the free amino groups of the peptide) and which are formed with inorganic acids such as, e.g., hydrochloric or phosphoric acids, or such organic acids as acetic, oxalic, tartaric, mandelic. Salts formed with the free carboxyl groups may also be derived from inorganic bases such as, e.g., sodium, potassium, ammonium, calcium, or ferric hydroxides, and such organic bases as isopropylamine, trimethylamine, 2-ethylamino ethanol, histidine, and procaine.

The compositions of this disclosure can further comprise adjuvants. Known adjuvants include, for example, emulsions such as Freund's Adjuvants and other oil emulsions, *Bordetella pertussis*, MF59, purified saponin from *Quillaja saponaria* (QS21), aluminum salts such as hydroxide, phosphate and alum, calcium phosphate, (and other metal salts), gels such as aluminum hydroxide salts, mycobacterial products including muramyl dipeptides, solid materials, particles such as liposomes and virosomes. Examples of natural and bacterial products known to be used as adjuvants include monophosphoryl lipid A (MPL), RC-529 (synthetic MPL-like acylated monosaccharide), OM-174 which is a lipid A derivative from *E. coli*, holotoxins such as cholera toxin (CT) or one of its derivatives, pertussis toxin (PT) and heat-labile toxin (LT) of *E. coli* or one of its derivatives, and CpG oligonucleotides. Adjuvant activity can be affected by a number of factors, such as carrier effect, depot formation, altered lymphocyte recirculation, stimulation of T-lymphocytes, direct stimulation of B-lymphocytes and stimulation of macrophages.

The compositions of the disclosure are typically formulated as injectables, either as liquid solutions or suspensions; solid forms suitable for solution in, or suspension in, liquid prior to injection may also be prepared. The preparation may also be emulsified. The active immunogenic ingredient is often mixed with excipients, which are pharmaceutically acceptable and compatible with the active ingredient. Suitable excipients are, e.g., water, saline, dextrose, glycerol, ethanol, or the like and combinations thereof. In addition, if desired, the vaccine may contain minor amounts of auxiliary substances such as wetting or emulsifying agents, pH buffering agents, or adjuvants, which enhance the effectiveness of the vaccine. The vaccines are conventionally administered parenterally, by injection, for example, either subcutaneously or intramuscularly.

Additional formulations which are suitable for other modes of administration include suppositories and, in some cases, oral formulations. For suppositories, traditional binders and carriers may include, for example, polyalkene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10%-95% of active ingredient, preferably 25-70%.

Compositions may also be administered through transdermal routes utilizing jet injectors, microneedles, electroporation, sonoporation, microencapsulation, polymers or liposomes, transmucosal routes and intranasal routes using nebulizers, aerosols and nasal sprays. Microencapsulation using natural or synthetic polymers such as starch, alginate and chitosan, D-poly L-lactate (PLA), D-poly DL-lactic-coglycolic microspheres, polycaprolactones, polyorthoesters, polyanhydrides and polyphosphazenes polyphosphatazanes are useful for both transdermal and transmucosal administration. Polymeric complexes comprising synthetic poly-ornithate, poly-lysine and poly-arginine or amphipathic peptides are useful for transdermal delivery systems. In addition, due to their amphipathic nature, liposomes are contemplated for transdermal, transmucosal and intranasal vaccine delivery systems. Common lipids used for vaccine delivery include N-(1)2,3-(dioleyl-dihydroxypropyl)-N,N,N,-trimethylammonium-methyl sulfate (DOTAP), dioleyloxy-propyl-trimethylammonium chloride DOTMA, dimystyloxypropyl-3-dimethyl-hydroxyethyl ammonium (DMRIE), dimethyldioctadecyl ammonium bromide (DDAB) and 9N(N',N-dimethylaminoethane) carbamoyl) cholesterol (DC-Chol). The combination of helper lipids and liposomes will enhance up-take of the liposomes through the skin. These helper lipids include dioleoyl phosphatidylethanolamine (DOPE), dilauroylphosphatidylethanolamine (DLPE), dimyristoyl phosphatidylethanolamine (DMPE), dipalmitoylphosphatidylethanolamine (DPPE). In addition, triterpenoid glycosides or saponins derived from the Chilean soap tree bark (*Quillaja saponaria*) and chitosan (deacetylated chitan) have been contemplated as useful adjuvants for intranasal and transmucosal vaccine delivery.

Formulations can be presented in unit-dose or multi-dose containers, for example, sealed ampules and vials and may be stored in a freeze-dried condition requiring only the addition of the sterile liquid carrier immediately prior to use.

Screening Assays

The present disclosure provides methods for screening for equivalent agents, such as equivalent monoclonal antibodies to a polyclonal antibody as described herein and various agents that modulate the activity of the active agents and pharmaceutical compositions disclosed herein or the function of a polypeptide or peptide product encoded by the polynucleotide disclosed herein. For the purposes of this disclosure, an "agent" is intended to include, but not be limited to a biological or chemical compound such as a simple or complex organic or inorganic molecule, a peptide, a protein (e.g., antibody), a polynucleotide antisense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

Certain embodiments relate to a method for screening small molecules capable of interacting with a polypeptide, antibody or fragment thereof disclosed herein. For the purpose of this disclosure, "small molecules" are molecules having low molecular weights (MW) that are, in one embodiment, capable of binding to a protein of interest thereby altering the function of the protein. In some embodiments, the MW of a small molecule is no more than 1,000. Methods for screening small molecules capable of altering protein function are known in the art. For example, a miniaturized arrayed assay for detecting small molecule-protein interactions in cells is discussed by You et al. (1997) Chem. Biol. 4:961-968.

To practice the screening method in vitro, suitable cell culture or tissue infected with the microbial to be treated are first provided. The cells are cultured under conditions (temperature, growth or culture medium and gas ($CO_2$)) and for an appropriate amount of time to attain exponential proliferation without density dependent constraints. It also is desirable to maintain an additional separate cell culture that is not infected as a control.

As is apparent to one of skill in the art, suitable cells can be cultured in micro-titer plates and several agents can be assayed at the same time by noting genotypic changes, phenotypic changes or a reduction in microbial titer.

When the agent is a composition other than a DNA or RNA, such as a small molecule as described above, the agent can be directly added to the cell culture or added to culture medium for addition. As is apparent to those skilled in the art, an "effective" amount must be added which can be empirically determined, When the agent is an antibody or antigen binding fragment, the agent can be contacted or incubated with the target antigen and polyclonal antibody as described herein under conditions to perform a competitive ELISA. Such methods are known to the skilled artisan.

The assays also can be performed in a subject. When the subject is an animal such as a rat, chinchilla, mouse or simian, the method provides a convenient animal model system that can be used prior to clinical testing of an agent in a human patient. In this system, a candidate agent is a potential drug if symptoms of the disease or microbial infection is reduced or eliminated, each as compared to untreated, animal having the same infection. It also can be useful to have a separate negative control group of cells or animals that are healthy and not treated, which provides a basis for comparison.

The agents and compositions can be used in the manufacture of medicaments and for the treatment of humans and other animals by administration in accordance with conventional procedures, such as an active ingredient in pharmaceutical compositions.

Combination Therapy

The compositions and related methods of the present disclosure may be used in combination with the administration of other therapies. These include, but are not limited to, the administration of DNase enzymes, antibiotics, antimicrobials, or other antibodies.

In some embodiments, the methods and compositions include a deoxyribonuclease (DNase) enzyme that acts synergistically with the anti-DNABII antibody. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective Unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current disclosure include amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0, 30, 0, 35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (i.e., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formation or as a separate formulation.

Formulations and Co-Formulations

The disclosure provided herein contemplates specific formulations and co-formulations of the agents disclosed herein along with a pharmaceutically acceptable excipient, such as those disclosed herein above.

In specific aspects, the disclosure provides for formulations or co-formulations comprising antibodies or antigen binding fragments thereof that specifically recognize or bind an isolated or recombinant polypeptides. Antibodies disclosed herein may be selected such that they have a high level of epitope binding specificity and high binding affinity to the biofilm. In general, the higher the binding affinity of an antibody, the more stringent wash conditions can be performed in an immunoassay to remove nonspecifically bound material without removing the target. Accordingly, the antibodies of the present technology useful in the disclosed methods usually have binding affinities of at least $10^{-6}$, $10^{-7}$, $10^{-8}$, $10^{-9}$, $10^{-10}$, $10^{-11}$, or $10^{-12}$ M. In certain aspects, the antibodies have a sufficient kinetic on-rate to reach equilibrium under standard conditions in at least 12 hours, at least 5 hours, at least 1 hour, or at least 30 minutes. In another aspect, the affinity of the antibody or antigen binding fragment is less than or about 1000 picoMole (pM), 900 pM, 800 pM, 700 pM, 600 pM, 500 pM, 400 pM, 300 pM, 200 pM, about 100 pM, 50 pM, 40 pM, 30 pM, 20 pM, 10 pM, 9 pM, 8 pM, 7 pM, 6 pM, 5 pM, or 4 pM.

In some embodiments, the antibodies or antigen binding fragments thereof are present in the formulation at a concentration from about 0.1 mg/mL to about 200 mg/mL, or alternatively from about 1 to about 150 mg/mL, or alternatively about 2 mg/mL to about 100 mg/mL, or alternatively about 3 mg/mL to about 80 mg/mL, or alternatively about 4 mg/mL to about 50 mg/mL, or alternatively about 5 mg/mL to about 20 mg/mL. In some embodiments, the antibodies are present at a concentration of at least about 1 mg/mL, or alternatively at least about 2 mg/mL, at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL or alternatively at least about 200 mg/mL. In some embodiments, at least one of the plurality of antibodies is present at a concentration of at least about 1 mg/mL, or alternatively at least about 2 mg/mL, or alternatively at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL, or alternatively at least about 200 mg/mL.

In some embodiments, wherein multiple different antibodies are included an antibody co-formulation, the different antibodies may be present in substantially equal concentrations. In another aspect of such embodiments, the different antibodies one or more of the antibodies may be present in a substantially higher concentration than the other antibodies, e.g., ratios of about 1.5:1, or alternatively about 1.5:1:1, or alternatively about 1.5:1:1:1, or alternatively about 2:1, or alternatively about 2:1:1, or alternatively about 2:1:1:1, or alternatively at least about 2.5:1, or alternatively at least about 2.5:1:1, or alternatively at least about 2.5:1:1:1.

In some embodiments the co-formulation comprises, or alternatively consists essentially of, or yet further comprises an antibody that specifically recognizes or binds an isolated or recombinant polypeptide consisting essentially of a two or more of A5 a fragment or equivalent thereof (e.g., in duplicate or in combination with another such as mB4) or two or more of mB4 polypeptide, a fragment or equivalent thereof or mB4 in combination with A5, a fragment or an equivalent of each thereof. In some embodiments, one or more antibodies in the formulation is not a polyclonal antibody. In some embodiments, this formulation is used as a therapeutic.

In some embodiments the co-formulation comprises, or alternatively consists essentially of, or yet further comprises an antibody that specifically recognizes or binds an isolated or recombinant polypeptide consisting essentially of two or more of A1 to A4 or A6 or B1 to B6, or a fragment or equivalent thereof. In some embodiments, one or more antibodies in the formulation is not a polyclonal antibody. In some embodiments, this formulation is used as a diagnostic.

Methods of stably formulating antibody formulations and co-formulations can be made according to techniques disclosed in the art—see, e.g., U.S. Pat. Publication No. US 2011/0059079.

Diagnostic and Therapeutic Methods

Also provided are methods for inhibiting, competing or titrating the binding of a DNABII polypeptide or protein to a microbial DNA, by contacting the DNABII polypeptide or protein or the microbial DNA with a composition as described herein. In a further aspect, the DNABII polypeptide and the microbial DNA are detectably labeled, for example with luminescent molecules that will emit a signal when brought into close contact with each other. The contacting can be performed in vitro or in vivo.

In another aspect, a method for inhibiting, dissolving, preventing or breaking down a microbial biofilm is provided by contacting the biofilm with an agent or composition as described herein. In a further aspect, the DNABII polypeptide and the microbial DNA are detectably labeled, for example with luminescent molecules that will emit a signal when brought into close contact with each other. The contacting can be performed in vitro or in vivo.

When practiced in vitro, the methods are useful to screen for or confirm agents having the same, similar or opposite ability as the polypeptides, polynucleotides, antibodies or fragments thereof, host cells, small molecules and compositions disclosed herein. Alternatively, they can be used to identify which agent is best suited to treat a microbial infection. For example, one can screen for new agents or combination therapies by having two samples containing for example, the DNABII polypeptide and microbial DNA and the agent to be tested. The second sample contains the DNABII polypeptide and microbial DNA and an agent known to active, e.g., an anti-IHF antibody or a small molecule to serve as a positive control. In a further aspect, several samples are provided and the agents are added to the system in increasing dilutions to determine the optimal dose that would likely be effective in treating a subject in the clinical setting. As is apparent to those of skill in the art, a negative control containing the DNABII polypeptide and the microbial DNA can be provided. In a further aspect, the DNABII polypeptide and the microbial DNA are detectably labeled, for example with luminescent molecules that will emit a signal when brought into close contact with each other. The samples are contained under similar conditions for an effective amount of time for the agent to inhibit, compete or titrate the interaction between the DNABII polypeptide and microbial DNA and then the sample is assayed for emission of signal from the luminescent molecules. If the sample emits a signal, then the agent is not effective to inhibit binding.

In another aspect, the in vitro method is practiced in a miniaturized chamber slide system wherein the microbial (such as a bacterial) isolate causing an infection could be isolated from the human/animal then cultured to allow it to grow as a biofilm in vitro, see for example experiments below. The agent (such as anti-IHF antibody) or potential agent is added alone or in combination with another agent to the culture with or without increasing dilutions of the potential agent or agent such as an anti-IHF (or other antibody, small molecule, agent, etc.) to find the optimal dose that would likely be effective at treating that patient when delivered to the subject where the infection existed. As apparent to those of skill in the art, a positive and negative control can be performed simultaneously.

In a further aspect, the method is practiced in a high throughput platform with the agent (such as anti-IHF antibody) and/or potential agent (alone or in combination with another agent) in a flow cell. The agent (such as anti-IHF antibody) or potential agent is added alone or in combination with another agent to the culture with or without increasing dilutions of the potential agent or agent such as an anti-IHF (or other antibody, small molecule, agent, etc.) to find the optimal dose that would likely be effective at treating that patient when delivered to the subject where the infection existed. Biofilm isolates are sonicated to separate biofilm bacteria from DNABII polypeptide such as IHF bound to microbial DNA. The DNABII polypeptide—DNA complexes are isolated by virtue of the anti-IHF antibody on the platform. The microbial DNA is then be released with e.g., a salt wash, and used to identify the biofilm bacteria added. The freed DNA is then identified, e.g., by PCR sequenced. If DNA is not freed, then the agent(s) successfully performed or bound the microbial DNA. If DNA is found in the sample, then the agent did not interfere with DNABII polypeptide-microbial DNA binding. As is apparent to those of skill in the art, a positive and/or negative control can be simultaneously performed.

In another aspect one or more of the agents or antibodies disclosed herein are used in a method of detecting a biofilm in vivo. In further embodiments, the agents or antibodies are detectably labeled, for example with a luminescent or fluorescent molecule. Further applications of the methods disclosed herein include methods of use of such agents or antibodies to image a biofilm using, for example, a detectably labeled primary agent or antibody which provides a detectable signal upon binding to the biofilm or a detectably labeled secondary antibody which binds to the primary agent or antibody when it is bound to the biofilm.

The above methods also can be used as a diagnostic test since it is possible that a given bacterial species will respond better to reversal of its biofilm by one agent more than another, this rapid high throughput assay system could allow one skilled the art to assay a panel of possible agents to identify the most efficacious of the group.

The advantage of these methods is that most clinical microbiology labs in hospitals are already equipped to perform these sorts of assays (i.e., determination of MIC, MBC values) using bacteria that are growing in liquid culture (or planktonically). As is apparent to those of skill in die art, bacteria generally do not grow planktonically when they are causing diseases. Instead they are growing as a stable biofilm and these biofilms are significantly more resistant to treatment by antibiotics, antibodies or other therapeutics. This resistance is why most MIC/MBC values fail to accurately predict efficacy in vivo. Thus, by determining what "dose" of agent could reverse a bacterial biofilm in vitro (as described above) Applicants' pre-clinical assay would be a more reliable predictor of clinical efficacy, even as an application of personalized medicine.

In addition to the clinical setting, the methods can be used to identify the microbe causing the infection and/or confirm effective agents in an industrial setting.

In a further aspect of the above methods, an antibiotic or antimicrobial known to inhibit growth of the underlying infection is added sequentially or concurrently, to determine if the infection can be inhibited. It is also possible to add the agent to the microbial DNA or DNABII polypeptide before adding the complex to assay for biofilm inhibition.

When practiced in vivo in non-human animal such as a chinchilla, the method provides a pre-clinical screen to identify agents that can be used alone or in combination with other agents to break down biofilms.

In another aspect, provided herein is a method of inhibiting, dissolving preventing or breaking down a biofilm in a subject by administering to the subject an effective amount of a polypeptide, polynucleotide, vector, host cell, antibody or antigen binding fragment thereof, thereby inhibiting, preventing, dissolving or breaking down the microbial biofilm.

Alternatively or additionally, methods of inhibiting, dissolving preventing or breaking down a biofilm may be practiced in vitro and/or ex vivo and involve providing a sample of the biofilm—taken from a subject or generated in vitro—and administering an effective amount of a polypeptide, polynucleotide, vector, host cell, antibody or antigen binding fragment thereof, thereby inhibiting, preventing or breaking down the microbial biofilm. Similarly, the compositions disclosed herein may be used in method embodiments for inhibiting, preventing, or breaking down microbial biofilms on surfaces colonized by biofilms such as, but not limited to, hospital instruments, industrial equipment, and other materials not comprised of living tissue.

In some embodiments the methods disclosed herein comprise, or alternatively consist essentially of, or yet further comprise, administering one or more of a polypeptide, polynucleotide, vector, host cell, antibody or antigen binding fragment thereof, alone or in combination. In further embodiments of the disclosed methods, the agents may be administered simultaneously. In alternative embodiments, the antibodies are administered sequentially.

Also provided herein is a method for inducing an immune response in or conferring passive immunity on subject in need thereof, comprising, or alternatively consisting essentially of, or yet further consisting of, administering to the subject an effective amount of one or more of a polypeptide, polynucletide, vector, host cell, antibody or antigen binding fragment thereof as disclosed herein.

In some embodiments, the antibody or antigen binding fragment is not a polyclonal antibody.

In a further aspect, the methods further comprise, or alternatively consist essentially of, or yet further consist of administering to the subject an effective amount of one or more of an antimicrobial, an antigenic peptide or an adjuvant.

A non-limiting example of an antimicrobial agent are antibodies directed against vaccine component such as a surface antigen, e.g., an OMP P5, rsPilA, OMP 26, OMP P2, or Type IV Pilin protein (see Jurcisek and Bakaletz (2007) J. Bacteriology 189(10):3868-3875; Murphy et al. (2009) The Pediatric Infectious Disease Journal 28:S121-S126; Novotny et al. (2015) Mol Microbiol. 96(2):276-92).

The agents and compositions disclosed herein can be concurrently or sequentially administered with other antimicrobial agents and/or surface antigens. In one particular aspect, administration is locally to the site of the infection by direct injection or by inhalation for example. Other non-limiting examples of administration include by one or more method comprising transdermally, urethrally, sublingually, rectally, vaginally, ocularly, subcutaneous, intramuscularly, intraperitoneally, intranasally, by inhalation or orally.

Microbial infections and disease that can be treated by the methods disclosed herein include but are not limited to infection by various organisms associated with biofilm formation, including but not limited to those disclosed in the examples. Non-limiting examples of relevant organisms (and exemplary strains thereof in parentheses) include: *Aggregatibacter actinomycetemcomitans*, *Borrelia burgdorferi* (e.g., B31), *Bordetella pertussis* (e.g., Tohama I), *Burkholderia pseudomallei* (e.g., 668), *Burkholderia cenocepacia* (e.g., HI2424), *Escherichia coli* (e.g., K12 MG1655), *Enterococcus faecalis* (e.g., V583), *Haemophilus influenzae* (e.g., Rd KW20), *Helicobacter pylori* (e.g., 26695), *Klebsiella pneumoniae*, *Moraxella catarrhalis* (e.g., RH4), *Mycobacterium smegmatis* (e.g., MC2), *Mycobacterium tuberculosis* (e.g., CDC1551), *Neisseria gonorrhoeae* (e.g., FA1090), *Neisseria meningitidis* (e.g., MC58), *Pseudomonas aeruginosa*, *Porphyromonas gingivalis* (e.g., W83), *Prevotella intermedia* (e.g., 17), *Prevotella melaninogenica* (e.g., ATCC (ID 25845), *Staphylococcus aureus* (e.g., MW2), *Staphylococcus epidermidis* (e.g., RP62A), *Streptococcus agalactiae* (e.g., 2603V/R), *Streptococcus bovis*, *Streptococcus gallolyticus* (e.g., UCN34), *Streptococcus gordonii* (e.g., NCTC 7868 (Challis)), *Streptococcus mutans* (e.g., UA159), *Streptococcus pneumoniae* (e.g., R6), *Streptococcus pyogenes* (e.g., MGAS10270), *Streptococcus sobrinus* (e.g., 6715), *Salmonella enterica* (e.g., *typhi*, CT18), *Treponema denticola* (e.g., ATCC® 35405), *Treponema palladum* (e.g., Nichols), and *Vibrio cholera* (e.g., El Tor, N16961). Additional organisms known to associate with and/or form biofilms include but are not limited to *Campylobacter* spp., *Candida* spp., *Legionella pneumophila*, and *Listeria monocytogenes*. For example, cystic fibrosis patients have *Pseudomonas* infections that often result in antibiotic resistant biofilms. Exemplary diseases associated with biofilms include, but are not limited to, lung infections of cystic fibrosis patients, otitis media, native valve infectious endocarditis, osteomyelitis, rhinosinusitis, prostatitis, recurrent urinary tract infection, wounds, dental caries and periodontitis. Conditions such as an infected artificial device, joint, catheter, stent or other surgical implant are also associated with biofilm formation.

These microbial infections may be present in the upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP). Thus, by practicing the in vivo methods disclosed herein, these diseases and complications from these infections can also be prevented or treated.

Infections might also occur in the oral cavity (caries, periodontitis) and caused by *Streptococcus mutans, Porphyromonas gingivalis, Aggregatibacter actinomycetemcomitans*. Infections might also be localized to the skin (abscesses, 'staph' infections, impetigo, secondary infection of burns, Lyme disease) and caused by *Staphylococcus aureus, Staphylococcus epidermidis, Pseudomonas aeruginosa* and *Borrelia* burdorferi. Infections of the urinary tract (UTI) can also be treated and are typically caused by *Escherichia coli*. Infections of the gastrointestinal tract (GI) (diarrhea, cholera, gall stones, gastric ulcers) are typically caused by *Salmonella enterica* serovar, *Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements, or dental implants, or medical devices such as pumps, catheters, stents, or monitoring systems, typically caused by a variety of bacteria, can be treated by the methods disclosed herein. These devices can be coated or conjugated to an agent as described herein. Thus, by practicing the in vivo methods disclosed herein, these diseases and complications from these infections can also be prevented or treated.

Infections caused by *Streptococcus agalactiae* can also be treated by the methods disclosed herein and it is the major cause of bacterial septicemia in newborns. Infections caused by *Neisseria meningitidis* which can cause meningitis can also be treated.

Thus, routes of administration applicable to the methods disclosed herein include intranasal, intramuscular, urethrally, intratracheal, subcutaneous, intradermal, topical application, intravenous, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In general, routes of administration suitable for the methods disclosed herein include, but are not limited to, direct injection, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The agents disclosed herein can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods disclosed herein, the agent will be administered by inhalation, injection or orally on a continuous, daily basis, at least once per day (QD), and in various embodiments two (BID), three (TID), or even four times a day. Typically, the therapeutically effective daily dose will be at least about 1 mg, or at least about 10 mg, or at least about 100 mg, or about 200—about 500 mg, and sometimes, depending on the compound, up to as much as about 1 g to about 2.5 g.

This disclosure provides methods and compositions to inhibit, prevent, or treat infection of a host or host cell by a bacteria that releases an DNABII protein, the methods and compositions comprising, or alternatively consisting essentially of, or yet further consisting of, administering to a tissue exposed to or infected with the bacteria an effective amount of a polypeptide, polynucleotide, vector, host cell, antibody or antigen binding fragment thereof, thereby inhibiting, preventing, or treating infection of the host or host cell by the bacteria. The antibody can be polyclonal, monoclonal or a derivative of an antibody that recognizes and binds the bacteria-relevant DNABII protein, as well as fragments thereof, e.g., a Fab fragment. Multiple antibodies or fragments thereof can be administered concurrently or sequentially along with supporting therapies as noted herein.

This disclosure provides a method to inhibit or prevent infection of a cell by a bacteria that releases an DNABII protein. The method comprises, or alternatively consists essentially of, or yet further consists of, administering to a tissue infected with the bacteria an effective amount of a polypeptide, polynucleotide, vector, host cell, antibody or antigen binding fragment thereof, thereby inhibiting or preventing infection of the bacteria. The source of antibody against the DNABII proteins can be elicited by either active vaccination of the host with the polypeptide as described herein or passive transfer of antiserum or an antibody against proteins of the DNABII protein as disclosed herein. The antibody can be polyclonal, monoclonal or a derivative of an antibody that recognizes and binds the bacteria-relevant DNABII protein. Multiple antibodies can be administered concurrently or sequentially along with supporting therapies as noted herein.

In some embodiments, the antibody is not a polyclonal antibody.

The administration can be in vitro in a culture or in vivo, by administration to a patient infected with the bacteria. When practiced in vivo, the method can be used to treat a subject infected with the bacteria by administering to the infected subject an effective amount of the antibody. In addition, when the subject is a non-human animal, the method can be used to test possible therapies or combination therapies prior to administration to a human. When practiced in vitro, the method is useful to screen for other therapeutic agents and combination therapies, such as small molecule drugs, that inhibit or prevent infection of the bacteria in a tissue.

Also provided are methods to treat a bacterial infection in subject in need thereof, wherein the subject is infected with a bacteria that comprises an DNABII protein, the method comprising, or alternatively consisting essentially of, or yet further consisting of, administering to the subject an effective amount of a polypeptide, polynucleotide, vector, host cell, antibody or antigen binding fragment thereof, thereby inhibiting or preventing infection by the bacteria. The antibody can be polyclonal, monoclonal or a derivative of an antibody that recognizes and binds the bacteria-relevant DNABII protein. The source of antibody against the DNABII protein can be elicited by either active vaccination of the host with the polynucleotide or passive transfer of antiserum or an antibody against the polypeptides disclosed herein. Multiple antibodies can be administered concurrently or sequentially along with supporting therapies as noted herein.

In some embodiments, the antibody is not a polyclonal antibody.

Yet further provided are methods to treat a condition in a subject in need thereof, wherein the condition is associated with a bacterial infection wherein the bacteria expresses an DNABII protein, the method comprising, or alternatively consisting essentially of, or yet further consisting of, administering to the subject an effective amount of a polypeptide, polynucletide, vector, host cell, antibody or antigen binding fragment thereof, thereby inhibiting or preventing infection of the bacteria. The source of antibody against the DNABII protein can be elicited by either active vaccination of the host with a polypeptide as disclosed herein or passive transfer of antiserum or an antibody or fragment thereof against the DNABII polypeptide as disclosed herein. The antibody can be polyclonal, monoclonal or a derivative of an antibody that recognizes and binds the bacteria-relevant DNABII protein. Multiple antibodies can be administered concurrently or sequentially along with supporting therapies as noted herein.

In some embodiments, the antibody is not a polyclonal antibody.

Any of the above methods can further comprise, or alternatively consist essentially of, or yet further consist of, administering to the subject or the tissue or cell culture in vitro, an effective amount of one or more of an antimicrobial, an antigenic peptide or an adjuvant. The subject, in some aspects, is a non-human animal or a human patient.

The antibody, antigen binding fragment thereof, polypeptide or composition is administered locally or systemically by any appropriate method, e.g., to the site of infection or biofilm, topically, rectally, vaginally, ocularly, subcutaneous, intramuscularly, intraperitoneally, urethrally, intranasally, by inhalation or orally.

In some aspects, the subject is a pediatric patient and the antibody is administered in a formulation for the pediatric patient.

A screen to identify potential therapeutic agents that inhibit or prevent infection of a cell by a bacteria that exports a DNABII protein and/or that disrupt or prevent biofilm formation is also disclosed. The screening method comprises, or alternatively consists essentially of, or yet consists of, contacting in vitro or administering in vivo to a tissue infected with the bacteria an agent and determining if the agent binds the DNABII protein. Methods to determining binding are known in the art and several non-limiting examples are described herein. In one aspect, if the agent binds the protein, the agent is a potential therapeutic agent and if the agent does not bind the protein, the agent is not a potential therapeutic agent. In another aspect, if the infection or biofilm is inhibited, disrupted, or prevented in vivo, the agent is a potential therapeutic agent and if infection is not inhibited or prevented, the agent is not a potential therapeutic agent. Methods of determining if the infection is inhibited or prevented are known in the art and several non-limiting examples are described herein; methods of determining if a biofilm is disrupted or prevented are known in the art and further disclosed herein. Non-limiting examples of potential therapeutic agents are from the group of: an antibody, an antibody derivative or fragment thereof, a polypeptide or a small molecule. Multiple antibodies can be administered concurrently or sequentially along with supporting therapies as noted herein.

In some embodiments, the antibody is not a polyclonal antibody.

In a further aspect, the agent binds the protein and the binding is compared to the binding of anti-DNABII antisera to the polypeptide describe herein, e.g., antisera directed against a polypeptide as described herein.

It should be appreciated that any of the general properties contemplated with respect of the agent for inhibiting, titrating, or competing the binding of a DNABII protein to a microbial DNA should likewise apply to the above disclosed methods relating to bacterial infection.

Dosing can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Kits

Kits containing the agents and instructions necessary to perform the in vitro and in vivo methods as described herein also are claimed. Accordingly, the disclosure provides kits for performing these methods which may include an agen disclosed herein as well as instructions for carrying out the methods disclosed herein such as collecting tissue and/or performing the screen, and/or analyzing the results, and/or administration of an effective amount of an agent as defined herein. These can be used alone or in combination with other suitable antimicrobial agents.

For example, a kit can comprise, or alternatively consist essentially of, or yet further consist of any one or more agent identified above, e.g., an agent of the group of an isolated or recombinant polypeptide or a fragment or an equivalent of each thereof; an isolated or recombinant polynucleotide encoding any one of the above noted polypeptides; an antibody or fragment thereof; or a small molecule that competes with the binding of a DNABII protein or polypeptide to a microbial DNA, and instructions for use. The kit can further comprising one or more of an adjuvant, an antigenic peptide or an antimicrobial. Examples of carriers include a liquid carrier, a pharmaceutically acceptable carrier, a solid phase carrier, a pharmaceutically acceptable carrier, a pharmaceutically acceptable polymer, a liposome, a micelle, an implant, a stent, a paste, a gel, a dental implant, or a medical implant.

The following examples are intended to illustrate, and not limit the embodiments disclosed herein.

EXAMPLES

Example 1: Generation of Rabbit and Chinchilla Polyclonal Anti-IhfA3$_{NTHI}$ Anti-IhfA5$_{NTHI}$ Anti-IhfB2$_{NTHI}$, Anti-mIhfB4$_{NTHI}$, and Anti-IhfA5-mIhfB4$_{NTHI}$ Antibodies, and Generation of Rabbit Polyclonal Fab Fragments An IHF$_{NTHI}$ tip-directed chimeric peptide was used to generate polyclonal serum in chinchillas and rabbits, as shown in FIG. 1. The "IhfA5-mIhfB4$_{NTHI}$ chimer" used to generate antibodies has *Haemophilus influenzae* IhfA5 sequence followed by a linker sequence (GPSL) followed by *Haemophilus influenzae* mIhfB4$_{NTHI}$ sequence (SEQ ID NO: 50: RPGRNPKTGDVVPVSARRVVGPSLF-SLHHRQPRLGRNPKTGDSV). The corresponding structural regions targeted within IHF are shown below the peptide sequence, as indicated by arrows (FIG. 1).

Polyclonal serum directed against *Haemophilus influenzae* IhfA3$_{NTHI}$, IhfA5$_{NTHI}$, IhfB2$_{NTHI}$, mIhfB4$_{NTHI}$, and IhfA5-mIhfB4$_{NTHI}$ chimer were prepared in chinchillas and also in rabbits according to standard techniques using, individually, each of IhfA3$_{NTHI}$, IhfA5$_{NTHI}$, IhfB2$_{NTHI}$, mIhfB4$_{NTHI}$, and IhfA5-mIhfB4$_{NTHI}$ chimer. The peptides used are as follows.

For IhfA3$_{NTHI}$, the corresponding sequence is SEQ ID NO: 12 (SEQ ID NO. 12: *Haemophilus influenzae* IhfA, A-3 fragment: FLEEIRLSLESGQDVKLSGF).

For IhfA5$_{NTHI}$, the corresponding sequence used was SEQ ID NO: 13 (SEQ ID NO. 13: *Haemophilus influenzae* hfA, A5 fragment: RPGRNPKTGDVVPVSARRV V).

For IhfB2$_{NTHI}$, the corresponding sequence used was SEQ ID NO: 15 (SEQ ID NO. 15: *Haemophilus influenzae* IhfB, B2 fragment: TLSAKEIENNIVKDILEFIS Q).

For mIhfB4$_{NTHI}$, the corresponding sequence used was SEQ ID NO: 17 (SEQ ID NO. 17: *Haemophilus influenzae* IhfB, B4 fragment: RGFGSFSLHHRQPRLGRNP K).

For IhfA5-mIhfB4$_{NTHI}$, the corresponding sequence used was SEQ ID NO: 50 (SEQ ID NO: 50: IhfA5-mIhfB4$_{NTHI}$ chimer recombinant polypeptide sequence: RPGRNPKTGDVVPVSARRVVGPSLFSLHHRQPRLGRNPKT GDSV).

In particular, rabbit polyclonal anti-IhfA3$_{NTHI}$, anti-IhfA5$_{NTHI}$, anti-IhfB2$_{NTHI}$, anti-mIhfB4$_{NTHI}$, and anti-IhfA5-mIhfB4$_{NTHI}$ were prepared as follows. Rabbits were injected with 250 µg of IhfA3$_{NTHI}$ peptide, IhfA5$_{NTHI}$ peptide, IhfB2$_{NTHI}$ peptide, mIhfB4$_{NTHI}$ peptide, or IhfA5-mIhfB4$_{NTHI}$ peptide, with Freund's complete adjuvant. Two booster immunizations of 250 µg of IhfA3$_{NTHI}$, IhfA5$_{NTHI}$, IhfB2$_{NTHI}$, mIhfB4$_{NTHI}$, or IhfA5-mIhfB4$_{NTHI}$ with Freund's incomplete adjuvant were given at 21-day intervals. As determined by ELISA of IhfA3$_{NTHI}$, IhfA5$_{NTHI}$, IhfB2$_{NTHI}$, mIhfB4$_{NTHI}$, or IhfA5-mIhfB4$_{NTHI}$, sera collected 21 days after the third injection had a reciprocal titer of >40,000 of IhfA3$_{NTHI}$, IhfA5$_{NTHI}$, IhfB2$_{NTHI}$, mIhfB4$_{NTHI}$, or IhfA5-mIhfB4$_{NTHI}$-reactive material. The antibody was not purified further. Crude sera was stored at −70° C.

Figure 3:
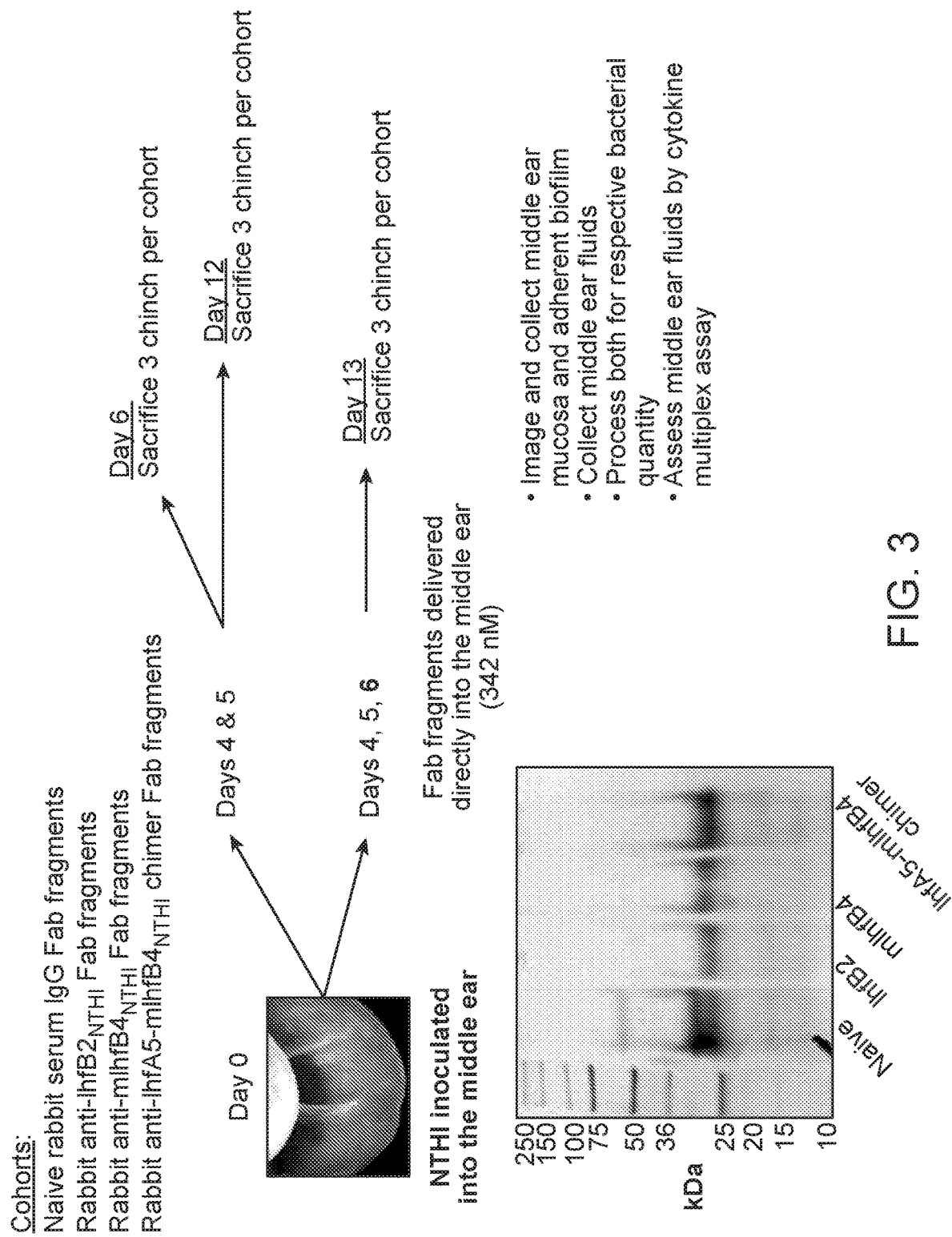
FIG. 3 depicts the method by which the disruption of biofilms formed by Haemophilus influenzae (NTHI) 86-028NP was analyzed in the middle ear of adult chinchillas using Fab fragments generated from polyclonal rabbit anti-IhfB2$_{NTHI}$, anti-mIhfB4$_{NTHI}$, anti-IhfA5-mIhfB4$_{NTHI}$ chimer and naive rabbit serum. Experiments included cohorts using naive rabbit serum IgG Fab fragments, rabbit anti-IhfB2$_{NTHI}$ Fab fragments, rabbit anti-mIhfB4$_{NTHI}$ Fab fragments, and rabbit anti-IhfA5-mIhfB4$_{NTHI}$ chimer Fab fragments. On day zero (0), Haemophilus influenzae (NTHI) 86-028NP was inoculated into the middle ear of chinchillas. Then, either on days 4 and 5 (two dose experiments) or on days 4, 5, and 6 (three dose experiments), Fab fragments were administered by direct delivery into the middle ear (342 nM). For those administered on day 4 and 5, three (3) chinchillas per cohort were sacrificed either on day 6 or day 12. For those administered on day 4, 5, and 6, three (3) chinchillas per cohort were sacrificed on day 13. Following sacrifice, chinchillas were imaged, middle ear mucosa was collected, adherent biofilm was assessed, middle ear fluids were collected, quantitation of bacteria was performed, and middle ear fluids were assessed using a cytokine multiplex assay. The purity of each Fab preparation is also shown (4 separate preparations: naïve, IhfB2, mIhfB4, and IhfA5-mIhfB4 chimer), as confirmed by 10% Bis-Tris PAGE (BioRad) and SYPRO Orange Protein Gel stain (Invitrogen).

Chinchilla polyclonal anti-IhfA3$_{NTHI}$, anti-IhfA5$_{NTHI}$, anti-IhfB2$_{NTHI}$, anti-mIhfB4$_{NTHI}$, and anti-IhfA5-mIhfB4$_{NTHI}$ were prepared as follows. Chinchillas were injected with 50 µg IhfA3$_{NTHI}$ peptide, IhfA5$_{NTHI}$ peptide, IhfB2$_{NTHI}$ peptide, mIhfB4$_{NTHI}$ peptide, or IhfA5-mIhfB4$_{NTHI}$ peptide admixed with the adjuvant monophosphoryl lipid A. Two booster doses of the same formulation were administered at 30 day intervals. Ten days after the final dose, blood was collected from each animal and crude sera stored at −70° C. Use of the anti-IhfB2$_{NTHI}$ antibodies are shown in FIG. 3.

Figures 2A, 2B:
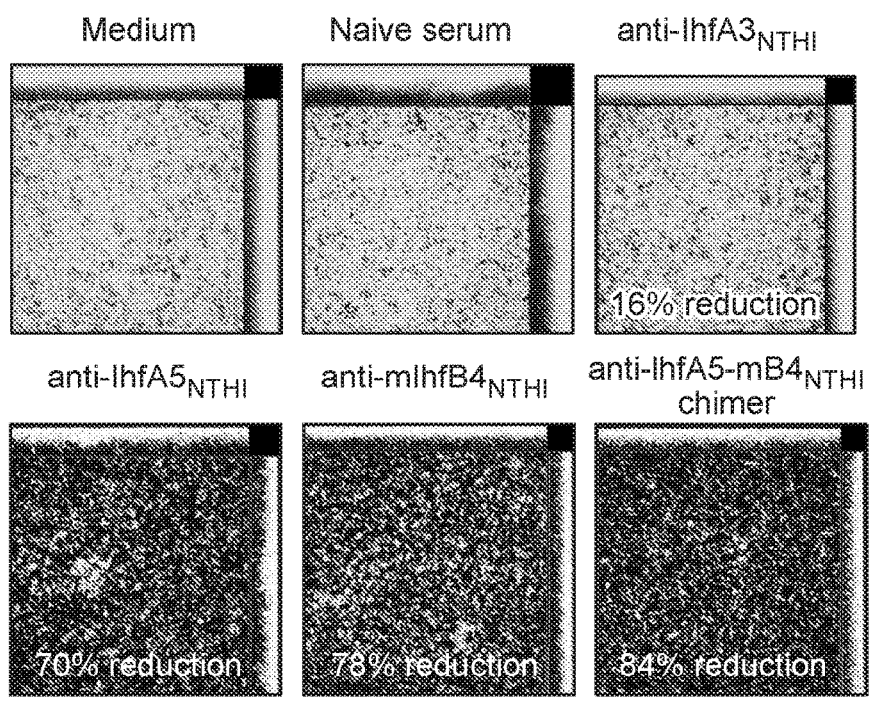
FIGS. 2A and 2B show the effectiveness of the chimer recombinant polypeptides.

The immunogenicity and function of anti-IhfA5-mIhfB4$_{NTHI}$ was determined. FIG. 2(A) shows the reciprocal titers for chinchilla serum and rabbit serum generated using the IhfA5-mIhfB4$_{NTHI}$ chimer peptide. Chinchilla serum and rabbit serum were analyzed to assess the following: anti-IhfA3$_{NTHI}$, anti-IhfA5$_{NTHI}$, anti-mIhfB4$_{NTHI}$, and anti-IhfA5-mIhfB4$_{NTHI}$ chimer.

Rabbit Fab fragments were generated from IgG-enriched polyclonal rabbit anti-IhfB2$_{NTHI}$, anti-mIhfB4$_{NTHI}$, anti-IhfA5-mIhfB4$_{NTHI}$ chimer and naïve rabbit serum IgG by 4 hr digestion with agarose-immobilized papain protease+cysteine-HCl (ThermoScientific). Fragments were then purified via Protein A spin column, dialyzed versus 10 mM phosphate buffered saline, pH 7.4 and purity of each preparation was confirmed by 10% Bis-Tris PAGE (BioRad) and SYPRO Orange Protein Gel stain (Invitrogen). The concentration of each Fab fragment preparation was determined via Nanodrop using an extinction coefficient of 1.4.

Example 2: Reduction of NTHI Biofilm Analysis Using Chinchilla Serum

NTHI 86-028NP colonies were collected from overnight culture on chocolate agar and suspended in brain heart infusion broth supplemented with 2 µg β-NAD and heme per ml medium (sBHI). The optical density at 490 nm was then adjusted to 0.65 and the culture diluted 1:6 in sBHI prior to incubation at 37° C. with 5% $CO_2$ for 3 hr, static. Next, the culture was diluted 1:2500 in fresh sBHI and 200 µl of the suspension aliquoted into each well of an 8-well chamber slide. The slide was then incubated at 37° C. with 5% $CO_2$ for 3 hr, static. After 16 hr, 200 µl fresh sBHI was added to each well, and the slide incubated an additional 8 hr. At this time point, medium was aspirated from each well and treatments (1. Chinchilla serum at 1:50 dilution or 2. polyclonal antibody or Fab fragments at 171 nM) added. The biofilms were incubated an additional 16 hr. Biofilms were then washed and stained with FM1-43FX bacterial cell membrane stain (Invitrogen) and fixed overnight at 4° C. in 16% paraformaldehyde, 2.5% glutaraldehyde, 4.0% acetic acid in 0.1 M phosphate buffer (pH 7.4). Fixative was aspirated an 200 µl 0.9% saline was added to each well prior to viewing of biofilms on a Zeiss 510 Meta-laser scanning confocal microscope. Images were compiled with Zeiss Zen software and biofilm biomass calculated with COMSTAT2 software.

The ability of chinchilla serum (naïve serum, anti-IhfA3$_{NTHI}$, anti-IhfA5$_{NTHI}$, anti-mIhfB4$_{NTHI}$, and anti-IhfA5-mB4$_{NTHI}$ chimer) to disrupt biofilm was assessed. FIG. 2(B) shows the disruption of biofilms formed by *Haemophilus influenzae* (NTHI) 86-028NP upon incubation with medium control or various chinchilla serum as follows: naïve serum control, anti-IhfA3$_{NTHI}$, anti-IhfA5$_{NTHI}$, anti-mIhfB4$_{NTHI}$, and anti-IhfA5-mB4$_{NTHI}$ chimer. In these experiments, a 1:50 dilution of chinchilla serum was used. The following results were observed: a 16% reduction in biofilm was observed for anti-IhfA3$_{NTHI}$ serum; a 70% reduction in biofilm was observed for anti-IhfA5$_{NTHI}$ serum; a 78% reduction in biofilm was observed for anti-mIhfB4$_{NTHI}$ serum; and an 84% reduction in biofilm was observed for anti-IhfA5-mIhfB4$_{NTHI}$ chimer serum (FIG. 2(B)). The reduction in biomass is relative to naïve serum.

Example 3: Otitis Media Experiments Using Rabbit Fabs

Middle ear infection (or otitis media, OM) is a highly prevalent disease worldwide, with the most severe form (called chronic suppurative OM or CSOM) afflicting 50-330 million children globally each year. The socioeconomic burden of OM is also great, with cost estimates between $5-6 billion in the United States alone annually. All three of the predominant bacterial pathogens of OM are known to form biofilms both in vitro and in vivo and recently, clinicians have come to appreciate that the chronicity and recurrence of OM is due, at least in part, to the formation of bacterial biofilms within the middle ear cavity.

In fact, results of labeling of otorrhea solids from pediatric patients with tympanostomy tubes and persistent otorrhea for eDNA and IHF in combination with microbiological culture indicate that biofilms play a role in chronic otorrhea. Specifically, of 15 pediatric otorrhea samples analyzed, 9 (60%) contained solids positive for labeling IHF in association with a lattice of eDNA (labeled using rabbit anti-IHF, detected with goat anti-rabbit IgG conjugated to AlexaFlour 594) and 75% yielded positive bacterial cultures. Bacterial culture results demonstrated the presence of *H. influenzae*, MRSA, *S. pneumonia, M catarrhalis*, and *P. aeruginosa*. These data suggest that DNABII proteins may serve as a therapeutic target in post-tympaostomy tube otorrhea among other otic disease.

In one chinchilla model of OM, juvenile chinchillas are first given a viral "cold" followed a week later by their being challenged intranasally with an inoculum viable bacteria. Similar to the human condition wherein "my child has a cold and a week later gets an ear infection" chinchillas will also develop a bacterial OM approximately one week after a challenge, and while experiencing the viral upper respiratory tract infection. Once bacteria gain access to the middle ear (either via ascension of the Eustachian tube or following direct challenge to the middle ear space), they will form a robust biofilm. Applicants thus contemplate and indeed have already used chinchilla models as reported herein to demonstrate the protective efficacy of IHF immunization which results in rapid resolution of existing biofilms. This model is also useful for therapeutic approaches via either passive delivery of anti-DNABII antibody or via delivery of a small molecule or other agent known to bind to IHF or other DNABII family members.

Because the chinchilla model is used for development and pre-clinical testing of human vaccines, it is important to establish meaningful immunological parallels with the human host, particularly the child. Applicants have shown that effusions recovered from children with AOM due to NTHI, and middle ear fluids from chinchillas with experimental NTHI-induced OM, recognized immunodominant regions of OMP P5 in a similar hierarchical manner (see for e.g., Novotny et al. (2000) Infect 68(4):2119-2128; Novotny et al. (2007) 9$^{th}$ International Symposium on Recent Advances in Otitis Media; St. Pete Beach, Fla.; Novotny et al. (2002) Vaccine 20(29-30):3590-3597). Applicants have also shown that chinchillas with experimental OM, children with natural OM, and adults with exacerbations of COPD, all recognized peptides representing PilA in a highly analogous manner (see, e.g., Adams et al. (2007) 107th General Meeting, American Society for Microbiology, 2007, Toronto, ON; Adams et al. (2007) 9th International Symposium on Recent Advances in Otitis Media, St. Pete Beach, Fla.). Thus, chinchillas with experimental OM and children with natural disease respond similarly immunologically to at least two unrelated NTHI protein adhesins. This parallel was put to the ultimate test recently, when the chinchilla AV-NTHI superinfection model was used to conduct pre-clinical efficacy testing of a novel 11-valent Protein D-pneumococcal polysaccharide conjugate vaccine. Data obtained in the chinchilla predicted an efficacy of 34% whereas, when tested in children, the efficacy obtained against *H. influenzae*-induced OM was 35.6% (see, e.g., Novotny et al. (2006) Vaccine 24(22):4804-11 and Prymula et al. (2006) Lancet.

367(9512):740-8), thus lending strong support to the relevancy of this model for the development and testing of OM vaccine candidates.

Methods:

Example 1 describes the generation of Fab (fragment antigen binding) fragments from rabbit polyclonal antibodies directed against the *Haemophilus influenzae* IhfB2$_{NTHI}$, mIhfB4$_{NTHI}$, and IhfA5-mIhfB4$_{NTHI}$ chimer, as well as from naive rabbit serum IgG. FIG. 3 shows the purity of each Fab preparation (4 separate preparations: naïve, IhfB2, mIhfB4, and IhfA5-mIhfB4 chimer), as confirmed by 10% Bis-Tris PAGE (BioRad) and SYPRO Orange Protein Gel stain (Invitrogen).

FIG. 3 depicts the method by which the disruption of biofilms formed by *Haemophilus influenzae* (NTHI) 86-028NP was analyzed in the middle ear of adult chinchillas using Fab fragments generated from polyclonal rabbit anti-IhfB2$_{NTHI}$, anti-mIhfB4$_{NTHI}$, anti-IhfA5-mIhfB4$_{NTHI}$ chimer, and naive rabbit serum. Experiments included cohorts using native rabbit serum IgG Fab fragments, rabbit anti-IhfB2$_{NTHI}$ Fab fragments, rabbit anti-mIhfB4$_{NTHI}$ Fab fragments, and rabbit anti-IhfA5-mIhfB4$_{NTHI}$ chimer Fab fragments.

In order to determine the efficacy of the generated Fab (fragment antigen binding) fragments from rabbit polyclonal antibodies, NTHI bacteria were injected into the middle ear space of the chinchillas and allowed to form a biofilm. In particular, adult chinchillas (*Chinchilla lanigera*) with no evidence of middle ear disease were procured (Rauscher's Chinchilla Ranch, LLC) and rested for 7 days prior to transbullar challenge with 1000 colony-forming units (CFU) of nontypeable *Haemophilus influenzae* #86-028NP per bulla diluted in sterile, pyrogen-free saline (Day zero (0)) (FIG. 3). Then, either on days 4 and 5 or on days 4, 5, and 6, a 342 nM Fab fragment solution was infused into each middle ear space (100 µl per bulla; 342 nM) (FIG. 3). For chinchillas administered the Fab solution on days 4 and 5, 3 chinchillas per cohort were sacrificed either on day 6 or day 12 (two dose experiments) (FIG. 3). For those administered on day 4, 5, and 6, 3 chinchillas per cohort were sacrificed on day 13 (three dose experiments). Following sacrifice, chinchillas were imaged, middle ear mucosa was collected, adherent biofilm was assessed, middle ear fluids were collected, quantitation of bacteria was performed, and middle ear fluids were assessed using a cytokine multiplex assay.

Middle ear fluids were collected and an aliquot serially diluted and plated on to chocolate agar to quantitate the relative planktonic bacterial load. Remaining fluids were centrifuged at 1000×g for 5 min, supernatants separated and both cellular pellet and fluid fractions snap-frozen prior to storage at −80° C. The middle ear mucosa and adherent bacterial biomass were digitally imaged, collected into pre-weighed microcentrifuge tubes and homogenized in 1.0 ml sterile 0.9% sodium chloride. Homogenates were also serially diluted and plated, as before, to quantitate the population of bacteria adherent within the middle ear space per mg tissue/biomass. Remaining sample was snap-frozen prior to storage at −80° C. Culture plates were incubated for 24 h at 37° C. in a humidified atmosphere prior to enumeration of bacterial colonies via Protocol2 instrument (Synbiosis).

Video otoscopy and tympanometry. Video otoscopy using a 0-degree, 3-inch probe connected to a digital camera system (MedRx, Largo, Fla.) was utilized to monitor signs of OM (e.g. tympanic membrane inflammation and/or presence of fluid in the middle ear space). Tympanometry was performed with a MADSEN Otoflex tympanometer and data analyzed with OTOsuite software (Otometrics, Schaumburg, Ill.). Overall signs of OM were blindly rated on an established 0 to 4+ scale and middle ears with a score of ≥2.0 were considered positive for OM if middle ear fluid was visible behind the tympanic membrane. If the tympanic membrane could not be visualized due to an obstruction within the ear canal (i.e. due to cerumen accumulation), that ear was excluded from the day's count. Per established protocol, each middle ear was considered independent, and for each cohort, the percentage of middle ears with OM was calculated.

To rank the residual biofilm within the middle ear space, middle ear images were scrambled and reviewed blindly by 7 individuals. Using an established rubric, a score of 0 to 4 was assigned to each image, whereby 0: no biofilm visible, 1: biofilm fills≤25% of middle ear space, 2: biofilm fills>25% to ≤50% of middle ear space, 3: biofilm fills>50% to ≤75% middle ear space, 4: biofilm fills>75% to ≤100% middle ear space.

This ranking/scoring scale is described in detail in Table 2 below, indicating the relative amount of biomass remaining within the middle ear of each animal.

TABLE 2

| Score | Criteria |
| --- | --- |
| 0 | No evidence of biomass. |
| 1+ | Biomass fills ≤25% of middle ear space. Junction of the bony septa to inferior bulla is visible. |
| 2+ | Biomass fills >25% to ≤50% of middle ear space. Unable to visualize where the bony septa meet the inferior bulla. |
| 3+ | Biomass fills >50% to ≤75% of middle ear space. Biomass covers >50% of the length of bony septa. |
| 4+ | Biomass fills >75% to ≤100% of middle ear space. Bony septa not visible; obscured by biomass. |

The relative quantity of a panel of pro- and anti-inflammatory cytokines in clarified middle ear fluids (IL-1β, IL-6, IL-8, IL-12p70, IL-17A, TNF, IFNγ, IL-4, IL-10, and IL-13) was determined using BD Cytometric Bead array (BD Biosciences) according to manufacturer's instructions and samples assessed on a BD Accuri C6 cytometer. Data were analyzed with FloJo V_10 software.

Figure 4:
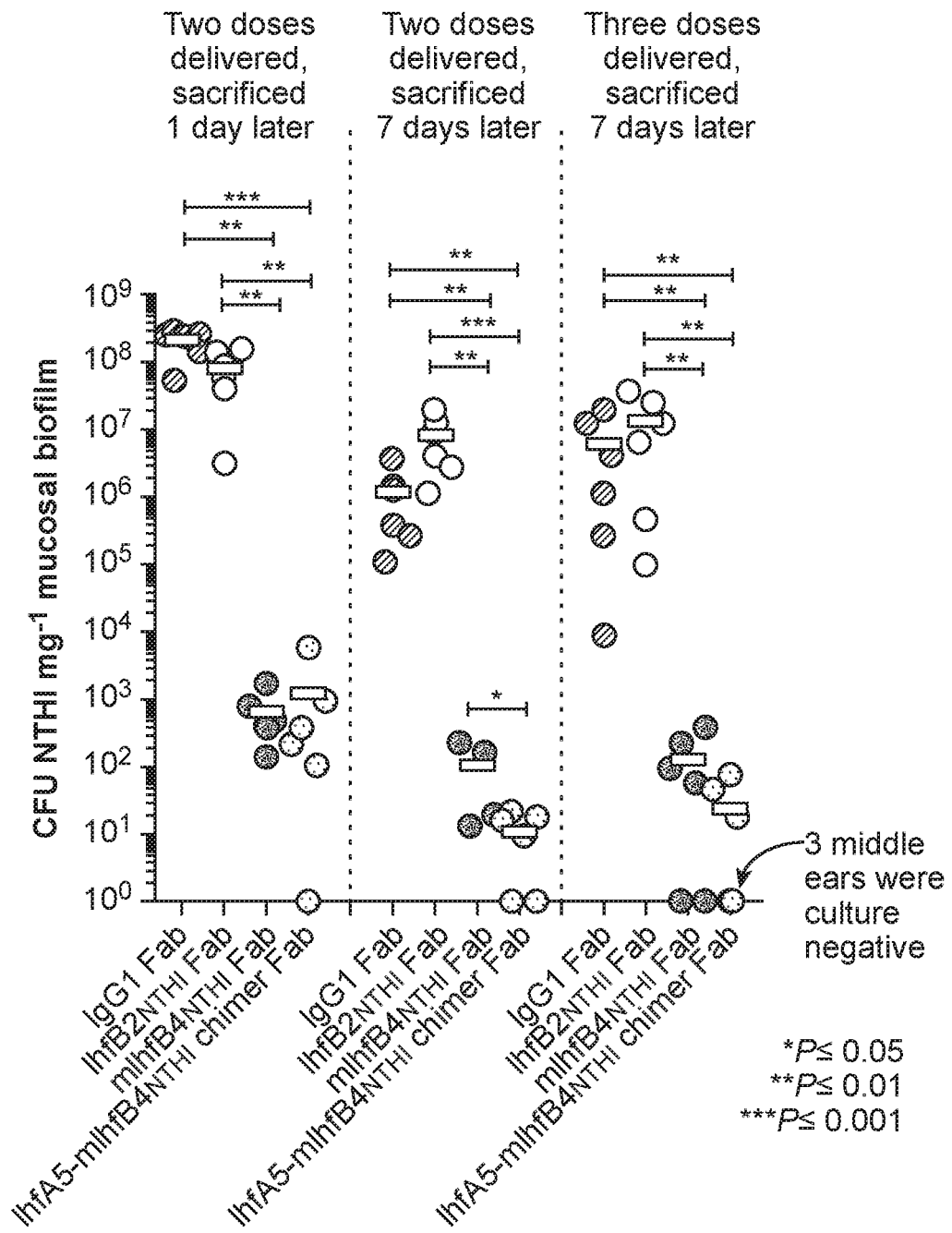
FIG. 4 shows quantitations of colony forming units (CFU) Haemophilus influenzae (NTHI) 86-028NP per milligram (mg) of mucosal biofilm in chinchillas administered either rabbit IgG1 Fab (circles w/diagonal lines), rabbit IhfB2$_{NTHI}$ Fab (circles without shading), rabbit mIhfB4$_{NTHI}$ Fab (solid shaded circles), or rabbit IhfA5-mIhfB4$_{NTHI}$ chimer Fab (dotted circles) after Haemophilus influenzae (NTHI) 86-028NP challenge and biofilm formation. Quantitations were performed in three different experiments, as follows: (1) two doses of the respective Fabs were administered, followed by sacrifice 1 day later; (2) two doses of the respective Fabs were administered, followed by sacrifice 7 days later; and (3) three doses of the respective Fabs were administered, followed by sacrifice 7 days later. Doses of Fabs were administered on days 4 and 5 (two doses) or on days 4, 5, and 6 (three doses) after Haemophilus influenzae (NTHI) 86-028NP challenge. P values are shown: *P≤0.05,  P≤0.01, and * P≤0.001.

Results:

The ability of mIhfB4$_{NTHI}$ Fab and IhfA5-mIhfB4$_{NTHI}$ chimer Fab to reduce mucosal biofilm was determined. FIG. 4 shows quantitations of colony forming units (CFU) *Haemophilus influenzae* (NTHI) 86-028NP per milligram (mg) of mucosal biofilm in chinchillas administered either rabbit IgG1 Fab, rabbit IhfB2$_{NTHI}$ Fab, rabbit mIhfB4$_{NTHI}$ Fab, or rabbit IhfA5-mIhfB4$_{NTHI}$ chimer Fab after *Haemophilus influenzae* (NTHI) 86-028NP challenge and biofilm formation. Quantitations were performed for the following dose/sacrifice combinations: (1) two doses of the respective Fabs were administered, followed by sacrifice 1 day later; (2) two doses of the respective Fabs were administered, followed by sacrifice 7 days later; and (3) three doses of the respective Fabs were administered, followed by sacrifice 7 days later. Doses of Fabs were administered on days 4 and 5 (two doses) or on days 4, 5, and 6 (three doses) after *Haemophilus influenzae* (NTHI) 86-028NP challenge. In all three dose/sacrifice combinations, significantly fewer *Haemophilus influenzae* (NTHI) 86-028NP were adherent to the middle ear mucosa and present within biofilms after administration of mIhfB4$_{NTHI}$ Fab or IhfA5-mIhfB4$_{NTHI}$ chimer Fab compared to nonspecific IgG1 Fab and IhfB2$_{NTHI}$ Fab controls (FIG. 4). Administration of two doses of mIhfB4 or IhfA5-mIhfB4 chimer Fab fragments was comparable to three doses in eradicating established middle ear biofilms (FIG.

4). At 7 days following administration of two treatment doses, animals that had received Fab fragments to the chimeric immunogen had significantly fewer bacteria within this biological sample from the middle ear (*P≤0.05,  P≤0.01, and * P≤0.001), as shown in FIG. 4.

Figure 5:
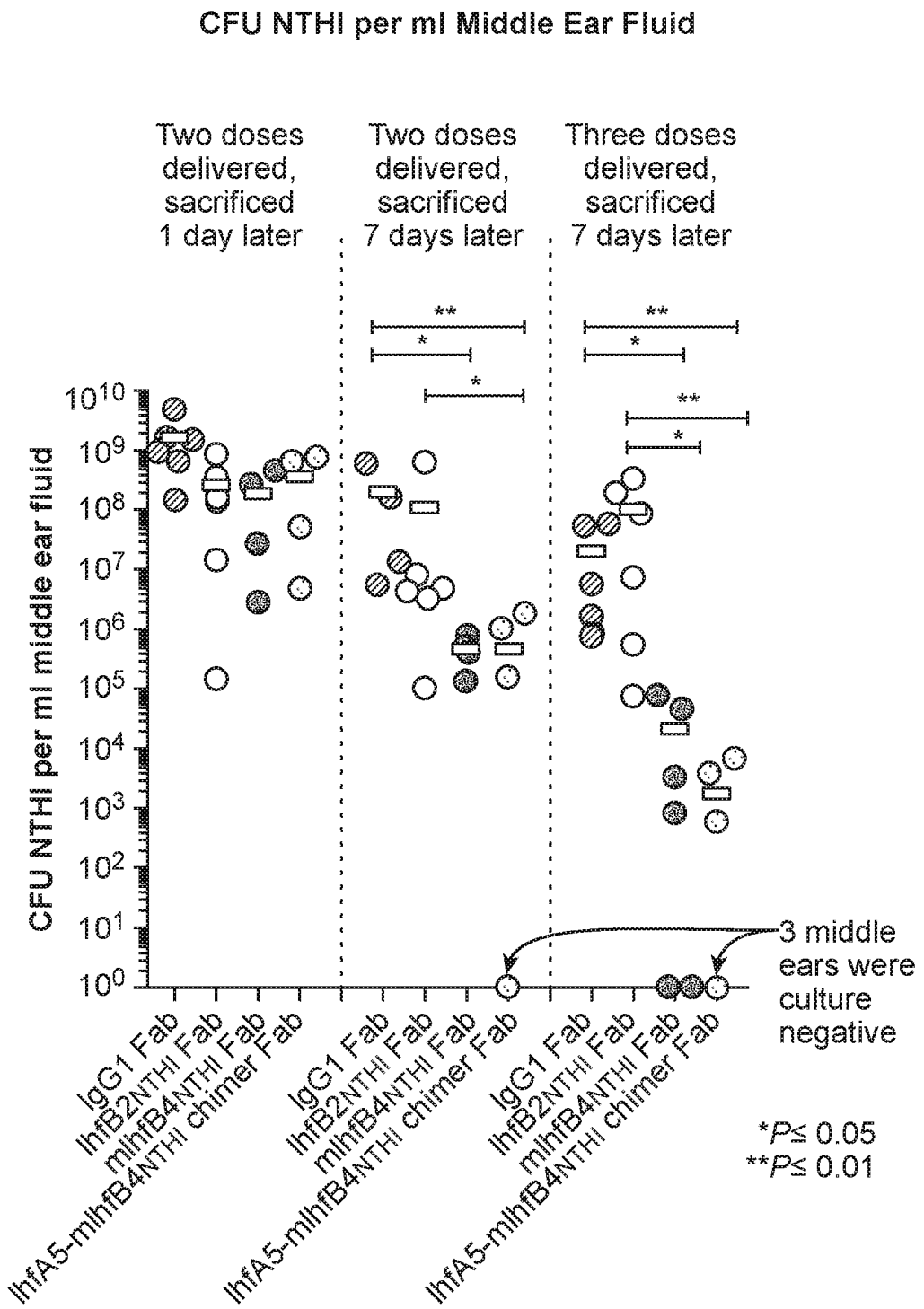
FIG. 5 shows quantitations of colony forming units (CFU) Haemophilus influenzae (NTHI) 86-028NP per milliliter (ml) of middle ear fluid in chinchillas administered either rabbit IgG1 Fab (circles w/diagonal lines), IhfB2$_{NTHI}$ Fab (circles without shading), mIhfB4$_{NTHI}$ Fab (solid shaded circles), or IhfA5-mIhfB4$_{NTHI}$ chimer Fab (dotted circles) after *Haemophilus influenzae* (NTHI) 86-028NP challenge and biofilm formation. Quantitations were performed in three different experiments, as follows: (1) two doses of the respective Fabs were administered, followed by sacrifice 1 day later; (2) two doses of the respective Fabs were administered, followed by sacrifice 7 days later; and (3) three doses of the respective Fabs were administered, followed by sacrifice 7 days later. Doses of Fabs were administered on days 4 and 5 (two doses) or on days 4, 5, and 6 (three doses) after *Haemophilus influenzae* (NTHI) 86-028NP challenge. P values are shown: *P≤0.05 and ** P≤0.01.

FIG. 5 shows quantitations of colony forming units (CFU) *Haemophilus influenzae* (NTHI) 86-028NP per milliliter (ml) of middle ear fluid in chinchillas administered either IgG1 Fab, IhfB2$_{NTHI}$ Fab, mIhfB4$_{NTHI}$ Fab, or IhfA5-mIhfB4$_{NTHI}$ chimer Fab after *Haemophilus influenzae* (NTHI) 86-028NP challenge and biofilm formation. Quantitations were performed for the following dose/sacrifice combinations: (1) two doses of the respective Fabs were administered, followed by sacrifice 1 day later; (2) two doses of the respective Fabs were administered, followed by sacrifice 7 days later; and (3) three doses of the respective Fabs were administered, followed by sacrifice 7 days later. Doses of Fabs were administered on days 4 and 5 (two doses) or on days 4, 5, and 6 (three doses) after *Haemophilus influenzae* (NTHI) 86-028NP challenge. Because antibodies directed against DNABII protein tips can induce biofilm collapse and release of resident bacteria, a difference in relative concentration of recoverable NTHI in middle ear fluids one day after administration of the final dose was not expected and was not observed. However, one week after receipt of two or three doses of mIhfB4 or IhfA5-mIhfB4 chimer Fab fragments, a significant reduction in NTHI within middle ear fluids was observed (FIG. 5) (*P≤0.05 and ** P≤0.01). Administration of Fab fragments directed against either mIhfB4 or the IhfA5-mIhfB4 chimer continued to mediate a therapeutic effect for at least one week following administration of the last dose of Fab and data suggest this dosing regime is flexible and optimizable.

Figure 6:
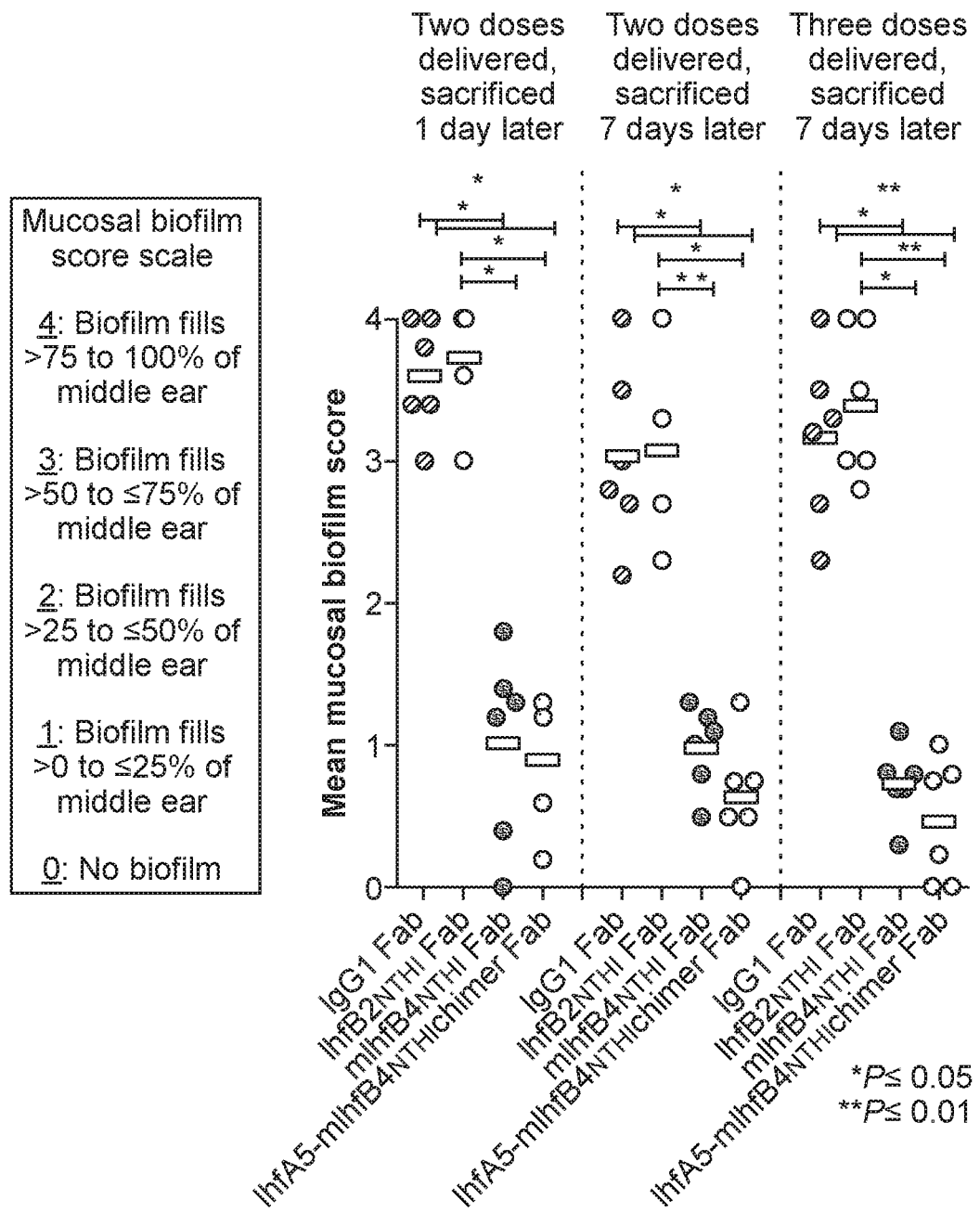
FIG. 6 shows mean mucosal biofilm scores (7 blinded reviewers) for chinchillas administered either rabbit IgG1 Fab (circles w/diagonal lines), IhfB2$_{NTHI}$ Fab (circles without shading), mIhfB4$_{NTHI}$ Fab (solid shaded circles), or IhfA5-mIhfB4$_{NTHI}$ chimer Fab (dotted circles) after *Haemophilus influenzae* (NTHI) 86-028NP challenge and biofilm formation. Quantitations were performed in three different experiments, as follows: (1) two doses of the respective Fabs were administered, followed by sacrifice 1 day later; (2) two doses of the respective Fabs were administered, followed by sacrifice 7 days later; and (3) three doses of the respective Fabs were administered, followed by sacrifice 7 days later. Doses of Fabs were administered on days 4 and 5 (two doses) or on days 4, 5, and 6 (three doses) after *Haemophilus influenzae* (NTHI) 86-028NP challenge. A mucosal biofilm score scale was used to rank the residual biofilm within the middle ear space. Using an established rubric, a score of 0 to 4 was assigned to each image, as follows: zero (0): no biofilm visible; 1: biofilm fills>0 to ≤25% of middle ear space; 2: biofilm fills>25% to ≤50% of middle ear space; 3: biofilm fills>50% to ≤75% middle ear space; and 4: biofilm fills>75% to 100% middle ear space. P values are shown: *P≤0.05 and **P≤0.01.

Mean mucosal biofilm scores were determined to assess the ability of rabbit mIhfB4$_{NTHI}$ Fab and rabbit IhfA5-mIhfB4$_{NTHI}$ chimer Fab to disrupt biofilm. FIG. 6 shows mean mucosal biofilm scores for chinchillas administered either IgG1 Fab, IhfB2$_{NTHI}$ Fab, mIhfB4$_{NTHI}$ Fab, or IhfA5-mIhfB4$_{NTHI}$ chimer Fab after *Haemophilus influenzae* (NTHI) 86-028NP challenge and biofilm formation. Quantitations were performed for the following dose/sacrifice combinations: (1) two doses of the respective Fabs were administered, followed by sacrifice 1 day later; (2) two doses of the respective Fabs were administered, followed by sacrifice 7 days later; and (3) three doses of the respective Fabs were administered, followed by sacrifice 7 days later. Doses of Fabs were administered on days 4 and 5 (two doses) or on days 4, 5, and 6 (three doses) after *Haemophilus influenzae* (NTHI) 86-028NP challenge. A mucosal biofilm score scale was used to rank the residual biofilm within the middle ear space. Using an established rubric, a score of 0 to 4 was assigned to each image, as follows: zero (0): no biofilm visible; 1: biofilm fills>0 to ≤25% of middle ear space; 2: biofilm fills>25% to ≤50% of middle ear space; 3: biofilm fills>50% to ≤75% middle ear space; and 4: biofilm fills>75% to 100% middle ear space (FIG. 6). As shown in FIG. 6, a significantly lower mean mucosal biomass score was observed in chinchillas treated with mIhfB4$_{NTHI}$ Fab and IhfA5-mIhfB4$_{NTHI}$ chimer Fab compared to chinchillas administered IgG1 Fab or IhfB2$_{NTHI}$ Fab controls (*P≤0.05 and **P≤0.01). Because antibody directed against DNABII protein tips induces biofilm collapse, a significant decrease in mucosal biofilm in the middle ear of animals administered mIhfB4 or IhfA5-mIhfB4 chimer Fab fragments one day after receipt of two doses was observed (FIG. 6). This decrease was maintained one week after receipt of two or three doses of mIhfB4 or IhfA5-mIhfB4 chimer Fab fragments. Administration of Fab fragments directed against either mIhfB4 or the IhfA5-mIhfB4 chimer continued to mediate a therapeutic effect for at least one week after receipt of the last dose and data suggest this dosing regime is flexible and optimizable.

Figure 7:
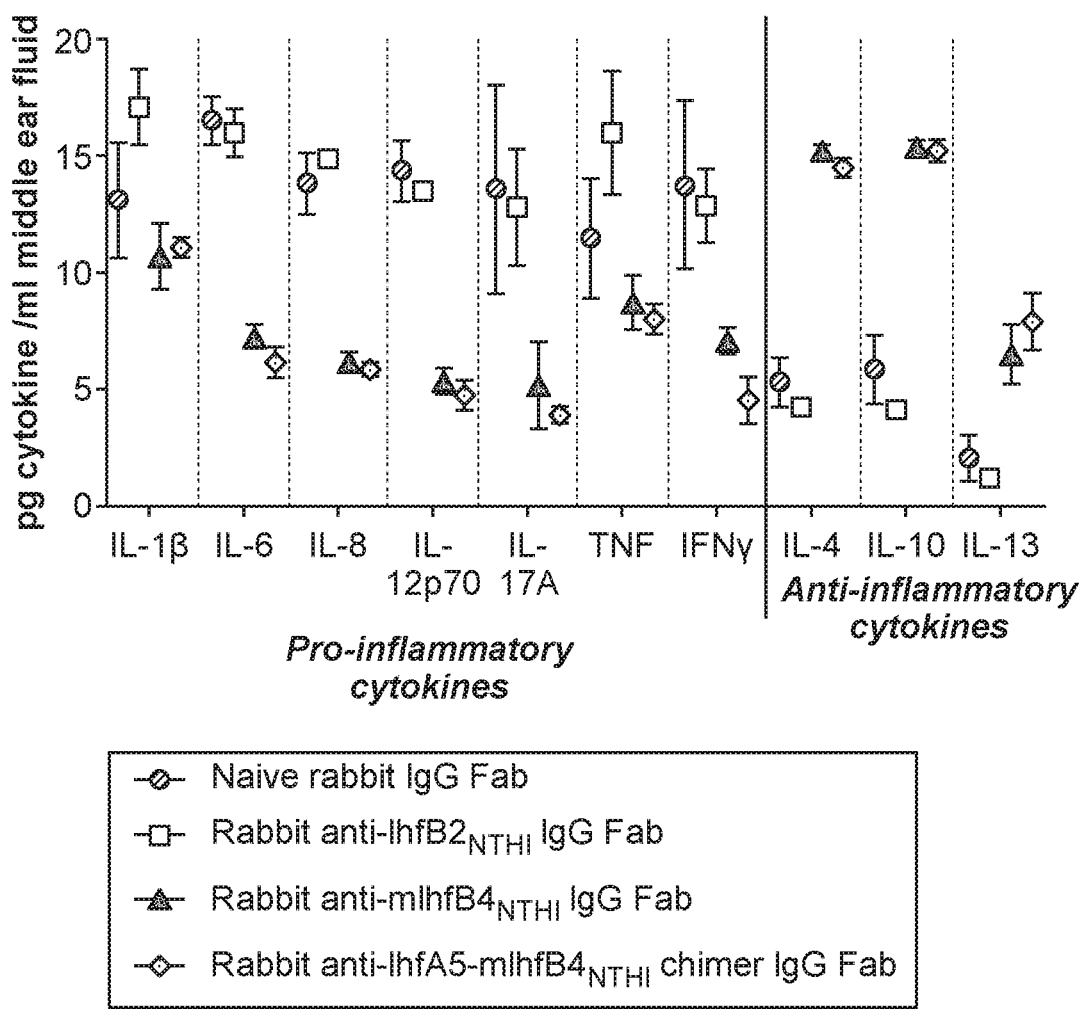
FIG. 7 shows the relative quantity of a panel of pro- and anti-inflammatory cytokines in clarified middle ear fluids in chinchillas administered either naïve rabbit IgG Fab, rabbit anti-mIhfB2$_{NTHI}$ IgG Fab, rabbit anti-mIhfB4$_{NTHI}$ IgG Fab, or rabbit anti-IhfA5-mIhfB4$_{NTHI}$ chimer IgG Fab after *Haemophilus influenzae* (NTHI) 86-028NP challenge and biofilm formation. The pro-inflammatory cytokines measured included: IL-10, IL-6, IL-8, IL-12p70, IL-17A, TNF, and IFNγ. The anti-inflammatory cytokines measured included: IL-4, IL-10, and IL-13.

Pro- and anti-inflammatory cytokines were measured in clarified middle ear fluids to assess the effects of mIhfB4$_{NTHI}$ Fab and IhfA5-mIhfB4 chimer Fab on inflammation. FIG. 7 shows the relative quantity of a panel of pro- and anti-inflammatory cytokines in clarified middle ear fluids in chinchillas administered either naïve rabbit IgG Fab, rabbit anti-IhfB2$_{NTHI}$ IgG Fab, rabbit anti-mIhfB4$_{NTHI}$ Fab, or rabbit anti-IhfA5-mIhfB4$_{NTHI}$ chimer IgG Fab after *Haemophilus influenzae* (NTHI) 86-028NP challenge and biofilm formation. Fluids were collected from chinchillas that were administered two doses of Fab fragments and sacrificed one day after the receipt of the second dose. The pro-inflammatory cytokines measured included: IL-10, IL-6, IL-8, IL-12p70, IL-17A, TNF, and IFNγ. The anti-inflammatory cytokines measured included: IL-4, IL-10, and IL-13. A greater relative quantity of pro-inflammatory cytokines were observed in middle ears treated with rabbit anti-IhfB2$_{NTHI}$ Fab or nonspecific rabbit IgG Fab compared to middle ears treated with either rabbit anti-mIhfB4$_{NTHI}$ IgG Fab or rabbit anti-IhfA5-mIhfB4$_{NTHI}$ chimer IgG Fab (shown in FIG. 7). The greatest quantity of anti-inflammatory cytokines (IL-4, IL-10, and IL-13) were observed in middle ears treated with rabbit anti-mIhfB4$_{NTHI}$ Fab or rabbit anti-IhfA5-mIhfB4$_{NTHI}$ chimer Fab (shown in FIG. 7).

A summary of the efficacies of rabbit IgG Fab polyclonal fragments versus intact rabbit polyclonal IgG is shown in Table 3 below.

TABLE 3

| Characteristics: Note that for all IgG and Fabs indicated below, the host was Rabbit and the clonality of IgG was polyclonal | | | | In vivo (Chinchilla model of NTHI induced otitis media) | | | |
| --- | --- | --- | --- | --- | --- | --- | --- |
| | | In vitro vs NTHI Biofilms | | | Log reduction in CFU | | |
| Target | IgG or Fab Fragment | Concentration applied to pre-formed biofilms | Reduction in Biomass[1] | Concentration infused into middle ear space | NTHI/mg middle ear mucosal biofilm[2] | Middle ear biofilm score[3] | in vivo study code[4] |
| IhfB2 | IgG | 171 nM | 0 | 342.5 nM | ND | ND | PoMo |
| IhfB2 | Fab | 171 nM | 0 | 342.5 nM | 0.4-log$_{10}$ | 3.7 | Rab pAb Fab |

TABLE 3-continued

Characteristics:
Note that for all IgG and Fabs indicated below, the host was Rabbit and the clonality of IgG was polyclonal

| Target | IgG or Fab Fragment | In vitro vs NTHI Biofilms | | In vivo (Chinchilla model of NTHI induced otitis media) | | | | |
|---|---|---|---|---|---|---|---|---|
| | | Concentration applied to pre-formed biofilms | Reduction in Biomass[1] | Concentration infused into middle ear space | Log reduction in CFU NTHI/mg middle ear mucosal biofilm[2] | Middle ear biofilm score[3] | in vivo study code[4] | |
| mIhfB4 | IgG | 171 nM | 75% | 342.5 nM | ND | ND | PoMo | |
| mIhfB4 | Fab | 171 nM | 78% | 342.5 nM | 5.5-$\log_{10}$ | 1.0 | Rab pAb Fab | |
| IhfA5-mIhfB4 chimer | IgG | 171 nM | 82% | 342.5 nM | ND | ND | ND | |
| IhfA5-mIhfB4 chimer | Fab | 171 nM | 87% | 342.5 nM | 5.2-$\log_{10}$ | 0.9 | Rab pAb Fab | |

[1]Relative to respective naive serum for polyclonal sera determined by COMSTAT2.
[2]One day after receipt of the final dose, relative to respective naive serum for polyclonal sera.
[3]Biomass score: 0 = no biomass; 1 = 0-25% middle ear space filled with bacterial biomass; 2 = >25-50% filled; 3 = >50-75% filled; 4 = >75-100% filled.
[4]PoMo: rabbit polyclonal and murine monoclonal antibody efficacy study; Rab pAb Fab: rabbit polyclonal IgG Fab fragments efficacy study
[5]ND refers to Not done, that is these antibodies were not tested in vivo.

Table 3 shows the targets (IhfB2, mIhfB4, and IhfA5-mIhfB4 chimer) used to generate each of various rabbit polyclonal sera, providing data for IgG and Fab fragments for each of these targets. All experiments shown were performed as highly controlled therapeutic studies. The table summarizes and provides quantitations regarding the experiments presented in Examples 2 and 3 above, as well as presents data ("PoMo" study code) that are published in 'Monoclonal antibodies against DNA-binding tips of DNABII proteins disrupt biofilms in vitro and induce bacterial clearance in vivo.' (2016) EBioMedicine. August; 10:33-44. For the in vitro vs NTHI biofilms, the methods used were as described in Example 2, above. The exact concentration of antibodies or Fab fragments as indicated was applied to pre-formed biofilms. In particular, the concentration used was 171 nM for all antibodies and fragments used in the in vitro analyses. For the in vivo studies, the methods used were as described in Example 3, above. The exact inoculum (*Haemophilus influenzae* (NTHI) 86-028NP) delivered to each animal's ear to initiate biofilm formation was controlled and infusion of ears was performed with specific quantities of antibody or fragments as indicated. In particular, the concentration used was 342.5 nM for all antibodies and fragments used in the in vivo analyses.

In the in vitro biofilm analysis using rabbit antibodies and Fab fragments, rabbit polyclonal mIhfB4 IgG and rabbit polyclonal IhfA5-mIhfB4 chimer IgG showed 75% and 82% reduction in biomass, respectively. Rabbit polyclonal mIhfB4 Fab and rabbit polyclonal IhfA5-mIhfB4 chimer Fab showed 78% and 87% reduction in biomass, respectively. IhfB2 IgG (control) and IhfB2 Fab (control) showed 0% and % reduction in biomass, respectively. For the in vivo chinchilla model of NTHI induced otitis media, rabbit polyclonal mIhfB4 Fab and rabbit polyclonal IhfA5-mIhfB4 chimer Fab showed 5.5-$\log_{10}$ and 5.2-$\log_{10}$ reduction in CFU NTHI/mg middle ear mucosal biofilm, respectively, whereas rabbit polyclonal IhfB2 Fab (control) showed 0.4-$\log_{10}$ reduction in CFU NTHI/mg middle ear mucosal biofilm. These measurements were performed one day after receipt of the final dose, and are relative to respective naive serum. Rabbit polyclonal mIhfB4 Fab and rabbit polyclonal IhfA5-mIhfB4 chimer Fab showed middle ear biofilm scores of 1.0 and 0.9, respectively, whereas rabbit polyclonal IhfB2 Fab (control) showed a middle ear biofilm score of 3.7. The "PoMo" in vivo study code provided in Table 3 refers to data that are published in 'Monoclonal antibodies against DNA-binding tips of DNABII proteins disrupt biofilms in vitro and induce bacterial clearance in vivo.' (2016) EBioMedicine. August; 10:33-44.

Example 4: Treatment of Oral Disease

A number of oral bacteria (e.g., *Aggregatibacter actinomycetemcomitans, Porphyromonas gingivalis*) have been implicated in the pathogenesis of inflammatory diseases such as periodontitis and peri-implantitis, which destroy alveolar bone and gingiva. Investigations of the pathogenesis of these bacteria are hampered by lack of effective animal models. One of the challenges of investigating the pathogenicity of specific bacteria is the difficulty of establishing a biofilm when exogenous bacteria are introduced into the oral cavity of animals. Though animal models of periodontitis have been developed, cultivable bacteria are rarely recovered from the oral cavity of inoculated animals. Developing an effective animal model which can assess the pathogenicity of specific bacteria will greatly aid in elucidating their pathogenic mechanisms.

The surface of machined titanium dental implants (1.2× 4.5 mm) can be modified by grit blasting with A103 (100 μm) and HCl etching (pH 7.8 for 20 min at 80° C.). Machined and nano-textured implants are incubated in TSB medium inoculated with D7S clinical strain of *Aggregatibacter actinomycetemcomitans* (Aa) for 1 to 3 days at 37° C.

The bacterial biofilm on the implants are analyzed by SEM, as well as by confocal laser scanning microscopy following staining with LIVE/DEAD® BacLight™. Implants with and without established Aa biofilm are transmucosally placed into the alveolar bone of female rats between premolar and incisor region of the maxillae. To detect the presence of Aa biofilm on the implants placed in vivo, bacterial samples are collected from saliva and the oral surfaces of implants after 2 days. Aa can be detected by culture, as well as by PCR analysis. Micro-CT and histological analysis of peri-implant bone and mucosal tissues can be performed at various time points, e.g., six weeks after implantation. The methods and compositions disclosed herein are contemplated to develop both therapeutic as well as preventative strategies for reduction and/or elimination of these biofilms. A decrease in redness, inflammation, and bleeding compared to infected controls would indicate biofilm reduction and/or elimination. In addition, reduced or absent inflammatory or proinflammatory histology and maintenance of torque removal force for the implant screw compared to infected controls would indicate biofilm reduction and/or elimination.

Example 5: Lyme Disease

This experiment provides a mouse model for pre-clinical testing of agents as described to treat lyme disease. See Dresser et al. Pathogens 5(12)e1000680, Epub 2009 Dec. 4. Lyme disease is caused by the microorganism *Borrelia burgdorferi*, a spirochete. *B. burgdorferi* is transmitted via the bite of the *Ixodes* tick and subsequently disseminates, via the bloodstream, to other tissues and organs.

In this animal model, C3H/HeN mice are injected with spirochetes via dorsal subcutaneous and intraperitoneal injection, or via intravenous injection. Blood and biopsy specimens are recovered at approximately 7 days post infection for evaluation of microbial burden and assessment of pathology in tissues and organs. The methods and compositions disclosed herein are contemplated to develop both therapeutic as well as preventative strategies for reduction and/or elimination of the resulting *B. burgdorferi* biofilms which form subsequent to challenge and are believed to contribute to both the pathogenesis and chronic nature of the disease.

Example 6: Cystic Fibrosis

This experiment provides a porcine model for pre-clinical testing of agents to treat cystic fibrosis. See Stoltz et al. (2010) Science Translational Medicine 2(29):29-31. Cystic fibrosis is an autosomal recessive disease due to mutations in a gene that encodes the CF transmembrane conductance regulator (called CFTR) anion channel. In this model, pigs which have been specifically bred to carry a defect in the genes called "CFTR" and called CF pigs spontaneously develop hallmark features of CF lung disease that includes infection of the lower airway by multiple bacterial species. The pigs can be immunized with the agents as described herein to either: 1) immunize these CF pigs with a polypeptide or other immunogenic agent thereby inducing the formation of antibodies which will eradicate bacterial biofilms in the lungs (similarly to how antibodies to IHF eradicated biofilms resident within the middle ears of chinchillas following active immunization), to deliver agents to the lungs of these animals by nebulization to assess the amelioration of the signs of disease and associated pathologies.

Example 7: Tuberculosis

Applicants also provide a pre-clinical model for tuberculosis (TB). See Ordway et al. (2010) Anti. Agents and Chemotherapy 54:1820. The microorganism *Mycobacterium tuberculosis* is responsible for a growing global epidemic. Current figures suggest that there are approximately 8 million new cases of TB and about 2.7 million deaths due to TB annually. In addition to the role of this microbe as a co-infection of individuals with HIV (of the ~45 million infected with HIV, estimates are that ~⅓ are also co-infected with *M. tuberculosis*), its particularly troublesome that isolates have become highly resistant to multiple drugs and no new drug for TB has been introduced in over a quarter of a century. In this animal model, SPF guinea pigs are maintained in a barrier colony and infected via aerosolized spray to deliver ~20 cfu of *M. tuberculosis* strain Erdman K01 bacilli into their lungs. Animals are sacrificed with determination of bacterial load and recovery of tissues for histopathological assessment on days 25, 50, 75, 100, 125 and 150 days post-challenge. Unlike mice which do not develop classic signs of TB, guinea pigs challenged in this manner develop well-organized granulomas with central necrosis, a hallmark of human disease. Further, like humans, guinea pigs develop severe pyogranulomatous and necrotizing lymphadenitis of the draining lymph nodes as part of the primary lesion complex. Use of this model will provide a pre-clinical screen to confirm and identify therapeutic as well as preventative strategies for reduction and/or elimination of the resulting *M. tuberculosis* biofilms which have been observed to form in the lungs of these animals subsequent to challenge and are believed to contribute to both the pathogenesis and chronicity of the disease.

Example 8: Device Application

Multiple animal models of catheter/indwelling device biofilm infections are known. See Otto (2009) Nature Reviews Microbiology 7:555. While typically considered normal skin flora, the microbe *Staphylococcus epidermidis* has become what many regard as a key opportunistic pathogen, ranking first among causative agents of nosocomial infections. Primarily, this bacterium is responsible for the majority of infections that develop on indwelling medical devices which are contaminated by this common skin colonizer during device insertion. While not typically life-threatening, the difficulty associated with treatment of these biofilm infections, combined with their frequency, makes them a serious public health burden. Current costs associated with treatment of vascular catheter associated bloodstream infections alone that are due to *S. epidermidis* amount to $2 billion annually in the United States. In addition to *S. epidermidis*, *E. faecalis* and *S. aureus* are also contaminations found on indwelling medical devices. There are several animal models of catheter-associated *S. epidermidis* infections including rabbits, mice, guinea pigs and rats all of which are used to study the molecular mechanisms of pathogenesis and which lend themselves to studies of prevention and/or therapeutics. Rat jugular vein catheters have been used to evaluate therapies that interfere with *E. faecalis*, *S. aureus* and *S. epidermidis* biofilm formation. Biofilm reduction is often measured three ways—(i) sonicate catheter and calculate CFUs, (ii) cut slices of catheter or simply lay on a plate and score, or (iii) the biofilm can be stained with crystal violet or another dye, eluted, and OD measured as a proxy for CFUs.

Example 9: Vaccine Administration

Methods described herein may be used to elicit immune responses in humans and animals. Immunogenic compositions may be administered to a human and animal subjects in the presence of adjuvants such as but not limited to aluminum salts and liposomes. Those skilled in the art will understand that any number of pharmaceutically acceptable adjuvants can also be used. Immunogenic compositions may be administered to a human or animal subjects intramuscularly, subdermally, intranasally, or through any other suitable route. Immunogenic compositions may be prepared in a manner consistent with the selected mode of administration. Immunogenic compositions may take the form of polypeptides, nucleic acids, or a combination thereof, and may comprise full-length or partial antigens. Additionally or alternatively, immunogenic compositions may take the form of antigen presenting cells (APCs) pulsed with a particular antigen, or APCs transfected with one or more polynucleotides encoding a particular antigen. Administration may comprise a single dose of an immunogenic composition, or an initial administration, followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Example 10: Passive Immunity

Methods described herein may be used to confer passive immunity on a non-immune subject. Passive immunity against a given antigen may be conferred through the transfer of antibodies or antigen binding fragments that specifically recognize or bind to a particular antigen. Antibody donors and recipients may be human or non-human subjects. Additionally or alternatively, the antibody composition may comprise an isolated or recombinant polynucleotide encoding an antibody or antigen binding fragment that specifically recognizes or binds to a particular antigen.

Passive immunity may be conferred in cases where the administration of immunogenic compositions poses a risk for the recipient subject, the recipient subject is immunocompromised, or the recipient subject requires immediate immunity. Immunogenic compositions may be prepared in a manner consistent with the selected mode of administration. Compositions may comprise whole antibodies, antigen binding fragments, polyclonal antibodies, monoclonal antibodies, antibodies generated in vivo, antibodies generated in vitro, purified or partially purified antibodies, or whole serum. Administration may comprise a single dose of an antibody composition, or an initial administration followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Figure 8A:
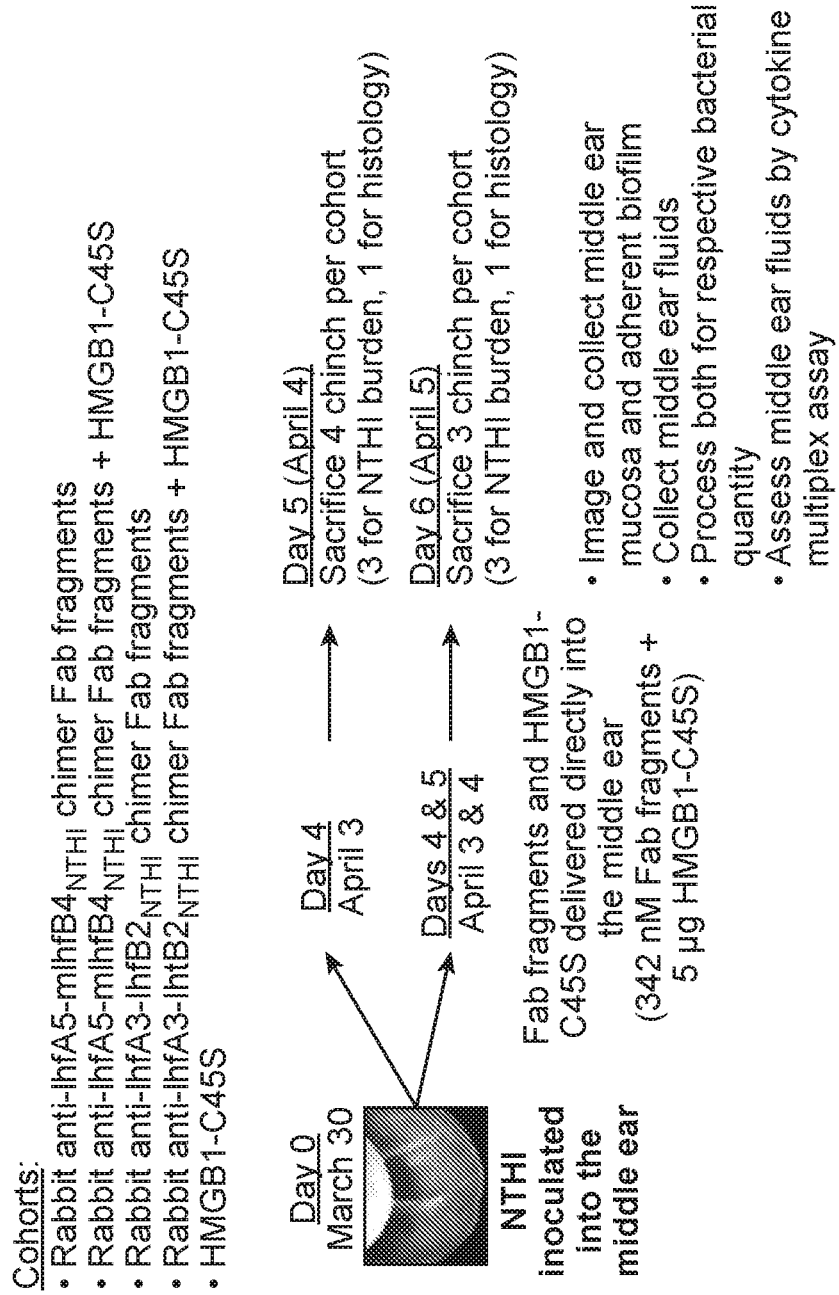
FIGS. 8A-8C show the results of a study evaluating the therapeutic efficacy of IHF$_{NTHI}$ Fab fragments+HMGB1-C45S. Circles free of shading indicating individual mucosal biofilm scores for samples taken, mean mucosal biofilm socre indicated by bar graph score per dose administered.
Figure 8B:
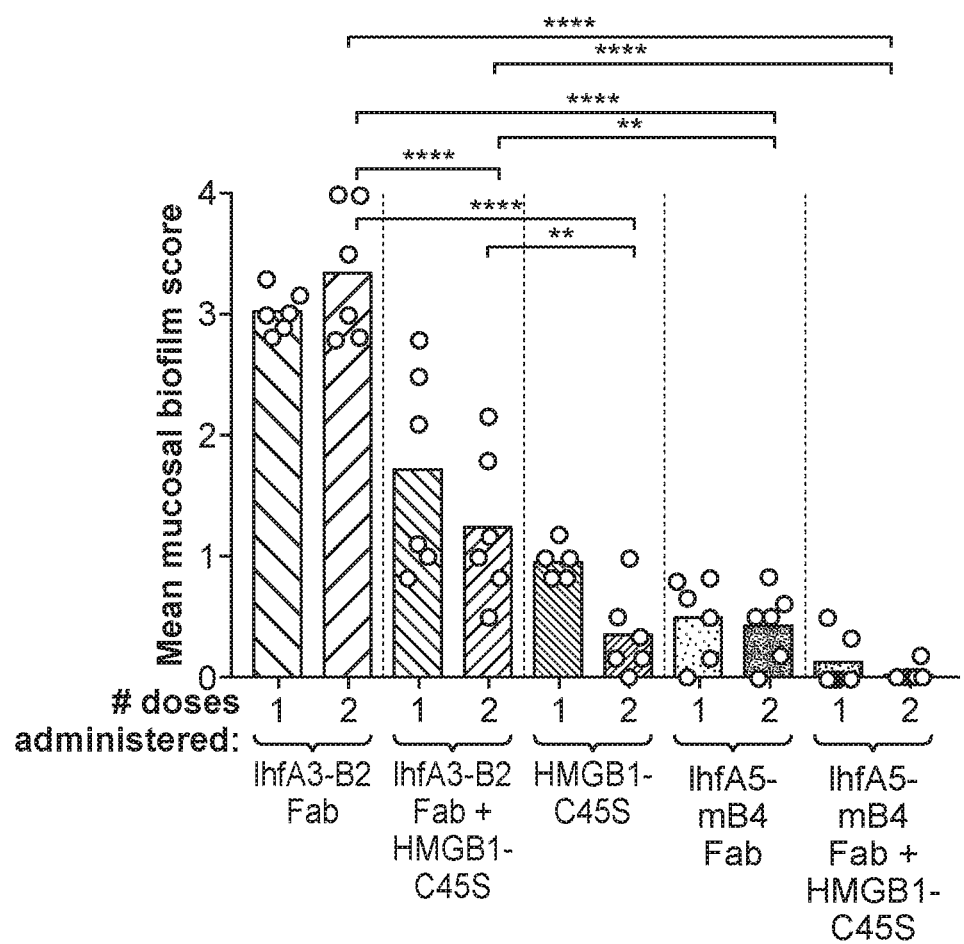
Figure 8C:
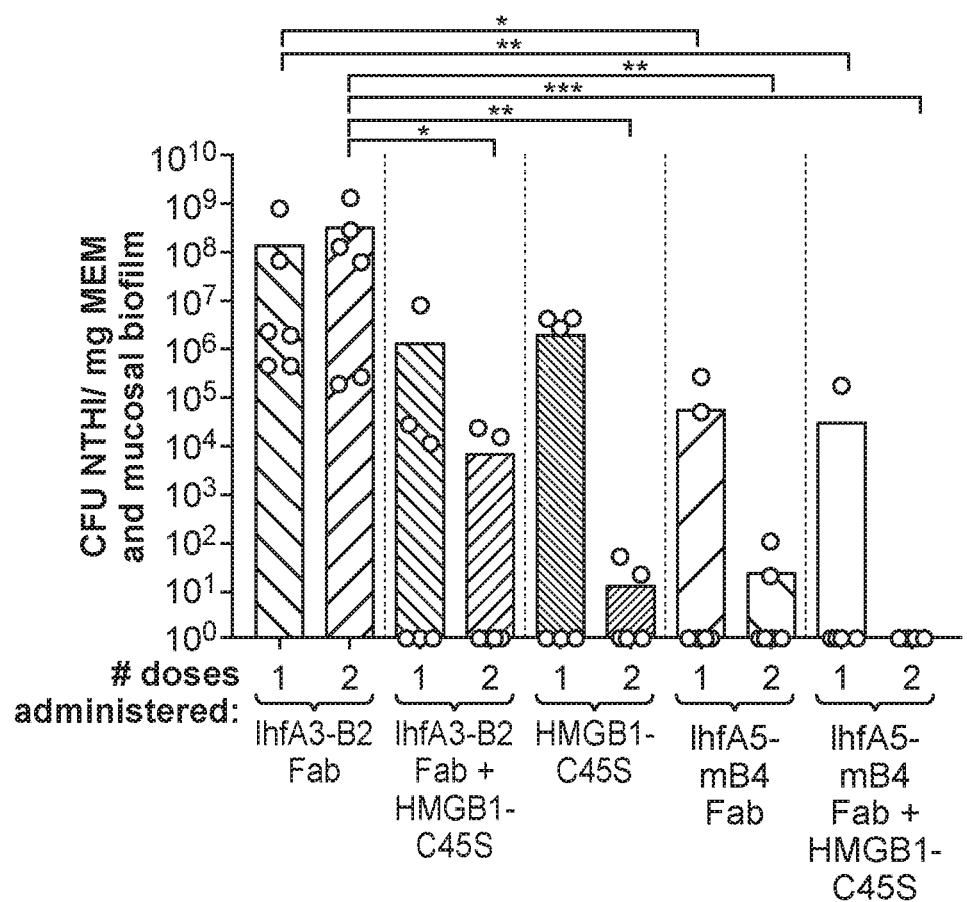

Example 11: Synergistic Therapeutic Efficacy of $IHF_{NTHi}$ Fab Fragments+HMGB1-C45S Chinchillas were challenged by transbullar injection with 1000 CFU of NTHi strain 86-028NP on day 0. On day 4, chinchillas were treated with formulations noted in FIG. 8A. On day 5, a subset of chinchillas were treated again was the same formulation. Chinchillas were euthanized 1 day after final treatment, and middle ears were scored for biofilm (left) and CFU in the middle ear mucosa were quantified (right). The combination of HMGB1-C45S and the tail-directed Fab showed efficacy equal to the HMGB1-C45S treatment alone, while the combination of the DNA binding tip-directed Fab and HMGB1-C45S displayed increased efficacy compared to either monotherapy. (See FIGS. 8B and 8C).

EQUIVALENTS

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that the materials, methods, and examples provided here are representative of preferred embodiments, are exemplary, and are not intended as limitations on the scope of the invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A recombinant polypeptide consisting of the polypeptide of SEQ ID NO: 50.

2. A vaccine composition comprising an effective amount of the recombinant polypeptide of claim 1 and a pharmaceutically acceptable carrier.

3. The vaccine composition of claim 2, further comprising one or more of an adjuvant, a preservative, a stabilizer, at least one antibiotic or an additional active ingredient.

4. A method to disrupt or prevent the formation of a biofilm in a subject in need thereof, comprising administering to the subject an effective amount of the vaccine composition of claim 3.

5. A method to disrupt or prevent the formation of a biofilm in a subject in need thereof, comprising administering to the subject an effective amount of a polypeptide of claim 1.

6. A recombinant polypeptide comprising the peptide of SEQ ID NO: 12 (FLEEIRLSLESGQDVKLSGF) and the peptide of SEQ ID NO: 15 (TLSAKEIENMVKDILEFISQ) joined via a linker polypeptide comprising the peptide of SEQ ID NO: 44 (GPSL).

7. A composition comprising an effective amount of the recombinant polypeptide of claim 6 and a pharmaceutically acceptable carrier.

8. The composition of claim 7, further comprising one or more of an adjuvant, a preservative, a stabilizer, at least one antibiotic or an additional active ingredient.

9. A method to disrupt or prevent the formation of a biofilm in a subject in need thereof, comprising administering to the subject an effective amount of a vaccine composition of claim 2.

10. A recombinant polypeptide comprising the peptide of SEQ ID NO: 13 (RPGRNPKTGDVVPVSARRVV) and the peptide of SEQ ID NO: 17 (FSLHHRQPRLGRNPKTGDSV).

11. The recombinant polypeptide of claim 10, wherein the peptide of SEQ ID NO: 13 and the peptide of SEQ ID NO: 17 are joined via a linker polypeptide comprising the peptide of SEQ ID NO: 44 (GPSL).

12. A method to disrupt or prevent the formation of a biofilm in a subject in need thereof, comprising administering to the subject an effective amount of a polypeptide of claim 11.

13. A vaccine composition comprising an effective amount of the recombinant polypeptide of claim 10 and a pharmaceutically acceptable carrier.

14. The vaccine composition of claim 13, further comprising one or more of an adjuvant, a preservative, a stabilizer, at least one antibiotic or an additional active ingredient.

15. A method to disrupt or prevent the formation of a biofilm in a subject in need thereof, comprising administering to the subject an effective amount of the vaccine composition of claim 14.

16. A method to disrupt or prevent the formation of a biofilm in a subject in need thereof, comprising administering to the subject an effective amount of the vaccine composition of claim 13.

17. A method to disrupt or prevent the formation of a biofilm in a subject in need thereof, comprising administering to the subject an effective amount of a polypeptide of claim 10.

18. A recombinant polypeptide comprising the polypeptide of SEQ ID NO: 50.

19. A composition comprising the polypeptide of claim 18 and a pharmaceutically acceptable carrier.

20. The composition of claim 19, further comprising one or more of an adjuvant, a preservative, a stabilizer, at lease one antiobiotic or an additional active ingredient.

21. A vaccine composition comprising an effective amount of the recombinant polypeptide of claim 18 and a pharmaceutically acceptable carrier.

22. The vaccine composition of claim 21, further comprising one or more of an adjuvant, a preservative, a stabilizer, at lease one antiobiotic or an additional active ingredient.

23. A method to distrupt or preserve the formation of a biofilm in a subject in need thereof, comprising administering to the subject an effective amount of the vaccine composition of claim 22.

24. A method to distrupt or preserve the formation of a biofilm in a subject in need thereof, comprising administering to the subject an effective amount of the vaccine composition of claim 21.

25. A method to distrupt or preserve the formation of a biofilm in a subject in need thereof, comprising administering to the subject an effective amount of the polypeptide of claim 18.

* * * * *

UNITED STATES PATENT AND TRADEMARK OFFICE
CERTIFICATE OF CORRECTION

PATENT NO. : 11,564,982 B2
APPLICATION NO. : 16/475656
DATED : January 31, 2023
INVENTOR(S) : Lauren O. Bakaletz and Steven D. Goodman It is certified that error appears in the above-identified patent and that said Letters Patent is hereby corrected as shown below:

In the Claims

At Column 198, Line 10 – "lease" should be replaced with "least".

At Column 198, Line 17 – "lease" should be replaced with "least".

At Column 198, Line 23 – "distrupt" should be replaced with "disrupt" and "preserve" should be replaced with "prevent".

At Column 198, Line 27 – "distrupt" should be replaced with "disrupt" and "preserve" should be replaced with "prevent".

Signed and Sealed this
Fourth Day of April, 2023

*Katherine Kelly Vidal*
Katherine Kelly Vidal
*Director of the United States Patent and Trademark Office*